United States Patent
Gurney et al.

(10) Patent No.: US 9,873,726 B2
(45) Date of Patent: Jan. 23, 2018

(54) METHODS FOR IDENTIFYING AND ISOLATING CELLS EXPRESSING A POLYPEPTIDE

(71) Applicant: OncoMed Pharmaceuticals, Inc., Redwood City, CA (US)

(72) Inventors: Austin L. Gurney, San Francisco, CA (US); Alexandra L. L. Lazetic, San Jose, CA (US); Christopher J. Bond, San Mateo, CA (US)

(73) Assignee: ONCOMED PHARMACEUTICALS, INC., Redwood City, CA (US)

( * ) Notice: Subject to any disclaimer, the term of this patent is extended or adjusted under 35 U.S.C. 154(b) by 7 days.

(21) Appl. No.: 15/210,250

(22) Filed: Jul. 14, 2016

(65) Prior Publication Data

US 2017/0002054 A1    Jan. 5, 2017

Related U.S. Application Data

(62) Division of application No. 14/678,592, filed on Apr. 3, 2015, now Pat. No. 9,422,546, which is a division
(Continued)

(51) Int. Cl.
*G01N 33/53* (2006.01)
*C07K 14/73* (2006.01)
(Continued)

(52) U.S. Cl.
CPC ........ *C07K 14/70514* (2013.01); *C07K 16/00* (2013.01); *C07K 16/22* (2013.01);
(Continued)

(58) Field of Classification Search
CPC .. C07K 14/70514; C07K 16/00; C07K 16/22; C07K 16/28; C07K 16/2851;
(Continued)

(56) References Cited

U.S. PATENT DOCUMENTS 4,946,778 A    8/1990   Ladner
5,225,539 A    7/1993   Winter
(Continued)

FOREIGN PATENT DOCUMENTS

EP    1 447 413 A2    1/2006
WO    WO 98/18809 A1    5/1998
(Continued)

OTHER PUBLICATIONS

Al-Lazikani, B., et al., "Standard conformations for the canonical structures of immunoglobulins," *J. Mol. Biol.* 273:927-948, Academic Press, United Kingdom (1997).
(Continued)

*Primary Examiner* — Reza Ghafoorian
(74) *Attorney, Agent, or Firm* — Sterne, Kessler, Goldstein and Fox P.L.L.C.

(57) ABSTRACT

The invention relates to novel polypeptides and cells comprising the polypeptides. The polypeptides and cells are used in methods to identify and/or isolate cells producing a protein with specific biological functions. In particular, the methods may be used for identifying, selecting, and isolating cells producing antigen-specific monoclonal antibodies.

17 Claims, 11 Drawing Sheets

Related U.S. Application Data of application No. 14/020,012, filed on Sep. 6, 2013, now Pat. No. 9,023,621, which is a division of application No. 13/025,733, filed on Feb. 11, 2011, now Pat. No. 8,551,715.

(60) Provisional application No. 61/437,889, filed on Jan. 31, 2011, provisional application No. 61/304,251, filed on Feb. 12, 210.

(51) Int. Cl.
    *C07K 16/00*     (2006.01)
    *C07K 16/22*     (2006.01)
    *C07K 16/28*     (2006.01)
    *G01N 33/68*     (2006.01)
    *C12N 15/10*     (2006.01)

(52) U.S. Cl.
CPC .......... *C07K 16/28* (2013.01); *C07K 16/2851* (2013.01); *C07K 16/2863* (2013.01); *C12N 15/1037* (2013.01); *G01N 33/6845* (2013.01); *G01N 33/6854* (2013.01); *C07K 2317/34* (2013.01); *C07K 2317/52* (2013.01); *C07K 2317/64* (2013.01); *C07K 2319/035* (2013.01); *C07K 2319/30* (2013.01); *C07K 2319/43* (2013.01); *C07K 2319/60* (2013.01)

(58) Field of Classification Search
CPC ............ C07K 16/2863; C07K 2317/52; C07K 2317/64; C07K 2319/30; C07K 2319/43; C07K 2319/60; C07K 2317/34; C07K 2319/35; G01N 33/6845; G01N 33/6854; C12N 15/1037

See application file for complete search history.

(56) References Cited

U.S. PATENT DOCUMENTS

| | | |
|---|---|---|
| 5,545,806 A | 8/1996 | Lonberg et al. |
| 5,545,807 A | 8/1996 | Surani et al. |
| 5,569,825 A | 10/1996 | Lonberg et al. |
| 5,585,089 A | 12/1996 | Queen et al. |
| 5,625,126 A | 4/1997 | Lonberg et al. |
| 5,633,425 A | 5/1997 | Lonberg et al. |
| 5,641,870 A | 6/1997 | Rinderknecht et al. |
| 5,661,016 A | 8/1997 | Lonberg et al. |
| 5,693,761 A | 12/1997 | Queen et al. |
| 5,693,762 A | 12/1997 | Queen et al. |
| 5,731,168 A | 3/1998 | Carter et al. |
| 5,885,793 A | 5/1999 | Griffiths et al. |
| 5,969,108 A | 10/1999 | McCafferty et al. |
| 6,096,871 A | 8/2000 | Presta et al. |
| 6,121,022 A | 9/2000 | Presta et al. |
| 6,172,197 B1 | 1/2001 | McCafferty et al. |
| 6,300,064 B1 | 10/2001 | Knappik et al. |
| 6,423,316 B1 | 7/2002 | Riesbeck et al. |
| 6,521,404 B1 | 2/2003 | Griffiths et al. |
| 6,544,731 B1 | 4/2003 | Griffiths et al. |
| 6,555,313 B1 | 4/2003 | Griffiths et al. |
| 6,582,915 B1 | 6/2003 | Griffiths et al. |
| 6,593,081 B1 | 7/2003 | Griffiths et al. |
| 6,653,068 B2 | 11/2003 | Frisch et al. |
| 6,706,484 B1 | 3/2004 | Knappik et al. |
| 6,919,183 B2 | 7/2005 | Fandl et al. |
| 7,094,571 B2 | 8/2006 | Harvey et al. |
| 7,153,661 B2 | 12/2006 | Koide |
| 7,166,423 B1 | 1/2007 | Miltenyi et al. |
| 7,176,179 B1 * | 2/2007 | Pollock .................. C07K 14/545 514/19.3 |
| 7,264,963 B1 | 9/2007 | Knappik et al. |
| 7,402,394 B2 | 7/2008 | Giorgi et al. |
| 7,479,538 B2 | 1/2009 | Zhabilov |
| 7,498,304 B2 | 3/2009 | Kotkow et al. |
| 7,790,655 B2 | 9/2010 | Gao et al. |
| 7,858,559 B2 | 12/2010 | Zauderer et al. |
| 8,067,339 B2 | 11/2011 | Prinz et al. |
| 8,551,715 B2 | 10/2013 | Gurney et al. |
| 8,945,878 B2 | 2/2015 | Gurney et al. |
| 9,023,621 B2 | 5/2015 | Gurney et al. |
| 9,422,546 B2 | 8/2016 | Gurney et al. |
| 2003/0170753 A1 | 9/2003 | Koide |
| 2003/0232395 A1 | 12/2003 | Hufton et al. |
| 2007/0048740 A1 | 3/2007 | Isogai et al. |
| 2010/0009866 A1 | 1/2010 | Prinz et al. |
| 2011/0038854 A1 * | 2/2011 | Kotenko ............ C07K 14/7156 424/133.1 |
| 2011/0076752 A1 | 3/2011 | Wu et al. |
| 2015/0315565 A1 | 11/2015 | Gurney et al. |

FOREIGN PATENT DOCUMENTS

| | | |
|---|---|---|
| WO | WO 98/41613 A1 | 9/1998 |
| WO | WO 1998/041613 * | 9/1998 ............... C12N 5/00 |
| WO | WO 98/43850 A1 | 10/1998 |
| WO | WO 00/20574 A2 | 4/2000 |
| WO | WO 00/24897 A1 | 5/2000 |
| WO | WO 00/42176 A1 | 7/2000 |
| WO | WO 02/057423 A2 | 7/2002 |
| WO | WO 2002/088334 A1 | 11/2002 |
| WO | WO 2007/115230 A2 | 10/2007 |
| WO | WO 2008/100816 A2 | 8/2008 |
| WO | WO 2010/005863 A1 | 1/2010 |
| WO | WO 2011/100566 A2 | 8/2011 |
| WO | WO 2012/074948 A2 | 6/2012 |

OTHER PUBLICATIONS

Brennan, M., et al., "Preparation of bispecific antibodies by chemical recombination of monoclonal immunoglobulin G1 fragments," *Science* 229:81-83, American Association for the Advancement of Science, United States (1985).

Clackson, T., et al., "Making antibody fragments using phage display libraries," *Nature* 352:624-628, Nature Publishing Group, United Kingdom (1991).

Gray, F., et al., "Secretion capture and report web: use of affinity derivatized agarose microdroplets for the selection of hybridoma cells," *J. Immunol. Methods* 182:155-163, Elsevier, Netherlands (1995).

Gruber, M., et al., "Efficient tumor cell lysis mediated by a bispecific single chain antibody expressed in *Escherichia coli*," *J. Immunol.* 152:5368-5374, American Association of Immunologists, United States (1994).

Hoogenboom, H., and Winter, G., "By-passing immunisation. Human antibodies from synthetic repertoires of germline VH gene segments rearranged in vitro," *J. Mol. Biol.* 227:381-382, Academic Press, United States (1992).

Huse, W., et al., "Generation of a large combinatorial library of the immunoglobulin repertoire in phage lambda," *Science* 246:1275-1281, American Association for the Advancement of Science, United States (1989).

Kenney, J., et al., "Production of Monoclonal Antibodies Using a Secretion Capture Report Web," *Nat. Biotechnol.* 13:787-790, Nature American Publishing, United States (1995).

Kohler, G. and Milstein, C., "Continuous cultures of fused cells secreting antibody of predefined specificity," *Nature* 256:495-497, Nature Publishing Group, United Kingdom (1975).

Kostelny, S., et al., "Formation of a bispecific antibody by the use of leucine zippers," *J. Immunol.* 148:1547-1553, American Association of Immunologists, United States (1992).

Lee, C., et al., "Bivalent antibody phage display mimics natural immunoglobulin," *J. Immunol. Methods* 284:119-132, Elsevier, Netherlands (2004).

Lee, H., et al., "Generation and characterization of a novel single-gene-encoded single-chain immunoglobulin molecule with antigen binding activity and effector functions," *Mol. Immunol.* 36:61-71, Pergamon Press, United Kingdom (1999).

(56) References Cited

OTHER PUBLICATIONS

Luckow, V. and Summers, M., "Trends in the development of baculovirus expression vectors," *Bio/Technology* 6:47-55, Wiley-VCH Verlag GmbH & Co. KGaA, Germany (1988).

Marks, J., et al., "By-passing immunization. Human antibodies from V-gene libraries displayed on phage," *J. Mol. Biol.* 222:581-597, Academic Press, United Kingdom (1991).

Marks, J., et al., "By-passing immunization: building high affinity human antibodies by chain shuffling," *Bio/Technology* 10:779-783, Nature Publishing Company, United States (1992).

McCafferty, J., et al., "Phage antibodies: filamentous phage displaying antibody variable domains," *Nature* 348:552-554, Nature Publishing Group, United Kingdom (1990).

Milstein, C., et al., "Hybrid hybridomas and their use in immunohistochemistry," *Nature* 305:537-539, Nature Publishing Group, United Kingdom (1983).

Parks, D., et al., "Antigen-specific identification and cloning of hybridomas with fluorescense-activated cell sorter," *Proc. Natl. Acad. Sci. USA* 76:1962-1966, National Academy of Sciences, United States (1979).

Rothe, C., et al., "The human combinatorial antibody library HuCAL Gold comines diversification of all six CDRs according to the natural immune system with a novel display method for efficient selection of high-affinity antibodies," *J. Mol. Bio.* 376:1182-1200, Academic Press, United Kingdom (2008).

Shalaby, M., et al., "Development of humanized bispecific antibodies reactive with cytotoxic lymphocytes and tumor cells overexpressing the HER2 protooncogene," *J. Exp. Med.* 175:217-225, Rockefeller University Press, United States (1992).

Sheets, M., et al, "Efficient construction of a large nonimmune phage antibody library: the production of high-affinity human single-chain antibodies to protein antigens," *Proc. Natl. Acad. Sci. USA* 95:6157-6162, National Academy of Sciences, United States (1998).

Kozbor, D., et al., "Comparative phenotypic analysis of available human hybridoma fusion partners," *Methods Enzymol.* 121:120-140, Academic Press, United States (1986).

Traunecker, A., et al., "Bispecific single chain molecules (Janusins) target cytotoxic lymphocytes on HIV infected cells," *EMBO J.* 10:3655-3659, Nature Publishing Group, United Kingdom (1991).

Tutt, A., et al., "Trispecific F(ab')3 derivatives that use cooperative signaling via the TCR/CD3 complex and CD2 to activate and redirect resting cytotoxic T cells," *J. Immunol.* 147:60-69, American Association of Immunologists, United States (1991).

Vaughan, T., et al., "Human antibodies with sub-nanomolar affinities isolated from a large non-immunized phage display library," *Nat. Biotechnol.* 14:309-314, Nature American Publishing, United States (1996).

International Search Report mailed on Jul. 28, 2011 for International Patent Application No. PCT/US11/24554, ISA/US, Alexandria, VA, 4 pages.

Supplementary European Search Report and European Search Opinion completed Oct. 11, 2013 for European Patent Application No. 11742877.1, EPO, Munich, Switzerland.

UNIPROT Identifier No. B9UIC3, "Luciferase/green fluorescent protein fusion protein," last modified Oct. 16, 2013, Accessed at http://www.uniprot.org/uniprot/B9U1C3, 3 pages.

UNIPROT Identifier No. P01859 (IGHG2_Human), "Ig gamma-2 chain C region," last modified Apr. 16, 2014, Accessed at http://www.uniprot.org/uniprot/P01859, 9 pages.

UNIPROT Identifier No. P01868 (IGHG1_Mouse), "Ig gamma-1 chain C region.secreted form," last modified Feb. 19, 2014, Accessed at http://www.uniprot.org/uniprot/P01868, 7 pages.

UNIPROT Identifier No. P01869 (IGH1M_MOUSE), "Ig gamma-1 chain C region, membrane bound form," last modified Mar. 19, 2014, Accessed at http://www.uniprot.org/uniprot/P01869, 7 pages.

UNIPROT Identifier No. S6BGE5 (S6BGE5_HUMAN), "IgG H chain," last modified Feb. 19, 2014, Accessed at http://www.uniprot.org/uniprot/S6BGE5, 3 pages.

Marianayagam, N.J., et al., "The power of two: protein dimerization in biology," *Trends Biochem Sci* 29(11):618-625, Elsevier Ltd., England (2004).

Pule, M., et al., "Artificial T-cell Receptors," *Cytotherapy* 5(3)211-226, Elsevier, England (2003).

International Preliminary Report on Patentability for International Application No. PCT/US2011/024554, issued Aug. 14, 2012, 6 pages.

\* cited by examiner

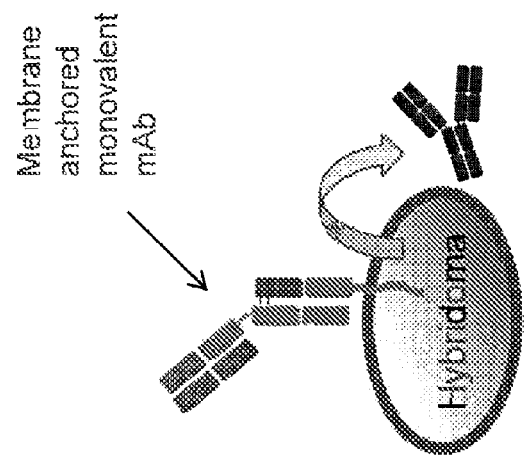
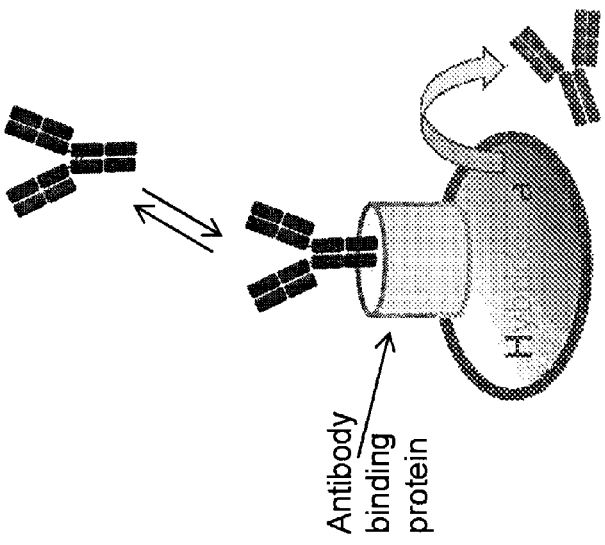
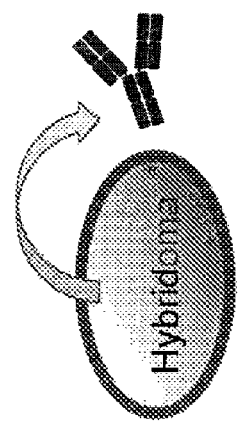

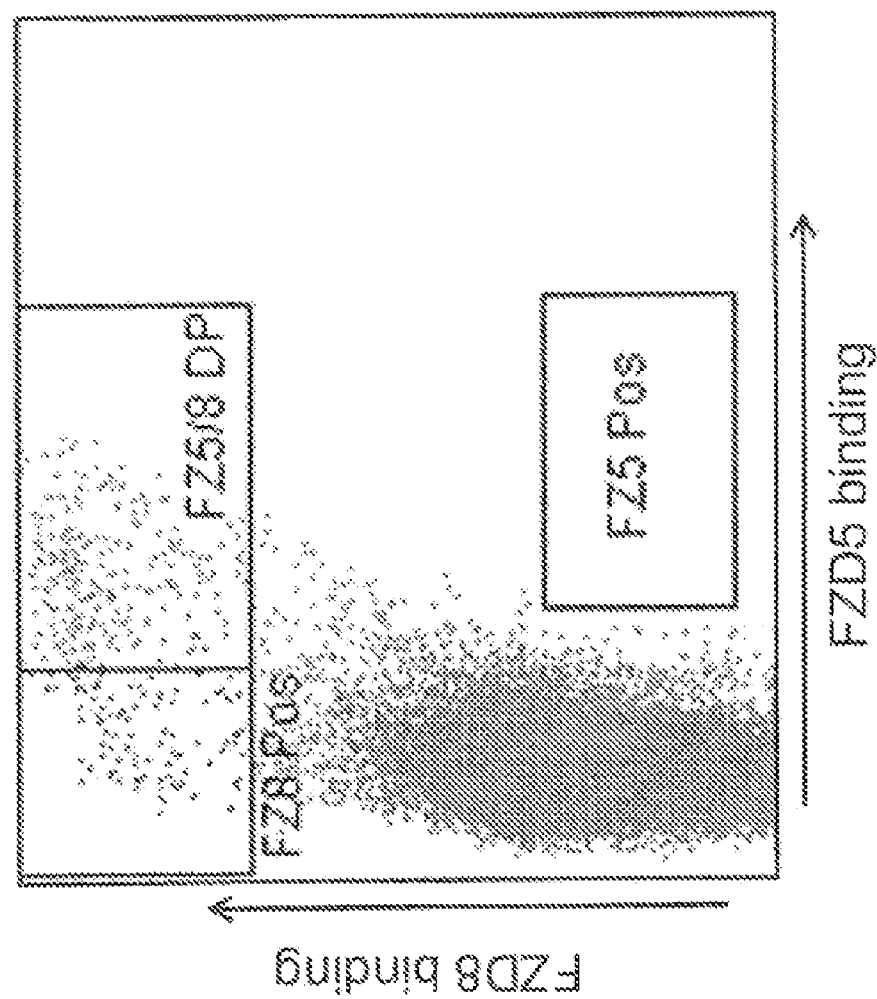

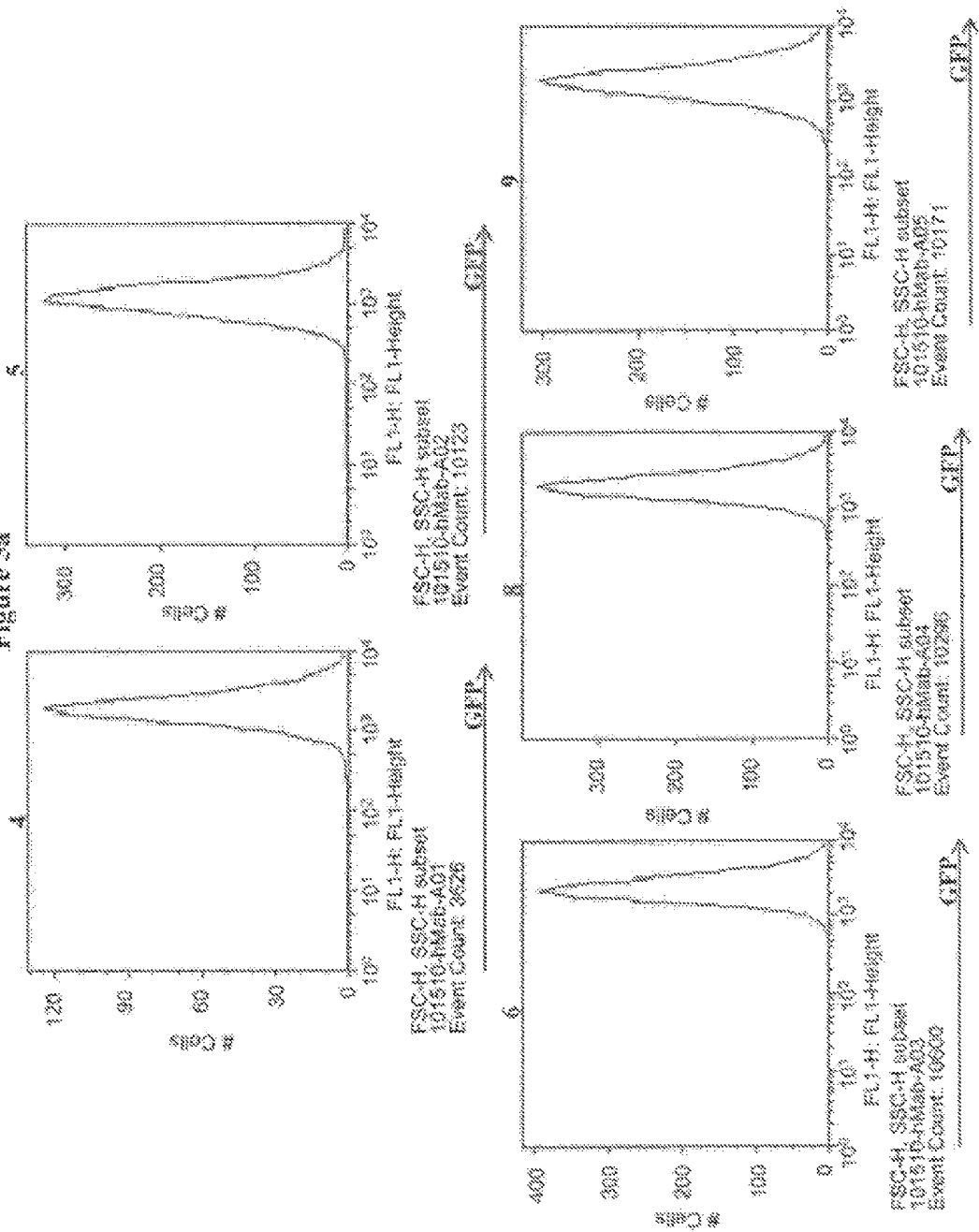

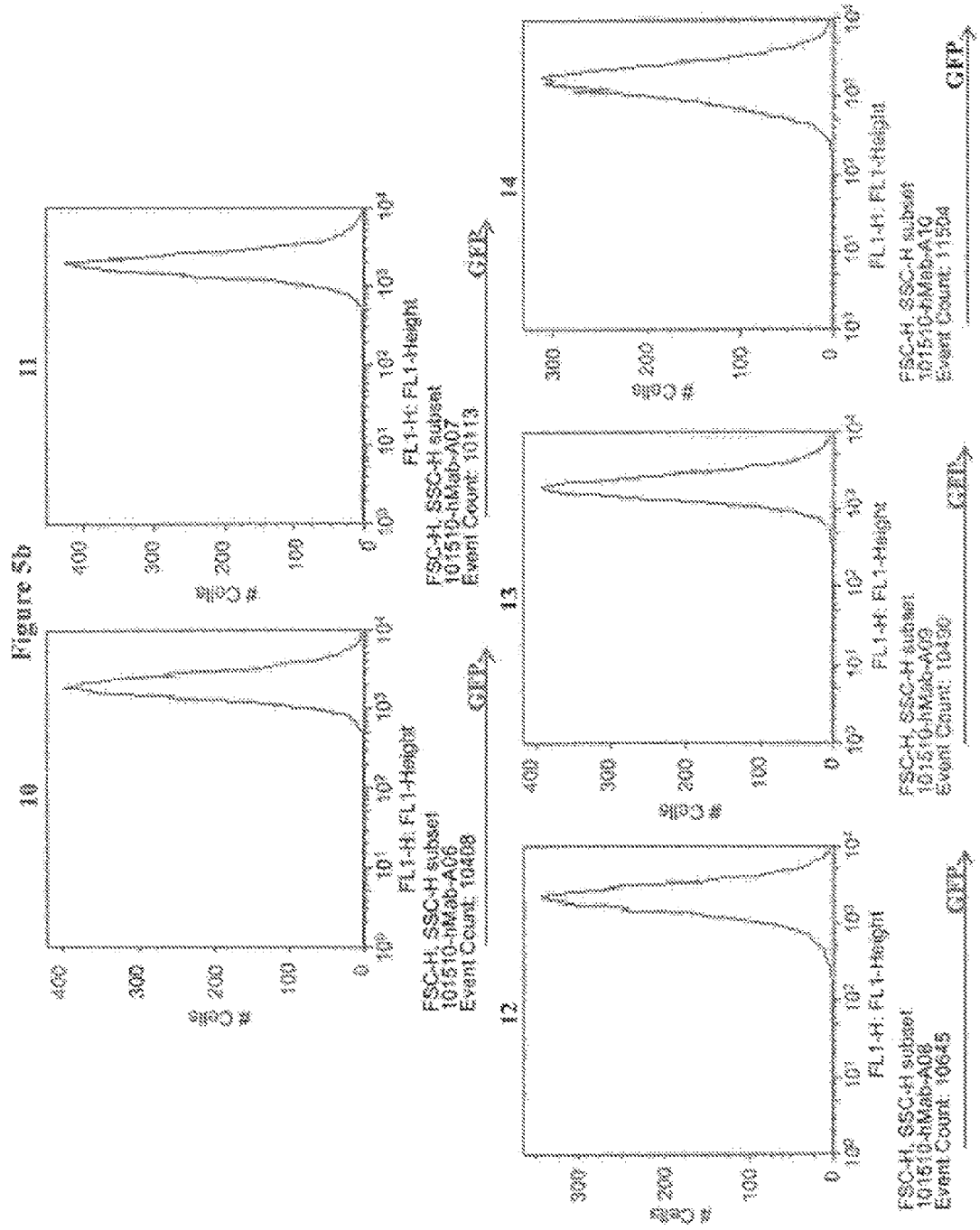

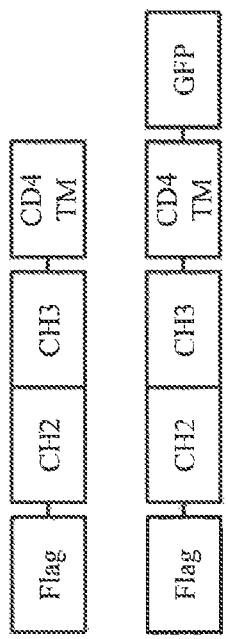
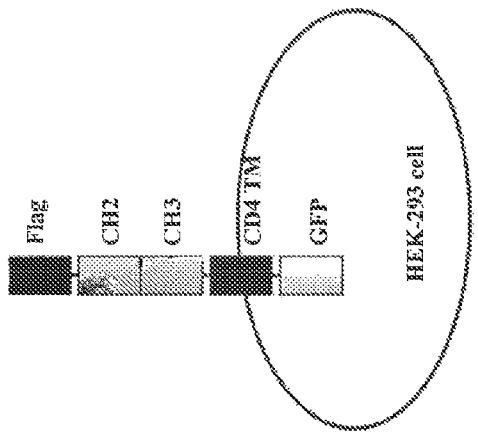
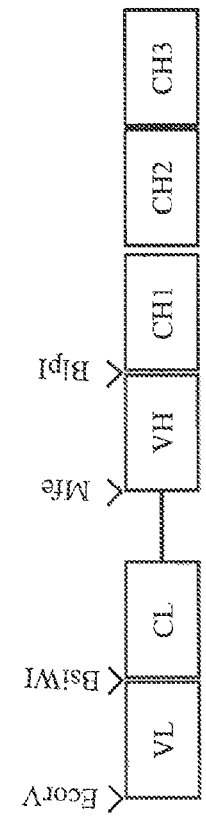
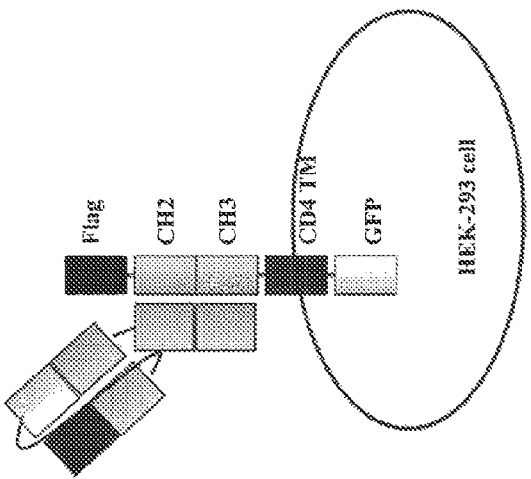

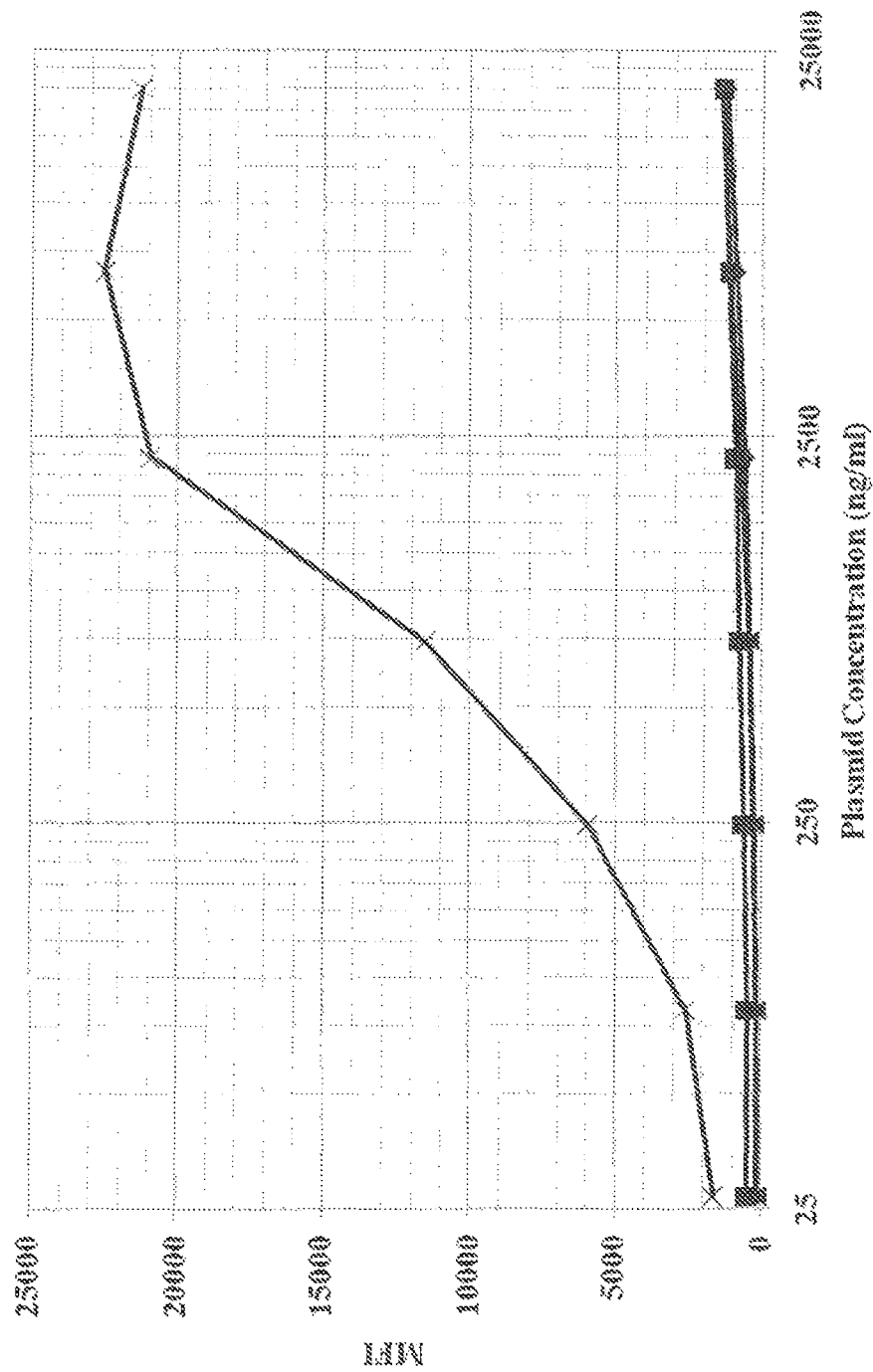

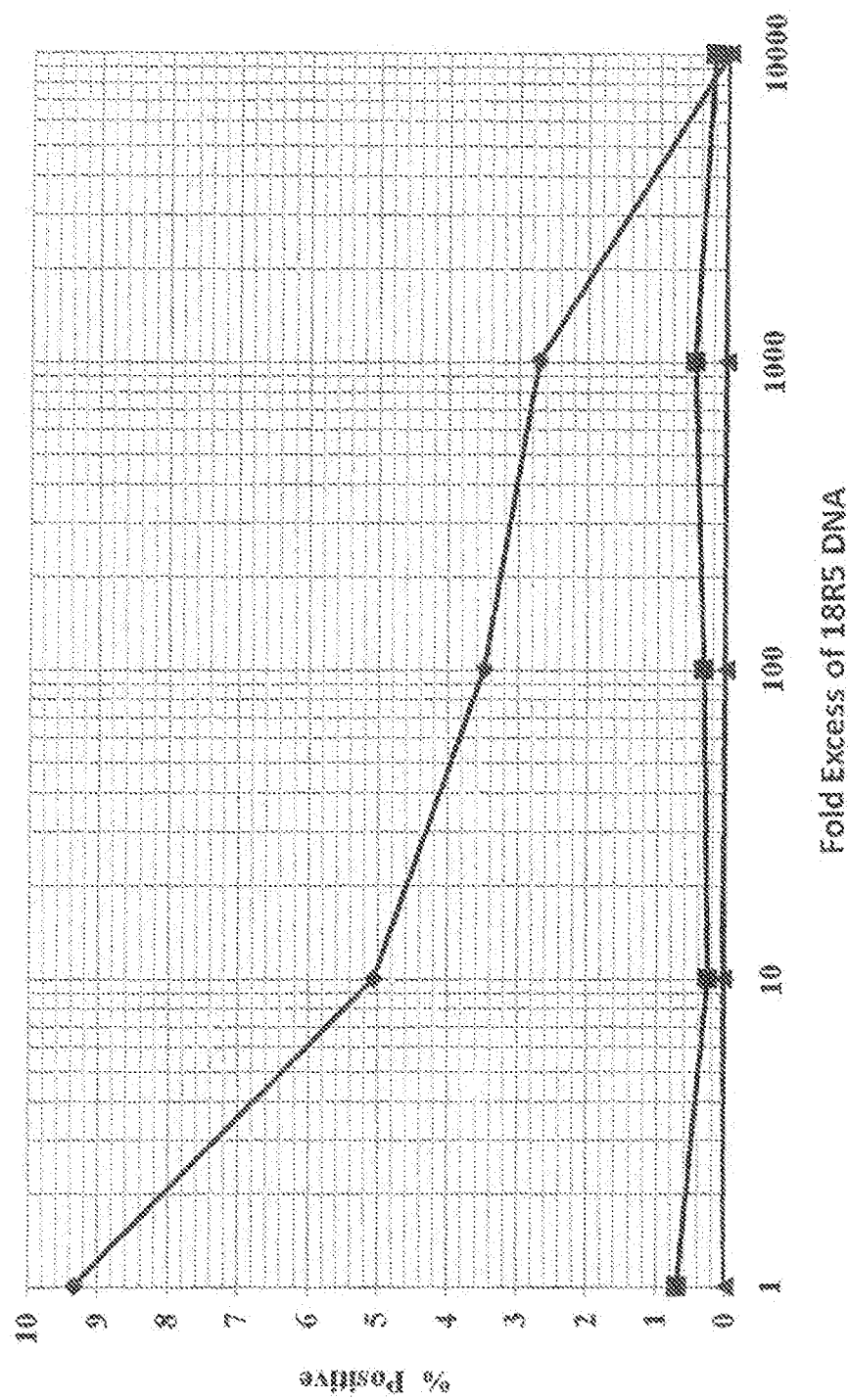

METHODS FOR IDENTIFYING AND ISOLATING CELLS EXPRESSING A POLYPEPTIDE

CROSS REFERENCE TO RELATED APPLICATIONS

This application is a divisional of U.S. application Ser. No. 14/678,592, filed Apr. 3, 2015, now allowed, which is a divisional of U.S. application Ser. No. 14/020,012, filed Sep. 6, 2013, now U.S. Pat. No. 9,023,621, which is a divisional of U.S. application Ser. No. 13/025,733, filed Feb. 11, 2011, now U.S. Pat. No. 8,551,715, which claims the priority benefit of U.S. Provisional Application No. 61/304,251, filed Feb. 12, 2010 and U.S. Provisional Application No. 61/437,889, filed Jan. 31, 2011, each of which is hereby incorporated by reference herein in its entirety.

REFERENCE TO SEQUENCE LISTING SUBMITTED ELECTRONICALLY

The content of the electronically submitted sequence listing (Name: 2293_0680006_Seq_Listing.ascii.txt; Size: 72,899 bytes; and Date of Creation: Jul. 12, 2016) filed herewith is incorporated herein by reference in its entirety.

FIELD OF THE INVENTION

The field of this invention generally relates to novel polypeptides and cells comprising the polypeptides. The invention also relates to using the polypeptides in methods to identify and/or isolate cells expressing the polypeptides. The methods may be used for identifying and isolating cells producing antigen-specific monoclonal antibodies.

BACKGROUND OF THE INVENTION

Since the development of monoclonal antibody technology in the 1970s, monoclonal antibodies have become an increasingly important class of therapeutic agents. Hybridoma technology is still the most commonly used method for producing monoclonal antibodies. The monoclonal antibodies are secreted from hybridoma cells that are created by fusing normal antibody producing B-cells with immortal myeloma cells or other immortal cells. The process of monoclonal antibody development usually involves several cycles of screening supernatants to identify a hybridoma producing an antibody that binds to the antigen of interest.

The identification of hybridomas that produce monoclonal antibodies to an antigen of interest is typically accomplished by ELISA screening. Supernatant produced by pools of random hybridoma clones from a hybridoma library can be screened. This method has limitations, because it must be followed by limiting dilution of the positive pool(s) to isolate individual clones and then all clones need to be rescreened. In some cases, the hybridoma library is cloned by limiting dilution as a first step producing a very large number of individual clones to screen. Any method that includes a limiting dilution step is problematic, because it is time consuming and very labor intensive. Furthermore, in some circumstances the desired clone may represent an extremely low percentage of the hybridoma library, making the identification of the rare clone difficult. In addition, the ELISA screening approach identifies binding activity to a single antigen. To determine if a monoclonal antibody binds to more than one antigen, multiple successive ELISA screenings must be undertaken with the different individual antigens.

It would be advantageous if the cell producing an antibody retained the antibody in a form (e.g., at the surface of the cell) that would allow the antibody-producing cell itself to be directly identified. This strategy is one of the reasons phage display technology has been so successful. In fact, normal B-cells make membrane-bound immunoglobulin and this molecule is a core component of the B-cell receptor complex that signals in response to binding with antigen. The presence of native membrane-bound antibody has previously been used in an attempt to directly isolate hybridomas (see, Parks et al. 1979, PNAS, 76:1962-1966). However, the extremely low levels of membrane-bound antibody made this method of limited use. Several other techniques have been developed to further this goal. One method is the "secretion capture report web" (SCRW) which encapsulates cells in biotinylated agarose microdroplets and then successively incubates the drop suspension with avidin and biotinylated anti-mouse IgG. Avidin serves as a bridge between the biotinylated agarose and the biotinylated anti-mouse antibody to form capture sites within the drops to trap antibody being secreted by the cell. These antibody-containing microdroplets can be screened for the ability to bind a reporter (e.g., a fluorescent-tagged antigen) and the droplets can be isolated by flow cytometry. (See, Kenney et al., 1995, *Nature Biotechnology* 8:787-90; Gray et al., 1995, *J. Immunol. Methods* 182:155-63.) Other methods are based upon the ability to transiently capture a secreted protein or antibody on the surface of a cell. The "captured" protein or antibody can be detected on the cell surface by binding of a reporter molecule (e.g., a fluorescent-tagged antigen) and isolated, for example, by flow cytometry (see, e.g., U.S. Pat. Nos. 6,919,183 and 7,166,423; U.S. Patent App. No. 2010/0009866).

Each of these techniques has limitations. The agarose microdroplet technique is technically difficult and requires special equipment to generate the agarose microdroplets. In addition cells can be sensitive to the encapsulation process. The cell surface capture methods do not fully discriminate between the antibody produced by the hybridoma cell of interest and antibodies produced by other hybridoma cells. Diffusion of the antibody or protein of interest between neighboring cells can be problematic. For example, an antibody can dissociate from the capture molecule on the cell that produced it and diffuse to and be "captured" by a cell producing a different antibody. Thus in some cases, the methods require a high viscosity medium to reduce diffusion of the protein or antibody away from the expressing cell. Further, not all of the antibody produced by a hybridoma is actually captured on the cell surface and this excess antibody is secreted into the medium where it is readily available to bind to the capture molecule on other random hybridoma cells. Accordingly, new and/or improved methods for identifying and selecting cells producing antigen-specific monoclonal antibodies are needed.

SUMMARY OF THE INVENTION

The present invention describes novel polypeptides and cells comprising the polypeptides, as well as methods of using the polypeptides, cells and cells libraries to identify and/or select cells producing polypeptides. In particular, the methods may be used to identify and isolate cells producing antigen-specific monoclonal antibodies. The invention provides an approach wherein a membrane-bound heterodimeric molecule comprising a single antigen-binding site is expressed on the surface of the cell. The single antigen-binding site is representative of the binding specificity of the antibody produced by the cell. The heterodimeric molecule does not "bind" secreted antibody, so there are limited or no problems with antibody produced by one cell being bound or presented on the surface of another cell. The method and constructs as described herein are referred to as "Membrane-MAb" or "Membrane-MAb technique" and "Membrane-MAb constructs". The novel polypeptide constructs comprise a polypeptide comprising a dimerization domain and a transmembrane region from an immunoglobulin or non-immunoglobulin protein. In some embodiments, the novel polypeptide constructs comprise an immunoglobulin heavy chain constant region comprising CH2 and CH3 domains and a transmembrane region from an immunoglobulin or non-immunoglobulin protein. In some embodiments, the novel polypeptide constructs comprise an immunoglobulin heavy chain constant region comprising CH2 and CH3 domains and a GPI (glycosylphosphatidylinositol)-membrane anchor. When a cell expresses both the polypeptide and, for example, an immunoglobulin heavy chain, the polypeptides associate to produce a heterodimeric molecule comprising a monovalent antibody that is expressed on the surface of the cell. The heterodimeric molecule is not an antibody-binding protein and as such it does not bind or capture secreted antibody. A non-limiting example of the Membrane-MAb strategy is depicted in FIG. 1C. This is compared to a traditional hybridoma technique (FIG. 1A) and an example of a surface capture method (FIG. 1B).

In one aspect, the invention provides a polypeptide that is able to form a heterodimeric molecule with a second polypeptide, wherein first the polypeptide is membrane-bound and the heterodimeric molecule is expressed on the surface of a cell. In some embodiments, the polypeptide comprises (a) an extracellular portion comprising a dimerization domain, and (b) a transmembrane portion. In some embodiments, the dimerization domain may include, but is not limited to, a Fc region, an immunoglobulin constant region, a leucine zipper, or an isoleucine zipper. In some embodiments, the dimerization domain may be taken from a receptor, an integrin, or any molecule that normally forms a dimeric or mulitmeric structure. The dimerization domain may be taken from, for example, immunoglobulin, LFA-1, GPIIIb/IIIa), nerve growth factor (NGF), neurotrophin-3 (NT-3), interleukin-8 (IL-8), IL-8 receptor, vascular endothelial growth factor (VEGF), brain-derived neurotrophic factor (BDNF), Fos, Jun, NFkB, Ras, Raf, CD4, Bcl-2, Myc and Met.

In some embodiments, the polypeptide comprises (a) an extracellular portion comprising an immunoglobulin heavy chain constant region, and (b) a transmembrane portion. In some embodiments, the polypeptide comprises: (a) an extracellular portion comprising an immunoglobulin heavy chain constant region comprising CH2 and CH3 domains; and (b) a non-immunoglobulin transmembrane portion. In some embodiments, the immunoglobulin heavy chain constant region comprises at least a portion of a hinge region, CH2 and CH3 domains. In some embodiments, the immunoglobulin heavy chain constant region comprises a Fc region. In some embodiments, the immunoglobulin heavy chain constant region is from an IgG, IgA, IgD, IgE, or IgM antibody or a subtype thereof. In certain embodiments, the immunoglobulin heavy chain constant region is from an IgG1 or an IgG2 antibody. In some embodiments, the immunoglobulin heavy chain constant region is a mouse immunoglobulin heavy chain constant region. In some embodiments, the immunoglobulin heavy chain constant region is a human immunoglobulin heavy chain constant region. In some embodiments, the immunoglobulin heavy chain constant region comprises SEQ ID NO:2, SEQ ID NO:4, SEQ ID NO:6, or SEQ ID NO:8.

In some embodiments, the polypeptides of the present invention comprise a transmembrane portion. In some embodiments, the transmembrane portion comprises at least a portion of a transmembrane domain from an immunoglobulin or a non-immunoglobulin protein. In some embodiments, the transmembrane portion is from a human protein. In certain embodiments, the transmembrane portion is from a mouse protein. In some embodiments, the transmembrane portion is from a B-cell immunoglobulin protein. In some embodiments, the transmembrane portion is from a mouse B-cell immunoglobulin protein. In some embodiments, the transmembrane portion is from a human B-cell immunoglobulin protein. In some embodiments, the transmembrane portion is from a protein selected from the group consisting of: CD4, CD8, Class I MHC, Class II MHC, CD19, T-cell receptor α and β chains, CD3, zeta chain, ICAM1 (CD54), ICAM2, ICAM3, ICAM4, ICAM5, CD28, CD79a, CD79b, and CD2. In certain embodiments, the transmembrane portion is from a CD4 protein. In certain embodiments, the transmembrane portion is from a mouse CD4 protein. In certain embodiments, the transmembrane portion is from a human CD4 protein. In certain embodiments, the transmembrane portion comprises SEQ ID NO:13 or SEQ ID NO:16. In some embodiments, the transmembrane portion further comprises an intracellular domain (ICD). In some embodiments, the transmembrane portion comprises SEQ ID NO:14, SEQ ID NO:15, or SEQ ID NO:17.

In some embodiments, the polypeptides of the present invention comprise a GPI-membrane anchor. In some embodiments, the GPI-membrane anchor is obtained from a protein selected from the group consisting of CD52, CD55, CD58, and CD59.

In some embodiments, the polypeptides of the present invention comprise a detection or "reporter" molecule. In some embodiments, the detection or reporter molecule is a fluorescent protein, a bioluminescent protein, or a variant thereof. In certain embodiments, the detection or reporter molecule is green fluorescent protein (GFP) or a variant thereof.

Thus in some embodiments, the polypeptides of the present invention comprise an IgG CH2CH3 region and a transmembrane domain. In certain embodiments, the polypeptides comprise an IgG CH2CH3 constant region, a transmembrane domain, and GFP.

In some embodiments, the polypeptides of the present invention are membrane-bound and the immunoglobulin heavy chain constant region is expressed on the surface of the cell. In some embodiments, the polypeptide does not comprise an immunoglobulin heavy chain variable region. In certain embodiments, the polypeptide does not comprise an antigen-binding site. In some embodiments, the polypeptide is able to form a heterodimeric molecule with a second polypeptide. In certain embodiments, the second polypeptide comprises an immunoglobulin Fc region. In certain embodiments, the second polypeptide comprises an immunoglobulin heavy chain. In some embodiments, the second polypeptide further comprises an immunoglobulin light chain. In some embodiments, the second polypeptide comprises a single chain immunoglobulin with both an immunoglobulin heavy chain and an immunoglobulin light chain. In some embodiments, the polypeptide is able to form at least one disulfide bond with a second polypeptide.

In some embodiments, the polypeptide of the present invention comprises SEQ ID NO:10, SEQ ID NO:12, or SEQ ID NO:28. In some embodiments, the polypeptide of the present invention comprises SEQ ID NO:22, SEQ ID NO:23, or SEQ ID NO:26. In certain embodiments, the polypeptide of the present invention comprises SEQ ID NO:30, SEQ ID NO:31, or SEQ ID NO:32. In some embodiments, the polypeptide is encoded by a sequence comprising SEQ ID NO:9, SEQ ID NO:11, or SEQ ID NO:29. In some embodiments, the polypeptide is encoded by a sequence comprising SEQ ID NO:24, SEQ ID NO:25, or SEQ ID NO:27. In some embodiments, a host cell expresses any of the polypeptides described herein. In some embodiments, a host cell produces any of the polypeptides described herein.

In another aspect, the invention provides a heterodimeric polypeptide molecule. In some embodiments, the heterodimeric polypeptide molecule comprises (a) a first polypeptide comprising (i) an extracellular portion comprising a dimerization domain and (ii) a transmembrane portion, and (b) a second polypeptide comprising a dimerization domain. In some embodiments, the heterodimeric molecule comprises a first polypeptide comprising an immunoglobulin heavy chain. In some embodiments, the heterodimeric molecule comprises a second polypeptide comprising an immunoglobulin heavy chain. In some embodiments, the second polypeptide further comprises an immunoglobulin light chain. In some embodiments, the second polypeptide comprises a single chain immunoglobulin with both an immunoglobulin heavy chain and an immunoglobulin light chain. In some embodiments, the first polypeptide forms at least one disulfide bond with the second polypeptide.

In another aspect, the invention provides an antibody molecule comprising any of the polypeptides described herein. In some embodiments, the antibody molecule is a heterodimeric molecule. In certain embodiments, the antibody molecule further comprises: (a) an immunoglobulin heavy chain, and (b) an immunoglobulin light chain. In some embodiments, the antibody molecule further comprises a single chain immunoglobulin with an immunoglobulin heavy chain and an immunoglobulin light chain. In some embodiments, the polypeptide of the antibody molecule forms at least one disulfide bond with the Fc region of an immunoglobulin heavy chain-light chain pair. In some embodiments, the antibody molecule comprises a single antigen-binding site (e.g., is monovalent).

In one aspect, the invention provides a polynucleotide that encodes any of the polypeptides described herein. In some embodiments, the polynucleotide comprises SEQ ID NO:9, SEQ ID NO:11, or SEQ ID NO:29. In some embodiments, the polynucleotide comprises SEQ ID NO:24, SEQ ID NO:25, or SEQ ID NO:27. In some embodiments, a vector comprises the polynucleotide. In some embodiments, a host cell comprises the polynucleotide or vector. In some embodiments, a host cell comprises any of the polypeptides or antibody molecules described herein.

In one aspect, the invention provides host cells and methods of producing a host cell comprising the polypeptides described herein. In some embodiments, a method of producing a host cell comprises transfecting a cell with a polynucleotide that encodes a polypeptide comprising: (a) an extracellular portion comprising an immunoglobulin heavy chain constant region, and (b) a transmembrane portion. In some embodiments, the transfected cell expresses the polypeptide. In some embodiments, the cell is transiently transfected. In other embodiments, the cell is stably transfected. In some embodiments, the method further comprises detecting expression of the polypeptide. In some embodiments, the method further comprises detecting expression of the polypeptide on the surface of the cell. In other embodiments, the method further comprises isolating a cell that expresses the polypeptide on the surface of the cell. In some embodiments, the cell is a mammalian cell (e.g., a human or mouse cell). In some embodiments, the cell is a fusion partner cell line.

In some embodiments, the invention provides host cells produced by the methods described herein. In some embodiments, the cells comprise a polynucleotide that encodes any of the polypeptides described herein. In some embodiments, the cells comprise any of the polypeptides described herein. In certain embodiments, the cells express a polypeptide, wherein the polypeptide comprises: (a) an extracellular portion comprising an immunoglobulin heavy chain constant region, and (b) a transmembrane portion.

In another aspect, the cells of the present invention may be used to produce membrane-bound heterodimeric molecules. In some embodiments, a cell comprises: (a) a polynucleotide that encodes a membrane-bound polypeptide comprising: (i) an extracellular portion comprising an immunoglobulin heavy chain constant region, and (ii) a transmembrane portion; and (b) at least one additional polynucleotide that encodes at least one additional polypeptide. In some embodiments, the additional polypeptide comprises an immunoglobulin heavy chain constant region comprising CH2 and CH3 domains. In some embodiments, the additional polypeptide comprises a Fc domain. In some embodiments, the additional polypeptide comprises an immunoglobulin heavy chain and/or light chain. In some embodiments, the additional polypeptide comprises an antibody. In some embodiments, the additional polypeptide comprises a single chain antibody. In some embodiments, the at least one additional polypeptide comprises randomized polypeptides. In some embodiments, the at least one additional polypeptide comprises mutagenized polypeptides. In some embodiments, the at least one additional polypeptide comprises a library of polypeptides. In some embodiments, the additional polypeptides are secreted from the cell. In other embodiments, the membrane-bound polypeptide forms at least one disulfide bond with the additional polypeptide to form a membrane-bound heterodimeric molecule.

In one aspect, the invention provides methods of producing a hybridoma cell that expresses a membrane-bound heterodimeric molecule on the surface of the cell. In some embodiments, a method of producing a hybridoma cell comprises fusing cells with an antibody-producing cell, wherein the cells comprise a polynucleotide that encodes a membrane-bound polypeptide comprising: (a) an extracellular portion comprising an immunoglobulin heavy chain constant region, and (b) a transmembrane portion. In some embodiments, the fused hybridoma cells express a heterodimeric antibody molecule on the surface of the cells. In some embodiments, the antibody-producing cell is a population of antibody-producing cells. In some embodiments, the antibody-producing cell is from a naive animal. In some embodiments, the antibody-producing cell is from an immunized animal. In some embodiments, the antibody-producing cell includes, but is not limited to, a B-cell, a plasma cell, a hybridoma, a myeloma, and a recombinant cell. In some embodiments, the antibody-producing cell comprises a plurality of polynucleotides. In some embodiments, the plurality of polynucleotides encodes a plurality of polypeptides. In some embodiments, the plurality of polypeptides comprises immunoglobulin heavy chain constant regions. In some embodiments, the plurality of polypeptides comprises immunoglobulin heavy chains, and/or immunoglobulin light chains. In some embodiments, the plurality of polypeptides comprises a single chain immunoglobulin with an immunoglobulin heavy chain and an immunoglobulin light chain. In some embodiments, the plurality of polypeptides comprises a randomized polypeptide library. In some embodiments, the plurality of polynucleotides comprises a DNA library. In some embodiments, the DNA library is generated from cells of a naïve animal. In some embodiments, the DNA library is generated from cells of an immunized animal. In some embodiments, the DNA library is a cDNA library. In some embodiments, the fused cells comprise a population of hybridoma cells that express a plurality of heterodimeric antibody molecules.

In one aspect, the invention provides a hybridoma or hybridoma library made by any of the methods described herein.

In another aspect, the invention provides cell libraries and methods of producing cell libraries comprising the polypeptides described herein. In some embodiments, a method of producing a cell library comprises transfecting cells with a plurality of polynucleotides, wherein the cells comprise a polynucleotide that encodes a polypeptide comprising (a) an extracellular portion comprising an immunoglobulin heavy chain constant region, and (b) a transmembrane portion. In some embodiments, the transfected cells express a heterodimeric molecule on the surface of a plurality of the transfected cells. In some embodiments, the plurality of polynucleotides encodes a plurality of polypeptides. In some embodiments, each polypeptide of the plurality of polypeptides comprises an immunoglobulin Fc region. In some embodiments, the plurality of polypeptides comprises a plurality of randomized polypeptides. In some embodiments, each polypeptide of the plurality of polypeptides comprises: (a) an immunoglobulin Fc region, and (b) a randomized polypeptide. In other embodiments, the plurality of polypeptides comprises immunoglobulin heavy chains, and/or immunoglobulin light chains. In other embodiments, the plurality of polypeptides comprises a single chain immunoglobulin with an immunoglobulin heavy chain and an immunoglobulin light chain. In some embodiments, the plurality of polynucleotides comprises a DNA library. In some embodiments, the DNA library is generated from cells of a naïve animal. In some embodiments, the DNA library is generated from cells of an immunized animal. In other embodiments, the DNA library encodes a plurality of randomized polypeptides. In other embodiments, the DNA library encodes a plurality of polypeptides, wherein each polypeptide comprises: (a) an immunoglobulin Fc region, and (b) a randomized polypeptide.

In one aspect, the invention provides a cell library made by any of the methods described herein.

In another aspect, the invention provides methods of identifying a cell that is producing a specific antibody. In some embodiments, a method of identifying a cell that produces a specific antibody comprises fusing cells with an antibody-producing cell to produce a population of hybridoma cells, wherein the cells comprise a polypeptide comprising (a) an extracellular portion comprising an immunoglobulin heavy chain constant region, and (b) a transmembrane portion. In some embodiments, the hybridoma cells express a heterodimeric molecule on the surface of the cells. In some embodiments, the method comprises contacting the population of hybridoma cells with a detection molecule (e.g., a target of interest). In some embodiments, the method comprises identifying the hybridoma cells that are bound by the detection molecule. In some embodiments, the method comprises isolating the cells that are bound by the detection molecule. In some embodiments, the antibody-producing cells are from a naïve animal. In some embodiments, the antibody-producing cells are from an immunized animal. In some embodiments, the antibody-producing cells are human cells. In some embodiments, the antibody-producing cells are mouse cells. In certain embodiments, the antibody-producing cell is a B-cell, a plasma cell, a hybridoma, a myeloma, or a recombinant cell. In some embodiments, the antibody-producing cell comprises a plurality of polypeptides. In some embodiments, the antibody-producing cell comprises a plurality of polynucleotides. In some embodiments, the plurality of polynucleotides encodes a plurality of polypeptides comprising immunoglobulin heavy chains, and/or immunoglobulin light chains. In some embodiments, the plurality of polynucleotides encodes a plurality of polypeptides comprising a single chain immunoglobulin with an immunoglobulin heavy chain and an immunoglobulin light chain. In other embodiments, the plurality of polynucleotides comprises a DNA library. In some embodiments, the DNA library is generated from cells of a naïve animal. In some embodiments, the DNA library is generated from cells of an immunized animal.

In some embodiments, the antibody made by the antibody-producing cells is a recombinant antibody, a monoclonal antibody, a chimeric antibody, a humanized antibody, a human antibody, or an antibody fragment. In some embodiments, the antibody made by the antibody-producing cell is an IgA, IgD, IgE, IgG or IgM antibody or a subtype thereof.

In some embodiments, the detection molecule (e.g., a target of interest) is a protein or a fragment thereof. In some embodiments, the detection molecule is an antigen of interest. In some embodiments, the detection molecule is labeled. In certain embodiments, the cells bound by the detection molecule are identified by flow cytometry. In some embodiments, the cells bound by the detection molecule are isolated by fluorescence-activated cell sorting (FACS).

In some embodiments, the method of identifying a cell that produces a specific antibody comprises transfecting cells with at least one polynucleotide, wherein the cells comprise a polypeptide comprising (a) an extracellular portion comprising an immunoglobulin heavy chain constant region, and (b) a transmembrane portion. In some embodiments, the transfected cells express a heterodimeric molecule on the surface of the cells. In some embodiments, the method comprises contacting the transfected cells with a detection molecule (e.g., a target of interest). In some embodiments, the method comprises identifying the cells that are bound by the detection molecule. In some embodiments, the method comprises isolating the cells that are bound by the detection molecule. In some embodiments, the at least one polynucleotide comprises a plurality of polynucleotides. In some embodiments, the plurality of polynucleotides encodes a plurality of polypeptides comprising immunoglobulin heavy chains, and/or immunoglobulin light chains. In other embodiments, the plurality of polynucleotides comprises a DNA library. In some embodiments, the DNA library is generated from cells of a naïve animal. In some embodiments, the DNA library is generated from cells of an immunized animal.

In some embodiments, the at least one polynucleotide encodes for a polypeptide that is a recombinant antibody, a monoclonal antibody, a chimeric antibody, a humanized antibody, a human antibody, or an antibody fragment. In some embodiments, the at least one polynucleotide encodes for a polypeptide that is an IgA, IgD, IgE, IgG or IgM antibody or a sub-type thereof.

In some embodiments, the detection molecule (e.g., a target of interest) is a protein or fragment thereof. In some embodiments, the detection molecule is an antigen of interest. In some embodiments, the detection molecule is labeled. In certain embodiments, the cells bound by the detection molecule are identified by flow cytometry. In some embodiments, the cells bound by the detection molecule are isolated by FACS.

In some embodiments, the method of identifying a cell that produces a specific antibody comprises transfecting a cell library with a polynucleotide encoding a polypeptide comprising (a) an extracellular portion comprising an immunoglobulin heavy chain constant region, and (b) a transmembrane portion, wherein the cell library comprises antibody-producing cells. In some embodiments, the transfected cells express a heterodimeric molecule on the surface of the cells. In some embodiments, the method comprises contacting the transfected cells with a detection molecule (e.g., a target of interest). In some embodiments, the method comprises identifying the cells that are bound by the detection molecule. In some embodiments, the method comprises isolating the cells that are bound by the detection molecule. In some embodiments, the cell library is a hybridoma library. In some embodiments, the cell library comprises cells are from a naïve animal. In some embodiments, the cell library comprises cells are from an immunized animal. In some embodiments, the cell library comprises human cells. In some embodiments, the cell library comprises mouse cells. In certain embodiments, the cell library comprises B-cells, plasma cells, hybridomas, myelomas, or recombinant cells. In some embodiments, the cell library comprises a plurality of polypeptides. In some embodiments, the cell library comprises a plurality of polynucleotides. In some embodiments, the plurality of polynucleotides encodes a plurality of polypeptides comprising immunoglobulin heavy chains, and/or immunoglobulin light chains. In some embodiments, the plurality of polynucleotides encodes a plurality of polypeptides comprising a single chain immunoglobulin with an immunoglobulin heavy chain and an immunoglobulin light chain. In other embodiments, the plurality of polynucleotides comprises a DNA library. In some embodiments, the DNA library is generated from cells of a naïve animal. In some embodiments, the DNA library is generated from cells of an immunized animal.

In some embodiments, the antibody made by the cell library is a recombinant antibody, a monoclonal antibody, a chimeric antibody, a humanized antibody, a human antibody, or an antibody fragment. In some embodiments, the antibody made by the cell library is an IgA, IgD, IgE, IgG or IgM antibody or a subtype thereof.

In some embodiments, the detection molecule is a protein or fragment thereof. In some embodiments, the detection molecule is an antigen of interest. In some embodiments, the detection molecule is labeled. In certain embodiments, the cells bound by the detection molecule are identified by flow cytometry. In some embodiments, the cells bound by the detection molecule are isolated by FACS.

In one aspect, the present invention provides a cell library, each cell comprising: (a) a first polypeptide comprising any of the membrane-bound polypeptides described herein, and (b) a second polypeptide comprising an immunoglobulin heavy chain. In some embodiments, the two polypeptides are able to form a heterodimeric molecule. In some embodiments, the heterodimeric molecule is expressed on the surface of the cell. In some embodiments, each cell further comprises an immunoglobulin light chain. In some embodiments, the second polypeptide comprises a single chain immunoglobulin with an immunoglobulin heavy chain and an immunoglobulin light chain. In some embodiments, the heterodimeric molecule comprises a single antigen-binding site.

In some embodiments, the present invention provides a cell library, each cell comprising: (a) a first polypeptide comprising any of the membrane-bound polypeptides described herein, and (b) a second polypeptide comprising an immunoglobulin heavy chain constant region comprising CH2 and CH3 domains. In some embodiments, the two polypeptides are able to form a heterodimeric molecule. In some embodiments, the heterodimeric molecule is expressed on the surface of the cell. In some embodiments, the second polypeptide comprises an immunoglobulin Fc region. In some embodiments, the second polypeptide comprises: (a) an immunoglobulin Fc region, and (b) a randomized polypeptide. In some embodiments, the second polypeptide comprises: (a) a region that is able to form disulfide bonds, and (b) a randomized polypeptide. In some embodiments, the second polypeptide comprises: (a) a region that is able to form disulfide bonds, and (b) a mutagenized polypeptide.

In another aspect, the present invention provides methods for screening any of the cell libraries described herein. In some embodiments, the method of screening a cell library comprises contacting the cell library with a detection molecule (e.g., a target of interest). In some embodiments, the method comprises identifying the cells that are bound by the detection molecule. In some embodiments, the method comprises isolating the cells that are bound by the detection molecule. In some embodiments, the detection molecule is a protein or fragment thereof. In some embodiments, the detection molecule is an antigen of interest. In some embodiments, the detection molecule is a small molecule compound. In certain embodiments, the detection molecule is labeled. In some embodiments, the cells are identified by flow cytometry. In certain embodiments, the cells are isolated by FACS.

In another aspect, the present invention provides methods of screening for antibodies. In some embodiments, the method of screening for a specific antibody comprises contacting the cells or cell libraries described herein with a detection molecule (e.g., a target of interest). In some embodiments, the method of screening for a specific antibody comprises identifying the cells that are bound by the detection molecule. In some embodiments, the method for screening for a specific antibody comprises isolating the cells that are bound by the detection molecule. In some embodiments, the method for screening for a specific antibody comprises isolating the antibody from the cells identified by the detection molecule. In some embodiments, the detection molecule is a protein or fragment thereof. In some embodiments, the detection molecule is an antigen of interest. In some embodiments, the detection molecule is a small molecule compound. In certain embodiments, the detection molecule is labeled. In some embodiments, the cells are identified by flow cytometry. In certain embodiments, the cells are isolated by FACS.

In another aspect, the present invention provides antibodies produced, identified, and/or isolated by any of the methods described herein.

BRIEF DESCRIPTIONS OF THE DRAWINGS

FIG. 1A. Schematic of the Membrane-MAb technique compared with other hybridoma strategies.

FIG. 1A depicts a typical hybridoma indicating that monoclonal antibody is secreted from the hybridoma.

FIG. 1B depicts a hybridoma that expresses an antibody-binding protein or "capture protein" (e.g., an Fc receptor or protein A) on its cell surface. The schematic indicates that monoclonal antibody is secreted from the hybridoma. However, the hybridoma has an antibody-binding protein on the cell surface that can bind antibody, i.e., antibody secreted by the cell but also antibody produced by other cells.

FIG. 1C depicts one non-limiting embodiment of the Membrane-MAb strategy. The hybridoma expresses a heterodimeric molecule that comprises a membrane-bound polypeptide covalently associated with an immunoglobulin heavy chain-light chain pair. The immunoglobulin heavy chain-light chain pair forms a single antigen-binding site representative of the monoclonal antibody produced by the cell.

FIG. 2A. Generation of a cell expressing a Membrane-MAb polypeptide for use in fusions. The murine hybridoma fusion partner cell line SP2/0-Ag14 was stably transfected with the Membrane-MAb(mIgG1) construct. The resulting cell line was designated SP2/0-MT. FIG. 2A shows flow cytometry results for cell surface expression of the Membrane-MAb(mIgG1) construct on the SP2/0-MT cells using an isotype negative control antibody (left panel) and an anti-FLAG antibody (right panel). The Membrane-MAb (mIgG1) construct has a FLAG tag allowing the polypeptide to be detected by the anti-FLAG antibody.

FIG. 2B shows flow cytometry results for cell surface expression of the Membrane-MAb(mIgG1) construct on five subclones of the SP2/0-MT cell line.

FIG. 3. Use of the Membrane-MAb technique to identify hybridomas producing an antibody that binds multiple targets. Shown is a flow cytometry plot of a Membrane-MAb hybridoma library prepared by fusion of SP-2/0 cells with cells isolated from mice immunized with murine FZD5 and FZD8. The cells were incubated with labeled FZD5 and FZD8 proteins and analyzed. Recombinant FZD5 protein was labeled with Alexa Fluor 488 and recombinant FZD8 protein was labeled with Alexa Fluor 647. Hybridoma cells that display binding to both FZD5 and FZD8 were identified. (In the boxed area labeled "FZD5/8 DP"; DP=double positive).

FIG. 4. Use of the Membrane-MAb technique to identify cells producing antibodies to DDR2. Shown is a flow cytometry plot of a Membrane-MAb hybridoma library prepared by transfection of the Membrane-MAb(mIgG1) construct into an existing DDR2 hybridoma library. The cells were incubated with labeled DDR2 protein and an anti-FLAG antibody and analyzed. Recombinant DDR2 protein was labeled with Alexa Fluor 488 and the anti-FLAG antibody was labeled with phycoerythrin (PE). In the boxed area labeled "DDR2 Pos" are hybridoma cells that display binding to DDR2 and the anti-FLAG antibody.

FIG. 5A. Flow cytometry analysis of 293-hMT stable clones. HEK-293 cells were stably transfected with the Membrane-MAb(hIgG2)-GFP construct. 14 clones were screened for GFP expression. FIG. 5A depicts a flow cytometry analysis for clones 4-9.

FIG. 5B. Flow cytometry analysis of 293-hMT stable clones. HEK-293 cells were stably transfected with the Membrane-MAb(hIgG2)-GFP construct. 14 clones were screened for GFP expression. FIG. 5B depicts a flow cytometry analysis for clones 10-14.

FIG. 6A. Schematic of cell-based antibody display using Membrane-MAb construct. FIG. 6A depicts the Membrane-MAb(hIgG2) and Membrane-MAb(hIgG2)-GFP constructs.

FIG. 6B depicts a single chain antibody vector referred to herein as MAbLib construct. To facilitate generation of antibody libraries, the heavy chain variable region and the light chain variable region are flanked by unique restriction sites.

FIG. 6C depicts the Membrane-MAb(hIgG2)-GFP molecule expressed on the surface of in HEK-293 cells.

FIG. 6D depicts a non-limiting embodiment of a heterodimeric molecule on the surface of HEK-293 cells. The heterodimeric molecule is a Membrane-MAb(hIgG2)-GFP protein associated with a single chain antibody molecule.

FIG. 7. Analysis of expression of heterodimeric antibody molecules on the surface of HEK-293 cells. Various concentrations of anti-DLL4 antibody sc21M18 plasmid DNA were used to transfect HEK-293 cells in combination with the Membrane-MAb(hIgG2)-GFP construct (-X-). Controls were non-transfected cells (-♦-), cells transfected with sc21M18 DNA only (-▲-), and cells transfected with Membrane-MAb(hIgG2)-GFP DNA only (-■-). Cells were incubated for 48 hours, harvested, and screened with an antibody specific antigen (hDLL4-Fc) by FACS. Results are shown as mean fluorescence intensities (MFI).

FIG. 8. Analysis of the use of carrier plasmid to modulate display of the antibody molecule. Anti-DLL4 antibody plasmid DNA was mixed with an excess of an irrelevant antibody plasmid DNA (sc18R5) at various ratios and used to transfect HEK-293 cells. Cells were incubated for 48 hours, harvested, and screened by FACS. For screening of anti-DLL4 antibody on the surface, hDLL4-rFc was used as antigen (-♦-) and hJag-rFc protein was used as a control (-■-). Bound antigen was detected with a PE-labeled anti-rabbit Fc antibody and was also used alone as a control (-▲-). The percentage of cells expressing anti-DLL4 antibody on the surface was determined by FACS.

Figure 9A:
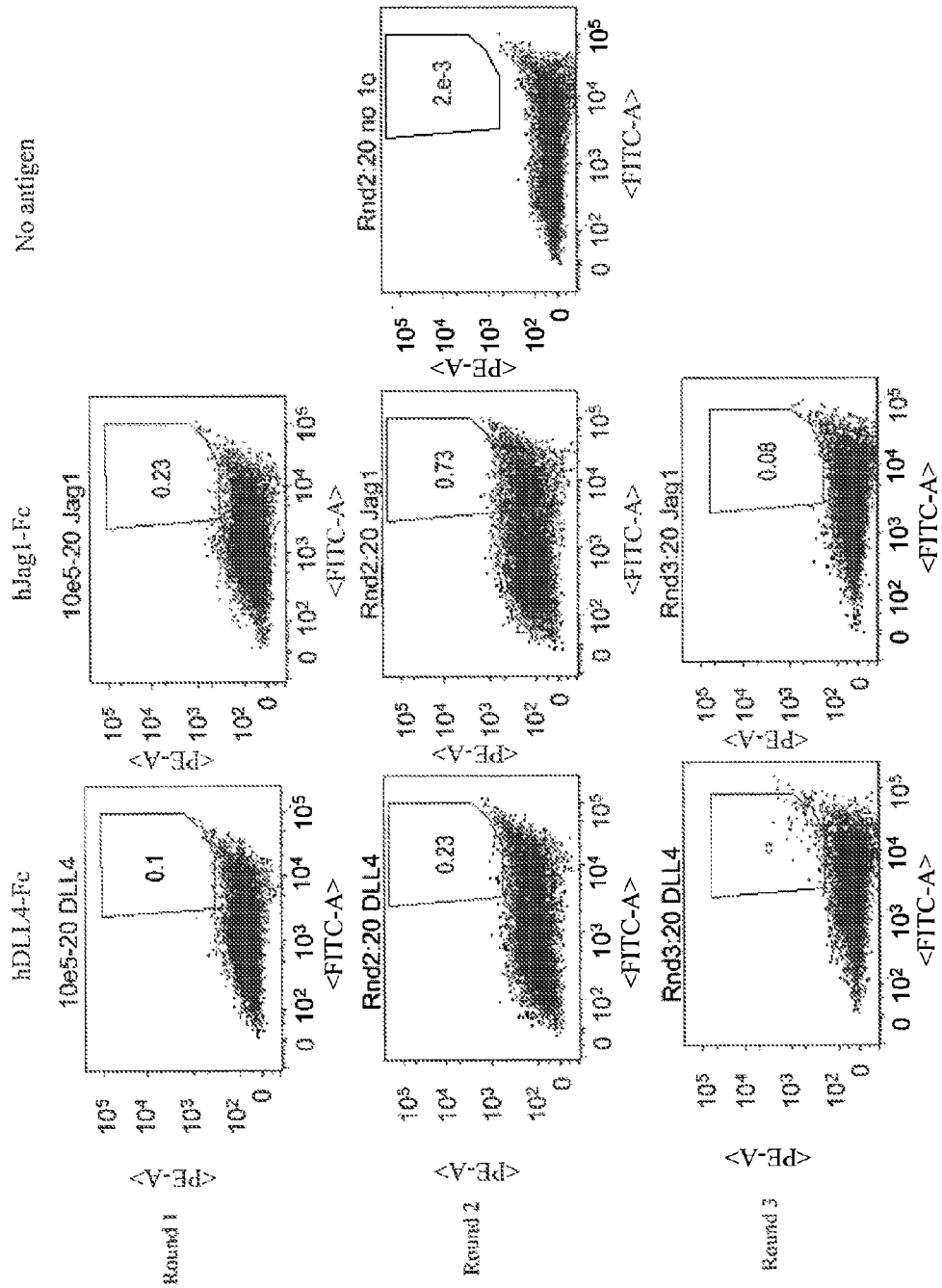

FIG. 9A. Selection and enrichment of cells expressing anti-DLL4 antibody. HEK-293 cells were transfected with a mixture of anti-DLL4 antibody plasmid DNA and irrelevant antibody plasmid DNA at a ratio of 1:100,000 (sc21M18: sc18R5). Cells were subjected to 4 rounds of sorting and at each round the percentage of cells expressing anti-DLL4 antibody on the surface was determined by FACS. FIG. 9A depicts rounds 1-3.

Figure 9B:
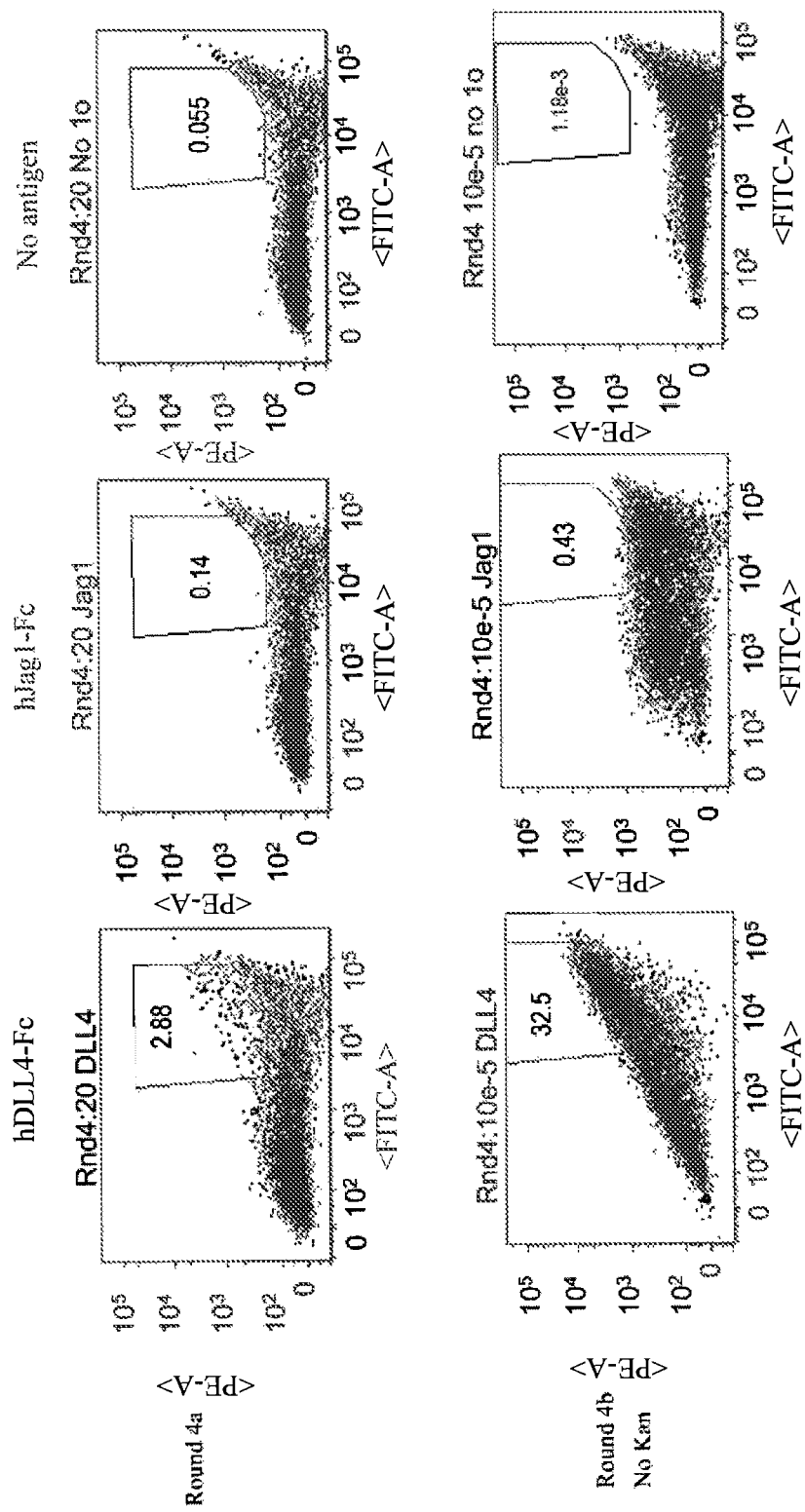

FIG. 9B. Selection and enrichment of cells expressing anti-DLL4 antibody. HEK-293 cells were transfected with a mixture of anti-DLL4 antibody plasmid DNA and irrelevant antibody plasmid DNA at a ratio of 1:100,000 (sc21M18: sc18R5). Cells were subjected to 4 rounds of sorting and at each round the percentage of cells expressing anti-DLL4 antibody on the surface was determined by FACS. FIG. 9B depicts rounds 4a and 4b.

DETAILED DESCRIPTION

The present invention provides novel membrane-bound polypeptides, including polypeptides that are able to form heterodimeric molecules on the surface of cells. Related polypeptides and polynucleotides, as well as cells and cell libraries comprising the polypeptides and polynucleotides are also provided. Methods of producing host cells comprising the polypeptides and using these cells to identify and isolate specific individual cells are further provided. Antibodies produced by the cells, or produced, isolated, and/or identified by the methods are also provided.

Constructs comprising nucleotides encoding for novel membrane-bound polypeptides, including Membrane-Mab (mIgG1), Membrane-Mab(hIgG2), and Membrane-Mab (hIgG2)-GFP were generated (Example 1). Cells that express the novel membrane-bound polypeptides were produced. The cell line SP2/0-MT was generated by transfecting the Membrane-Mab(mIgG1) construct into SP2/0-Ag14 cells, a murine fusion partner cell line (Example 2). The cell line 293-hMT was generated by transfecting the Membrane-Mab(hIgG2)-GFP construct into HEK-293 cells, a human embryonic kidney-derived cell line (Example 5). SP2/0-MT cells were used in a fusion with cells from an immunized animal to produce a hybridoma library expressing heterodimeric antibody molecules on the cell surface. These membrane-bound antibody molecules were used to detect and isolate cells producing antibodies that specifically bound to the target antigens (Example 3). A polynucleotide encoding the novel polypeptide Membrane-Mab(mIgG1) was transfected into an established hybridoma library and the resulting cells were shown to express a heterodimeric antibody molecule on their surface. The membrane-bound antibody molecules were used to detect and isolate cells producing antibodies that specifically bound to the target antigen (Example 4). Using both a hybridoma fusion method and a transfection method, the Membrane-MAb technique resulted in a dramatic increase in the percentage of antigen-specific positive clones isolated (91% and 84% positive) as compared to randomly selected clones (0.6% and 8% positive). The Membrane-Mab(hIgG2)-GFP construct was transfected into HEK-293 cells with DNA encoding an anti-DLL4 antibody. Analysis by flow cytometry demonstrated the presence of a heterodimeric molecule on the surface of the transfected cells which bound DLL4 antigen (Example 7). A validation study using the Membrane MAb technique demonstrated that cells expressing a heterodimeric molecule comprising an anti-DLL4 antibody could be selected out of a population of cells wherein a different antibody was expressed in large excess (Example 9).

I. Definitions

To facilitate an understanding of the present invention, a number of terms and phrases are defined below.

The term "antibody" as used herein refers to an immunoglobulin molecule that recognizes and specifically binds to a target, such as a protein, polypeptide, peptide, carbohydrate, polynucleotide, lipid, or combinations of the foregoing through at least one antigen recognition site or antigen-binding site within the variable region of the immunoglobulin molecule. As used herein, the term "antibody" encompasses intact polyclonal antibodies, intact monoclonal antibodies, antibody fragments (such as Fab, Fab', F(ab')2, and Fv fragments), single chain Fv (scFv) mutants, single chain immunoglobulin molecules which include an immunoglobulin heavy chain and an immunoglobulin light chain in their entirety, multispecific antibodies such as bispecific antibodies generated from at least two intact antibodies, chimeric antibodies, humanized antibodies, human antibodies, fusion proteins comprising an antigen recognition site of an antibody, and any other modified immunoglobulin molecule comprising an antigen recognition site so long as the antibody exhibits the desired biological activity. In addition, the term "antibody" includes monovalent antibody molecules that have only one binding site. An antibody can be any of the five major classes of immunoglobulins: IgA, IgD, IgE, IgG, and IgM, or sub-classes thereof (e.g., IgG1, IgG2, IgG3, IgG4, IgA1 and IgA2), based on the identity of their heavy chain constant domains referred to as alpha, delta, epsilon, gamma, and mu, respectively.

The term "Fc region" as used herein refers to a C-terminal region of an immunoglobulin heavy chain. The "Fc region" may be a native sequence Fc region or a variant Fc region. Although the boundaries of the Fc region of an immunoglobulin heavy chain may vary, the Fc region of an immunoglobulin generally comprises two constant domains, CH2 and CH3, and at least a portion of the hinge region.

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

The term "variable region" of an antibody refers to the variable region of the antibody light chain or the variable region of the antibody heavy chain, either alone or in combination. The variable regions of the heavy and light chains each consist of four framework regions connected by three complementarity determining regions (CDRs), also known as "hypervariable regions". The CDRs in each chain are held together in close proximity by the framework regions and, with the CDRs from the other chain, contribute to the formation of the antigen-binding site of the antibody. There are at least two techniques for determining CDRs: (1) an approach based on cross-species sequence variability (i.e., Kabat et al., 1991, *Sequences of Proteins of Immunological Interest*, 5th Ed., National Institutes of Health, Bethesda Md.); and (2) an approach based on crystallographic studies of antigen-antibody complexes (Al-Lazikani et al., 1997, *J. Molec. Biol.* 273:927-948). In addition, combinations of these two approaches can be used in the art to determine CDRs.

The term "monoclonal antibody" refers to a homogeneous antibody population involved in the highly specific recognition and binding of a single antigenic determinant or epitope. This is in contrast to polyclonal antibodies that typically include a mixture of different antibodies directed against different antigenic determinants. The term "monoclonal antibody" encompasses both intact and full-length monoclonal antibodies as well as antibody fragments (such as Fab, Fab', F(ab')2, Fv fragments), scFv variants, fusion proteins comprising an antibody portion, and any other modified immunoglobulin molecule comprising an antigen recognition site. "Monoclonal antibody" refers to such antibodies made by any number of techniques including, but not limited to, hybridoma production, phage selection, recombinant expression, and transgenic animals.

The term "humanized antibody" refers to forms of non-human (e.g., murine) antibodies that are specific immunoglobulin chains, chimeric immunoglobulins, or fragments thereof that contain minimal non-human (e.g., murine) sequences.

The term "human antibody" refers to an antibody produced by a human or an antibody having an amino acid sequence corresponding to an antibody produced by a human made using any technique known in the art. This definition of a human antibody includes intact or full-length antibodies, fragments thereof, and/or antibodies comprising at least one human heavy and/or light chain polypeptide such as, for example, an antibody comprising a murine light chain polypeptide and a human heavy chain polypeptide.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammal (e.g., mouse, rat, rabbit) with the desired specificity, affinity, and/or capability while the constant regions are homologous to the sequences in antibodies derived from another species (usually human) to avoid eliciting an immune response in that species.

The terms "epitope" and "antigenic determinant" are used interchangeably herein and refer to that portion of an antigen capable of being recognized and specifically bound by a particular antibody. When the antigen is a polypeptide, epitopes can be formed both from contiguous amino acids (often referred to as "linear epitopes") and noncontiguous amino acids juxtaposed by tertiary folding of a protein (often referred to as "conformation epitopes"). Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

The term "non-immunoglobulin" as used herein refers to polypeptides that are not an antibody immunoglobulin chain. As used herein "non-immunoglobulin" encompasses other members of the immunoglobulin superfamily.

The terms "specifically binds" and "specific binding" mean that a binding agent or an antibody reacts or associates more frequently, more rapidly, with greater duration, with greater affinity, or with some combination of the above to an epitope or protein than with alternative substances, including unrelated proteins. In certain embodiments, "specifically binds" means, for instance, that an antibody binds to a protein with a $K_D$ of about 0.1 mM or less, but more usually less than about 1 µM. In certain embodiments, "specifically binds" means that an antibody binds to a protein with a $K_D$ of at least about 0.1 µM or less, at least about 0.01 µM or less, or at least about 1 nM or less. Because of the sequence identity between homologous proteins in different species, specific binding can include an antibody that recognizes a particular protein in more than one species (e.g., a mouse FZD and a human FZD). Likewise, because of homology between different proteins in certain regions of the polypeptide sequences, specific binding can include an antibody (or other polypeptide or agent) that recognizes more than one protein (e.g., human FZD5 and human FZD8). It is understood that an antibody or binding moiety that specifically binds to a first target may or may not specifically bind to a second target. As such, "specific binding" does not necessarily require (although it can include) exclusive binding, i.e. binding to a single target. Thus, an antibody may, in certain embodiments, specifically bind to more than one target. In certain embodiments, the multiple targets may be bound by the same antigen-binding site on the antibody. For example, an antibody may, in certain instances, comprise two identical antigen-binding sites, each of which specifically binds the same epitope on two or more proteins. Generally, but not necessarily, reference to binding means specific binding.

The terms "polypeptide" and "peptide" and "protein" are used interchangeably herein and refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids), as well as other modifications known in the art. It is understood that, because at least some of the polypeptides of this invention are based upon antibodies, in certain embodiments, the polypeptides can occur as single chains or associated chains.

The terms "polynucleotide" and "nucleic acid," are used interchangeably herein and refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polynucleotide. The sequence of nucleotides may be interrupted by non-nucleotide components. A polynucleotide may be further modified after assembly, such as by conjugation with a labeling component.

"Conditions of high stringency" may be identified by those that: (1) employ low ionic strength and high temperature for washing, for example, 0.015M sodium chloride/0.0015M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75M NaCl, 0.075M sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C.

The terms "identical" or "percent identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The "percent identity" may be measured using sequence comparison software or algorithms or by visual inspection. Various algorithms and software that may be used to obtain alignments of amino acid or nucleotide sequences are well-known to those of skill in the art. These include, but are not limited to, BLAST, ALIGN, Megalign, BestFit, and GCG Program. In some embodiments, two nucleic acids or polypeptides of the invention are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. In some embodiments, identity exists over a region of the sequences that is at least about 10, at least about 20, at least about 40-60, at least about 60-80 residues in length or any integral value therebetween. In some embodiments, identity exists over a longer region than 60-80 residues, such as at least about 90-100 residues, and in some embodiments the sequences are substantially identical over the full length of the sequences being compared, such as the coding region of a nucleotide sequence.

A "conservative amino acid substitution" is one in which one amino acid residue is replaced with another amino acid residue having a similar side chain Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is considered a conservative substitution. Preferably, conservative substitutions in the sequences of the polypeptides and antibodies of the invention do not abrogate the binding of the polypeptide or antibody containing the amino acid sequence, to the antigen(s), i.e., the one or more proteins to which the polypeptide or antibody binds. Methods of identifying nucleotide and amino acid conservative substitutions that do not eliminate antigen binding are well-known in the art.

The term "vector" refers to a construct that is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, and DNA or RNA expression vectors encapsulated in liposomes.

As used herein the term "transfection" is used to refer to the uptake of foreign DNA by a cell. A cell has been "transfected" when exogenous DNA has been introduced inside the cell membrane.

A polypeptide, antibody, polynucleotide, vector, cell, or composition that is "isolated" is a polypeptide, antibody, polynucleotide, vector, cell, or composition that is in a form not found in nature. Isolated polypeptides, antibodies, polynucleotides, vectors, cells or compositions include those that have been purified to a degree that they are no longer in a form in which they are found in nature. In some embodiments, an antibody, polynucleotide, vector, cell, or composition that is isolated is substantially pure.

As used herein, "substantially pure" refers to material that is at least 50% pure (i.e., free from contaminants), more preferably at least 90% pure, more preferably at least 95% pure, more preferably at least 98% pure, more preferably at least 99% pure.

As used herein, "animal" refers to any animal (e.g., a mammal) including, but not limited to, mice, rats, hamsters, other rodents, rabbits, goats, canines, felines, non-human primates, humans, and the like.

The term "and/or" as used in a phrase such as "A and/or B" herein is intended to include both A and B; A or B; A (alone) and B (alone).

As used in the present disclosure and claims, the singular forms "a" "an" and "the" include plural forms unless the context clearly dictates otherwise.

It is understood that wherever embodiments are described herein with the language "comprising" otherwise analogous embodiments described in terms of "consisting of" and/or "consisting essentially of" are also provided.

II. Polypeptides and Polynucleotides

The present invention provides novel polypeptides that are membrane-bound and which comprise an extracellular portion expressed on the surface of cells. In some embodiments, the polypeptide comprises: (a) an extracellular portion comprising a dimerization domain, and (b) a transmembrane portion. As used herein, a dimerization domain is any domain that can facilitate interaction between two polypeptides. Suitable dimerization domains include those of proteins having amphipathic alpha helices in which hydrophobic residues are regularly spaced and allow the formation of a dimer by interaction of the hydrophobic residues of each protein. Suitable dimerization domains include those of proteins having cysteine residues that allow the formation of a dimer through formation of disulfide bonds. Dimerization domains may include, but are not limited to, immunoglobulin constant regions, leucine zippers, isoleucine zippers, and GCN4 zippers. In some embodiments, the polypeptide comprises: (a) an extracellular portion comprising an immunoglobulin heavy chain constant region, and (b) a transmembrane portion. In some embodiments, the polypeptide comprises: (a) an extracellular portion comprising a dimerization domain, and (b) a GPI-anchored portion. In some embodiments, the polypeptide comprises: (a) an extracellular portion comprising an immunoglobulin heavy chain constant region, and (b) a GPI-anchored portion. In some embodiments, the immunoglobulin heavy chain constant region comprises at least one constant domain selected from CH2, CH3, and/or CH4. In some embodiments, the immunoglobulin heavy chain constant region comprises at least a portion of a hinge region. In some embodiments, the immunoglobulin heavy chain constant region comprises CH2 and CH3 domains. In some embodiments, the immunoglobulin heavy chain constant region comprises a hinge region, CH2 and CH3. In some embodiments, the immunoglobulin heavy chain constant region comprises a Fc region. In some embodiments, the immunoglobulin heavy chain constant region is obtained from an IgA, IgD, IgE, IgG, IgM antibody or a subtype thereof. In some embodiments, the immunoglobulin heavy chain constant region is obtained from IgG1 or IgG2. In some embodiments, the immunoglobulin heavy chain constant region is obtained from IgG2. In some embodiments, the immunoglobulin heavy chain constant region is obtained from a human immunoglobulin heavy chain region. In other embodiments, the immunoglobulin heavy chain constant region is obtained from a mouse immunoglobulin heavy chain constant region.

In some embodiments, the polypeptide does not comprise an antibody variable region. In some embodiments, the polypeptide does not have an antigen-binding site.

The polypeptides are anchored in the cell membrane, at least partially, by a transmembrane portion of the polypeptide or a GPI-membrane anchor. In some embodiments, the transmembrane portion is obtained from a Type I transmembrane protein. Type I transmembrane proteins are situated so that their N-terminus is outside of the membrane. Type I transmembrane proteins, may be single pass, meaning they cross the membrane only once, or multi-pass, meaning they cross the membrane several times. The transmembrane portion may be obtained from a variety of sources, including but not limited to, immunoglobulin and non-immunoglobulin proteins. In some embodiments, the transmembrane portion is taken from a protein that is part of the immunoglobulin superfamily, including but not limited to, CD4, CD8, Class I MHC, Class II MHC, CD19, T-cell receptor α and β chains, CD3, zeta chain, ICAM1 (CD54), ICAM2, ICAM3, ICAM4, ICAM5, CD28, CD79a, CD79b, and CD2. In some embodiments, the transmembrane portion is obtained from a human protein. In some embodiments, the transmembrane portion is obtained from a murine protein. In some embodiments, the transmembrane portion is obtained from a human CD4.

In some embodiments, the polypeptides further comprise at least a portion of an intracellular domain. In some embodiments, the intracellular domain is obtained from the same protein the transmembrane portion is obtained from. In some embodiments, the intracellular domain is obtained from a different protein than the protein the transmembrane portion is obtained from. In some embodiments, the intracellular domain is modified. In some embodiments, the intracellular domain is modified so the normal function of the domain is removed or inactivated. Modifications may include, but are not limited to, removal of a protein binding site, removal or inhibition of an activation site, and removal or inhibition of a phosphorylation site. In some embodiments, the polypeptide comprises a transmembrane and intracellular domain region from human CD4. In other embodiments, the polypeptide comprises a transmembrane and intracellular domain region from human CD4 wherein the intracellular domain has been modified. In some embodiments, the intracellular domain has been modified to remove a lck protein binding site.

In some embodiments, the transmembrane portion or transmembrane portion with intracellular domain is selected from the group consisting of: SEQ ID NO:13, SEQ ID NO:14, SEQ ID NO:15, SEQ ID NO:16, and SEQ ID NO:17. In some embodiments, the transmembrane portion with intracellular domain is SEQ ID NO:15.

In some embodiments, the polypeptides are anchored to the cell membrane by a GPI-membrane anchor. In some embodiments, the polypeptides are anchored to the cell membrane by a GPI linkage where the typical hydrophobic C-terminal amino acid residues are cleaved from the propeptide and the C-terminus of the polypeptide is covalently linked to glycosylphosphatidylinositol. The hydrophobic lipid moiety of GPI retains the polypeptide at the cell membrane. In some embodiments, the hydrophobic C-terminal portion of the molecule responsible for GPI linkage is obtained from CD52, CD55, CD58, CD59, and other similar proteins.

The polypeptides of the present invention are membrane-bound and comprise an immunoglobulin heavy chain constant region expressed on the surface of a cell. In some embodiments, the polypeptide is able to associate with a second polypeptide to form a heterodimeric molecule. In some embodiments, the second polypeptide comprises an immunoglobulin heavy chain. In some embodiments, the second polypeptide comprises an immunoglobulin heavy chain and an immunoglobulin light chain as a single chain molecule. In some embodiments, the second polypeptide comprises an immunoglobulin light chain. In some embodiments, the immunoglobulin light chain is associated with the immunoglobulin heavy chain. In some embodiments, the second polypeptide comprises an immunoglobulin heavy chain-light chain pair. As used herein, "an immunoglobulin heavy chain-light chain pair" includes a single chain immunoglobulin containing both an immunoglobulin heavy chain and an immunoglobulin light chain in one polypeptide. In some embodiments, the immunoglobulin heavy chain-light chain pair comprises a single antigen-binding site. In some embodiments, the membrane-bound polypeptide associates with an immunoglobulin heavy chain-light chain pair to form a heterodimeric antibody molecule, wherein the heterodimeric antibody molecule comprises one single antigen-binding site. In some embodiments, the heterodimeric antibody molecule is a monovalent antibody.

The polypeptides of the present invention may associate with a second polypeptide by any number of means including, but not limited to, non-covalent associations or covalent associations. In some embodiments, the polypeptide associates with a second polypeptide by non-covalent bonds, such as ionic bonds. In some embodiments, the polypeptide associates with a second polypeptide by covalent bonds, such as disulfide bonds. In some embodiments, the polypeptide is able to form at least one disulfide bond with a second polypeptide. In some embodiments, the polypeptide forms one disulfide bond with a second polypeptide. In other embodiments, the polypeptide forms two disulfide bonds with a second polypeptide. In other embodiments, the polypeptide forms three or four disulfide bonds with a second polypeptide. In other embodiments, the polypeptide is able to form at least one disulfide bond with the immunoglobulin heavy chain constant region of an immunoglobulin heavy chain-light chain pair to form a heterodimeric antibody molecule.

In some embodiments, the polypeptides of the present invention are able to form disulfide bonds with a second polypeptide to form a heterodimeric molecule. By their design, the polypeptides generally are not able to form disulfide bonds with a polypeptide that is already part of a heterodimeric or a homodimeric molecule. The polypeptides generally are not able to form disulfide bonds with a secreted antibody molecule. In some embodiments, the polypeptides do not bind secreted antibody. In some embodiments, the heterodimeric molecule comprising a polypeptide of the present invention does not bind antibody. In certain embodiments, the heterodimeric molecule comprising a polypeptide of the present invention does not bind secreted antibody.

In some embodiments, the invention provides a polypeptide comprising: (a) an immunoglobulin heavy chain constant region comprising CH2 and CH3; and (b) a transmembrane portion. In certain embodiments, the polypeptide comprises: (a) an human IgG2 heavy chain constant region comprising CH2 and CH3; and (b) a human CD4 transmembrane portion. In certain embodiments, the polypeptide comprises: (a) an immunoglobulin heavy chain constant region comprising CH2 and CH3; (b) a transmembrane portion; and (c) a fluorescent molecule. In certain embodiments, the polypeptide comprises: (a) an immunoglobulin heavy chain constant region comprising CH2 and CH3; (b) a CD4 transmembrane portion; and (c) a fluorescent molecule. In certain embodiments, the polypeptide comprises: (a) an human IgG2 heavy chain constant region comprising CH2 and CH3; (b) a human CD4 transmembrane portion; and (c) a fluorescent molecule. In certain embodiments, the fluorescent molecule is GFP.

In some embodiments, the invention provides a polypeptide comprising: (a) an immunoglobulin heavy chain constant region comprising SEQ ID NO:2, SEQ ID NO:4, SEQ ID NO:6, or SEQ ID NO:8; and (b) a transmembrane portion comprising SEQ ID NO:13 or SEQ ID NO:16. In some embodiments, the polypeptide comprises an immunoglobulin heavy chain constant region comprising SEQ ID NO:2 and a transmembrane portion comprising SEQ ID NO:16. In some embodiments, the polypeptide comprises an immunoglobulin heavy chain constant region comprising SEQ ID NO:2 and a transmembrane portion of SEQ ID NO:17. In some embodiments, the polypeptide comprises an immunoglobulin heavy chain constant region comprising SEQ ID NO:2 and a transmembrane portion comprising SEQ ID NO:13. In some embodiments, the polypeptide comprises an immunoglobulin heavy chain constant region comprising SEQ ID NO:2 and a transmembrane portion of SEQ ID NO:15. In some embodiments, the polypeptide comprises an immunoglobulin heavy chain constant region comprising SEQ ID NO:4 and a transmembrane portion comprising SEQ ID NO:16. In some embodiments, the polypeptide comprises an immunoglobulin heavy chain constant region comprising SEQ ID NO:4 and a transmembrane portion of SEQ ID NO:17. In some embodiments, the polypeptide comprises an immunoglobulin heavy chain constant region comprising SEQ ID NO:4 and a transmembrane portion comprising SEQ ID NO:13. In some embodiments, the polypeptide comprises an immunoglobulin heavy chain constant region comprising SEQ ID NO:4 and a transmembrane portion of SEQ ID NO:15. In some embodiments, the polypeptide comprises an immunoglobulin heavy chain constant region comprising SEQ ID NO:6 and a transmembrane portion comprising SEQ ID NO:16. In some embodiments, the polypeptide comprises an immunoglobulin heavy chain constant region comprising SEQ ID NO:6 and a transmembrane portion of SEQ ID NO:17. In some embodiments, the polypeptide comprises an immunoglobulin heavy chain constant region comprising SEQ ID NO:6 and a transmembrane portion comprising SEQ ID NO:13. In some embodiments, the polypeptide comprises an immunoglobulin heavy chain constant region comprising SEQ ID NO:6 and a transmembrane portion of SEQ ID NO:15. In some embodiments, the polypeptide comprises an immunoglobulin heavy chain constant region comprising SEQ ID NO:8 and a transmembrane portion comprising SEQ ID NO:16. In some embodiments, the polypeptide comprises an immunoglobulin heavy chain constant region comprising SEQ ID NO:8 and a transmembrane portion of SEQ ID NO:17. In some embodiments, the polypeptide comprises an immunoglobulin heavy chain constant region comprising SEQ ID NO:8 and a transmembrane portion comprising SEQ ID NO:13. In some embodiments, the polypeptide comprises an immunoglobulin heavy chain constant region comprising SEQ ID NO:8 and a transmembrane portion of SEQ ID NO:15.

In some embodiments, the invention provides a polypeptide comprising: an amino acid sequence having at least about 80% sequence identity to SEQ ID NO:2, SEQ ID NO:4, SEQ ID NO:6, or SEQ ID NO:8, and an amino acid sequence having at least 80% sequence identity to SEQ ID NO:13, SEQ ID NO: 14, SEQ ID NO:15, SEQ ID NO:16, or SEQ ID NO:17. In certain embodiments, the polypeptide comprises an amino acid sequence having at least about 85%, at least about 90%, at least about 95%, at least about 97%, or at least about 99% sequence identity to SEQ ID NO:2, SEQ ID NO:4, SEQ ID NO:6, or SEQ ID NO:8, and an amino acid sequence having at least about 85%, at least about 90%, at least about 95%, at least about 97%, or at least about 99% sequence identity to SEQ ID NO:13, SEQ ID NO:14, SEQ ID NO:15, SEQ ID NO:16, or SEQ ID NO:17. In some embodiments, the polypeptide comprises an amino acid sequence having at least about 95% identity to SEQ ID NO:2 and an amino acid sequence having at least about 95% identity to SEQ ID NO:14 or SEQ ID NO:15. In some embodiments, the polypeptide comprises an amino acid sequence having at least about 95% identity to SEQ ID NO:4 and an amino acid sequence having at least about 95% identity to SEQ ID NO:14 or SEQ ID NO:15. In some embodiments, the polypeptide comprises an amino acid sequence having at least about 95% identity to SEQ ID NO:6 and an amino acid sequence having at least about 95% identity to SEQ ID NO:14 or SEQ ID NO:15. In some embodiments, the polypeptide comprises an amino acid sequence having at least about 95% identity to SEQ ID NO:8 and an amino acid sequence having at least about 95% identity to SEQ ID NO:14 or SEQ ID NO:15.

In certain embodiments, the polypeptide comprises an amino acid sequence having at least 80% sequence identity to SEQ ID NO:10, SEQ ID NO:12, or SEQ ID NO:28. In certain embodiments, the polypeptide comprises an amino acid sequence having at least about 85%, at least about 90%, at least about 95%, at least about 97%, or at least about 99% sequence identity to SEQ ID NO:10, SEQ ID NO:12, or SEQ ID NO:28. In some embodiments, the invention provides a polypeptide comprising SEQ ID NO:10, SEQ ID NO:12, or SEQ ID NO:28.

The polypeptides of the present invention contain a signal sequence that directs the transport of the proteins. Signal sequences (also referred to as signal peptides or leader sequences) are located at the N-terminus of nascent polypeptides. They target the polypeptide to the endoplasmic reticulum and the proteins are sorted to their destinations, for example, to the inner space of an organelle, to an interior membrane, to the cell's outer membrane, or to the cell exterior via secretion. Most signal sequences are cleaved from the protein by a signal peptidase after the proteins are transported to the endoplasmic reticulum. The cleavage of the signal sequence from the polypeptide usually occurs at a specific site in the amino acid sequence and is dependent upon amino acid residues within the signal sequence. Although there is usually one specific cleavage site, more than one cleavage site may be recognized and/or used by a signal peptidase resulting in a non-homogenous N-terminus of the polypeptide. For example, the use of different cleavage sites within a signal sequence can result in a polypeptide expressed with different N-terminal amino acids. Accordingly, in some embodiments, the polypeptides as described herein may comprise a mixture of polypeptides with different N-termini. In some embodiments, the N-termini differ in length by 1, 2, 3, 4, or 5 amino acids. In some embodiments, the polypeptide is substantially homogeneous, i.e., the polypeptides have the same N-terminus. In some embodiments, the signal sequence of the polypeptide comprises one or more (e.g., one, two, three, four, five, six, seven, eight, nine, ten, etc.) amino acid substitutions and/or deletions. In some embodiments, the signal sequence of the polypeptide comprises amino acid substitutions and/or deletions that allow one cleavage site to be dominant, thereby resulting in a substantially homogeneous polypeptide with one N-terminus. Various algorithms and software that can be used to predict signal peptidase cleavage sites are known in the art and are publicly available (e.g., SignalP software).

In certain embodiments, the polypeptide comprises an amino acid sequence having at least 80% sequence identity to SEQ ID NO:22, SEQ ID NO:23, or SEQ ID NO:26. In certain embodiments, the polypeptide comprises an amino acid sequence having at least about 85%, at least about 90%, at least about 95%, at least about 97%, or at least about 99% sequence identity to SEQ ID NO:22, SEQ ID NO:23, or SEQ ID NO:26. In some embodiments, the polypeptide (before signal sequence cleavage) comprises SEQ ID NO:22, SEQ ID NO:23, or SEQ ID NO:26.

In certain embodiments, the polypeptide comprises an amino acid sequence having at least 80% sequence identity to SEQ ID NO:30, SEQ ID NO:31, or SEQ ID NO:32. In certain embodiments, the polypeptide comprises an amino acid sequence having at least about 85%, at least about 90%, at least about 95%, at least about 97%, or at least about 99% sequence identity to SEQ ID NO:30, SEQ ID NO:31, or SEQ ID NO:32. In some embodiments, the polypeptide comprises SEQ ID NO:32. In some embodiments, the polypeptide consists essentially of SEQ ID NO:32. In some embodiments, the polypeptide comprises SEQ ID NO:30. In some embodiments, the polypeptide consists essentially of SEQ ID NO:30. In some embodiments, the polypeptide comprises SEQ ID NO:31. In some embodiments, the polypeptide consists essentially of SEQ ID NO:31. A polypeptide that "consists essentially of" certain amino acids or is "consisting essentially of" certain amino acids may, in some embodiments, include one or more (e.g., one, two, three, four or more) additional amino acids, so long as the additional amino acids do not materially affect the function of the polypeptide. A polypeptide that "consists essentially of" certain amino acids or is "consisting essentially of" certain amino acids may, in some embodiments, be reduced by one or more (e.g., one, two, three, four or more) amino acids, so long as the missing amino acids do not materially affect the function of the polypeptide.

In some embodiments, the invention provides an antibody molecule comprising any of the polypeptides described herein. In some embodiments, the antibody molecule further comprises a second polypeptide comprising an immunoglobulin heavy chain. In some embodiments, the antibody molecule further comprises an immunoglobulin light chain. In some embodiments, the antibody molecule further comprises a second polypeptide comprising a single chain immunoglobulin with an immunoglobulin heavy chain and an immunoglobulin light chain. In certain embodiments, the antibody comprises a single antibody binding site (i.e., monovalent antibody).

In some embodiments, the invention provides a heterodimeric molecule comprising any of the polypeptides described herein. In some embodiments, the heterodimeric molecule further comprises a second polypeptide comprising a dimerization domain. In some embodiments, the second polypeptide comprises an immunoglobulin constant region. In some embodiments, the second polypeptide comprises an immunoglobulin heavy chain. In some embodiments, the second polypeptide comprises an immunoglobulin light chain. In some embodiments, the second polypeptide comprises a single chain immunoglobulin with an immunoglobulin heavy chain and an immunoglobulin light chain. In certain embodiments, the heterodimeric molecule comprises a single antibody binding site (i.e., monovalent antibody). In certain embodiments, the invention provides a heterodimeric molecule comprising: (a) a first polypeptide comprising an extracellular portion comprising a dimerization domain, and a transmembrane portion, and (b) a second polypeptide comprising a dimerization domain. In certain embodiments, the first and second dimerization domains are the same. In certain embodiments, the first and second dimerization domains are different.

In some embodiments, a heterodimeric molecule comprises (a) a first polypeptide comprising (i) an extracellular portion comprising a first dimerization domain; and (ii) a transmembrane portion; and (b) a second polypeptide comprising a second dimerization domain. In some embodiments, the heterodimeric molecule comprises a first dimerization domain which is an immunoglobulin constant region. In some embodiments, the heterodimeric molecule comprises a first dimerization domain which is an immunoglobulin heavy chain constant region. In some embodiments, the heterodimeric molecule comprises a second dimerization domain which is an immunoglobulin constant region. In some embodiments, the heterodimeric molecule comprises a second dimerization domain which is an immunoglobulin heavy chain constant region. In certain embodiments, the heterodimeric molecule comprises a first polypeptide comprising any of the polypeptides described herein.

The polypeptides described herein can be produced by any suitable method known in the art. Such methods range from direct protein synthesis methods to constructing a DNA sequence encoding polypeptide sequences and expressing those sequences in a suitable host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional variants thereof.

In some embodiments, a DNA sequence encoding a polypeptide of interest may be constructed by chemical synthesis using an oligonucleotide synthesizer. Oligonucleotides can be designed based on the amino acid sequence of the desired polypeptide and by selecting those codons that are favored in the host cell in which the recombinant polypeptide of interest will be produced. Standard methods can be applied to synthesize a polynucleotide sequence encoding a polypeptide of interest. For example, a complete amino acid sequence can be used to construct a back-translated gene. In some embodiments, a DNA oligomer containing a nucleotide sequence coding for the particular polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by recombinant technology, chemical synthesis, or another method), the polynucleotide sequences encoding a particular polypeptide of interest can be inserted into an expression vector and operatively linked to an expression control sequence appropriate for expression of the polypeptide in a desired host. Proper assembly can be confirmed by nucleotide sequencing, restriction mapping, and/or expression of a biologically active polypeptide in a suitable host. As is well-known in the art, in order to obtain high expression levels of a transfected gene in a host, the gene must be operatively linked to transcriptional and translational expression control sequences that are functional in the chosen expression host.

In certain embodiments, recombinant expression vectors are used to amplify and express DNA encoding the polypeptides described herein. For example, recombinant expression vectors can be replicable DNA constructs that have synthetic or cDNA-derived DNA fragments encoding a polypeptide, operatively linked to suitable transcriptional or translational regulatory elements derived from mammalian, microbial, viral or insect genes. A transcriptional unit generally comprises an assembly of (1) a regulatory element or elements having a role in gene expression, for example, transcriptional promoters and/or enhancers, (2) a structural or coding sequence that is transcribed into mRNA and translated into protein, and (3) appropriate transcription and translation initiation and termination sequences. Regulatory elements can include an operator sequence to control transcription. The ability to replicate in a host, usually conferred by an origin of replication, and a selection gene to facilitate recognition of transformants can additionally be incorporated. DNA regions are "operatively linked" when they are functionally related to each other. For example, DNA for a signal peptide (secretory leader) is operatively linked to DNA for a polypeptide if it is expressed as a precursor that participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of an expression vector and control elements depends upon the choice of host. A wide variety of expression host/vector combinations can be employed. Useful expression vectors for eukaryotic hosts include, for example, vectors comprising expression control sequences from SV40, bovine papilloma virus, adenovirus and cytomegalovirus. Useful expression vectors for bacterial hosts include known bacterial plasmids, such as plasmids from E. coli, including pCR1, pBR322, pMB9 and their derivatives and wider host range plasmids, such as M13 and other filamentous single-stranded DNA phages.

Some expression vectors for eukaryotic hosts may have the ability to integrate into the host genome and some expression vector for eukaryotic hosts may persist in the nucleus as extrachromosomal entities. In some embodiments, episomal vectors may offer advantages, such as transfection of multiple copies per cell resulting in high expression of the polynucleotide of interest and/or higher transfection efficiency.

Suitable host cells for expression of the polypeptides as described herein include prokaryotes, yeast, insect or higher eukaryotic cells under the control of appropriate promoters. Prokaryotes include gram-negative or gram-positive organisms, for example, E. coli or Bacilli. Higher eukaryotic cells include established cell lines of mammalian origin as described below. Cell-free translation systems can also be employed.

Various mammalian or insect cell culture systems are used to express recombinant polypeptides. In some embodiments, expression of recombinant proteins in mammalian cells is preferred because such proteins are generally correctly folded, appropriately modified and completely functional. Examples of suitable mammalian host cell lines include, but are not limited to, COS-7 (monkey kidney-derived), L-929 (murine fibroblast-derived), C127 (murine mammary tumor-derived), 3T3 (murine fibroblast-derived), CHO (Chinese hamster ovary-derived), HEK-293 (human embryonic kidney-derived), HeLa (human cervical cancer-derived) and BHK (hamster kidney fibroblast-derived) cell lines. In some embodiments, variants of a cell line may be used. For example, 293T cells are HEK-293 cells that express the SV40 Large T-antigen, which allows for episomal replication of transfected plasmids containing the SV40 origin of replication. Mammalian expression vectors can comprise non-transcribed elements such as an origin of replication, a suitable promoter and enhancer linked to the gene to be expressed, and other 5' or 3' flanking non-transcribed sequences, and 5' or 3' non-translated sequences, such as necessary ribosome binding sites, a polyadenylation site, splice donor and acceptor sites, and transcriptional termination sequences. In some embodiments, baculovirus systems are used for production of heterologous proteins in insect cells. These methods and techniques are well known to those of skill in the art (see, e.g., Luckow and Summers, 1988, Bio/Technology, 6:47).

In certain embodiments, the polypeptides described herein are isolated. In certain embodiments, the polypeptides described herein are substantially pure.

The proteins expressed by a host cell can be purified according to any suitable method. Such methods include chromatography (e.g., ion exchange, affinity and sizing column chromatography), centrifugation, differential solubility, or by any other standard technique for protein purification Affinity tags such as hexa-histidine, maltose binding domain, influenza coat sequence and glutathione-S-transferase can be attached to the protein to allow easy purification by passage over an appropriate affinity column. Isolated proteins can also be physically characterized using such techniques as proteolysis, high performance liquid chromatography (HPLC), nuclear magnetic resonance and x-ray crystallography.

In some embodiments, supernatants from expression systems that secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. In some embodiments, an anion exchange resin can be employed, for example, a matrix or substrate having pendant diethylaminoethyl (DEAE) groups. The matrices can be acrylamide, agarose, dextran, cellulose or other types commonly employed in protein purification. In some embodiments, a cation exchange step can be employed. Suitable cation exchangers include various insoluble matrices comprising sulfopropyl or carboxymethyl groups. In some embodiments, a hydroxyapatite (CHT) media can be employed, including but not limited to, ceramic hydroxyapatite. In some embodiments, one or more reversed-phase HPLC steps employing hydrophobic RP-HPLC media, e.g., silica gel having pendant methyl or other aliphatic groups, can be employed to further purify a protein. Some or all of the foregoing purification steps, in various combinations, can be employed to provide a homogeneous recombinant protein.

In certain embodiments, the invention provides polynucleotides comprising polynucleotides that encode a polypeptide comprising an immunoglobulin heavy chain constant region and a transmembrane portion. In certain embodiments, the invention provides polynucleotides comprising polynucleotides that encode a polypeptide comprising an immunoglobulin heavy chain constant region and a GPI-membrane portion. The phrase "polynucleotides that encode a polypeptide" encompasses a polynucleotide that includes only coding sequences for the polypeptide, as well as a polynucleotide that includes additional coding and/or non-coding sequences. The polynucleotides of the invention can be in the form of RNA or in the form of DNA. DNA includes cDNA, genomic DNA, and synthetic DNA; and can be double-stranded or single-stranded, and if single-stranded, can be the coding strand or non-coding (antisense) strand.

In some embodiments, a polynucleotide comprises a polynucleotide encoding a polypeptide comprising SEQ ID NO:10. In some embodiments, the polynucleotide comprises a polynucleotide encoding a polypeptide comprising SEQ ID NO:12. In some embodiments, the polynucleotide comprises a polynucleotide encoding a polypeptide comprising SEQ ID NO:28. In some embodiments, the polynucleotide comprises a polynucleotide encoding a polypeptide (with or without a signal sequence) comprising SEQ ID NO:22, SEQ ID NO:23, or SEQ ID NO:26. In some embodiments, the polynucleotide comprises a polynucleotide encoding a polypeptide comprising SEQ ID NO:30. In some embodiments, the polynucleotide comprises a polynucleotide encoding a polypeptide comprising SEQ ID NO:31. In some embodiments, the polynucleotide comprises a polynucleotide encoding a polypeptide comprising SEQ ID NO:32. In some embodiments, the polynucleotide comprises a polynucleotide encoding a polypeptide of SEQ ID NO:30. In some embodiments, the polynucleotide comprises a polynucleotide encoding a polypeptide of SEQ ID NO:31. In some embodiments, the polynucleotide comprises a polynucleotide encoding a polypeptide of SEQ ID NO:32.

In some embodiments, a polynucleotide comprises a polynucleotide of SEQ ID NO:9, SEQ ID NO:11, or SEQ ID NO:29. In some embodiment, a polynucleotide comprises a polynucleotide of SEQ ID NO:24, SEQ ID NO:25, or SEQ ID NO:27. In certain embodiments, a polynucleotide comprises a polynucleotide having a sequence of at least 80% identical, at least 85% identical, at least about 90% identical, at least about 95% identical, and in some embodiments, at least 96%, 97%, 98% or 99% identical to a polynucleotide of SEQ ID NO:9, SEQ ID NO:11, SEQ ID NO:24, SEQ ID NO:25, SEQ ID NO:27, or SEQ ID NO:29.

Also provided is a polynucleotide that comprises a polynucleotide that hybridizes to SEQ ID NO:9, SEQ ID NO:11, SEQ ID NO:24, SEQ ID NO:25, SEQ ID NO:27, or SEQ ID NO:29. In some embodiments, the hybridization is under condition of high stringency.

In certain embodiments, the polynucleotides comprise the coding sequence for the mature polypeptide fused in the same reading frame to a polynucleotide that aids, for example, in expression and/or secretion of a polypeptide from a host cell. For example, a leader or signal sequence functions as a sequence for controlling transport of a polypeptide to the cell surface, and secretion from the cell if the polypeptide is a secretory protein. The polypeptide having a leader sequence (or signal sequence) is a preprotein and can have the leader sequence cleaved by the host cell to produce the mature form of the polypeptide. The polynucleotides can also encode for a proprotein that is the mature protein plus additional 5' amino acid residues. A mature protein having a prosequence is a proprotein and is an inactive form of the protein. Once the prosequence is cleaved an active mature protein remains.

In certain embodiments the polynucleotides comprise the coding sequence for the mature polypeptide fused in the same reading frame to a marker or tag sequence that allows, for example, for purification and/or identification of the expressed polypeptide. In some embodiments, when a bacterial host is used, the marker sequence can be a hexa-histidine tag supplied by a pQE-9 vector to provide for purification of the mature polypeptide. In other embodiments, when a mammalian host is used (e.g., COS-7 cells) the marker sequence can be a hemagglutinin (HA) tag derived from the influenza hemagglutinin protein. In some embodiments, the marker sequence is "FLAG", a peptide of sequence DYKDDDDK (SEQ ID NO:17) that can also be used in conjunction with other affinity tags.

The present invention further relates to variants of the hereinabove described polynucleotides encoding, for example, fragments, analogs, and/or derivatives of the polypeptides.

In certain embodiments, the present invention provides polynucleotides comprising polynucleotides having a nucleotide sequence at least 80% identical, at least 85% identical, at least 90% identical, at least 95% identical, and in some embodiments, at least 96%, 97%, 98% or 99% identical to a polynucleotide encoding a polypeptide described herein.

As used herein, the phrase a polynucleotide having a nucleotide sequence at least, for example, 95% "identical" to a reference nucleotide sequence is intended to mean that the nucleotide sequence of the polynucleotide is identical to the reference sequence except that the polynucleotide sequence can include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence can be deleted or substituted with another nucleotide, or a number of nucleotides up to 5% of the total nucleotides in the reference sequence can be inserted into the reference sequence. These mutations of the reference sequence can occur at the 5' or 3' terminal positions of the reference nucleotide sequence or anywhere between those terminal positions, interspersed either individually among nucleotides in the reference sequence or in one or more contiguous groups within the reference sequence.

The polynucleotide variants can contain alterations in the coding regions, non-coding regions, or both. In some embodiments, the polynucleotide variants contain alterations that produce "silent" substitutions, additions, or deletions, but do not alter the properties or activities of the encoded polypeptide. In some embodiments, polynucleotide variants contain "silent" substitutions due to the degeneracy of the genetic code. Polynucleotide variants can be produced for a variety of reasons, for example, to optimize codon expression for a particular host (e g, change codons in the human mRNA to those preferred by a bacterial host such as E. coli).

In certain embodiments, the polynucleotides described herein are isolated. In certain embodiments, the polynucleotides described herein are substantially pure.

Vectors and cells comprising the polynucleotides described herein are also provided. In some embodiments, an expression vector comprises a polynucleotide molecule. In some embodiments, a host cell comprises an expression vector comprising the polynucleotide molecule. In some embodiments, a host cell comprises a polynucleotide molecule. In some embodiments, a host cell comprises a polypeptide encoded by the polynucleotide molecule. In some embodiments, a host cell produces a polypeptide encoded by the polynucleotide molecule.

III. Cells

The present invention also provides cells that express the polypeptides described herein and provides methods of producing the cells. The cells (e.g., host cells) used to make the cells described herein include all mammalian cells, cell lines, and cell cultures. In some embodiments, the cells are derived from mammals, such as mice, rats, or other rodents, or from primates, such as humans or monkeys. In some embodiments, the cell is a murine cell. In some embodiments, the cell is a human cell. In other embodiments, the cell is a mammalian germ cell or a somatic cell. In other embodiments, the cell is a primary cell culture or an immortalized cell line. The mammalian cells are typically grown in cell culture. In some embodiments, the cells are adhered to a solid surface. In other embodiments, the cells are grown in suspension.

A wide variety of host cells may be transfected with polynucleotides and/or vectors comprising polynucleotides encoding for the polypeptides of the present invention. In some embodiments, the cells will be immortalized eukaryotic cells including, but not limited to, SP2/0, SP2/0-Ag14, NS/0, YB2/0, K6H6/B5, NS-1, FO, Y3/Ag 1.2.3, P3X63Ag8.653, other myelomas, hybridomas, Chinese hamster ovary cells (CHO), HeLa cells, baby hamster kidney cells (BHK), CV-1 cells, 3T3 cells, L cells, TC7 cells, and human embryonic kidney cells (HEK-293 and 293T). In some embodiments, the cells are known fusion partner cell lines. In some embodiments, the cells are immortalized cell lines that fuse efficiently, support high level expression of antibodies, and are sensitive to a selection medium. These cell lines can include, but are not limited to, Sp2/0, SP2/0-Ag14, YB2/0, K6H6/B5, NS-1, FO, Y3/Ag 1.2.3, and P3X63Ag8.653. In some embodiments, the cells are myelomas that do not express immunoglobulin chains. In some embodiments, the cells are a hybridoma or hybridoma library. In certain embodiments, the cells are human cells. In certain embodiments, the cells are HEK-293 cells or a variant thereof (e.g., 293T cells). In certain embodiments, the cells are CHO cells. In certain embodiments, the cells are murine cells. In some embodiments, the cells are SP2/0 or a variant thereof (e.g., SP2/0-Ag14).

A cell expressing a polypeptide of the present invention may be made by a variety of methods known to one of skill in the art. The polynucleotides, vectors and/or constructs described herein can be introduced into suitable host cells by a variety of methods. In general, transfection or infection with a vector is used to obtain mammalian cells that express the polypeptides of the invention.

In some embodiments, the polynucleotide is introduced into a cell by transfection. In some embodiments, the transfection is a transient expression, usually resulting in expression of the transfected polypeptide for a limited time period. In other embodiments, the transfection is a stable transfection, resulting in permanent expression of the transfected polypeptide. In some embodiments, stable transfection is accompanied by integration of the input DNA into the cellular genome. In some embodiments, the stable transfection results in episomal maintenance and replication of the input DNA.

DNA can be introduced into eukaryotic cells via conventional transfection techniques. The term "transfection" refers to a variety of techniques known to one of skill in the art for introducing foreign polynucleotides (e.g., DNA) into a host cell. These techniques include, but are not limited to, calcium phosphate or calcium chloride co-precipitation, DEAE-dextran-mediated transfection, liposome-mediated transfection, electroporation, and microinjection. These and other suitable methods for transfecting host cells can be found in many standard laboratory manuals. In some embodiments, cells are transfected using liposome-mediated transfection or "lipofection". Lipofection is a lipid-based transfection technology wherein the nucleic acids associate with a lipid-based transfection reagent resulting in tight compaction and protection of the nucleic acids. The main advantages of lipofection are high efficiency, the ability to transfect all types of nucleic acids in a wide range of cell types, ease of use, reproducibility, and low toxicity. In addition, lipofection is suitable for all transfection applications including, but not limited to, transient, stable, co-transfection, sequential, or multiple transfections.

In some embodiments, the cells are stably transfected with a polynucleotide expressing the polypeptides described herein. For stable transfection of mammalian cells, it is known that, depending upon the expression vector and transfection technique used, only a small fraction of cells may integrate the DNA into their genome. In transfection of mammalian cells with an episomal vector, a larger fraction of cells may incorporate and maintain the DNA. In order to identify and select these cells, a gene that encodes a selectable marker (e.g., resistance to antibiotics) is generally introduced into the host cells along with the gene(s) of interest. Various selectable markers include those that confer resistance to drugs, such as G418, hygromycin and methotrexate. Polynucleotides encoding a selectable marker can be introduced into a host cell on the same vector as that encoding the polypeptide or can be introduced on a separate vector. Cells stably transfected with the introduced polynucleotides can be identified by drug selection (e.g., cells that have incorporated the selectable marker gene will survive, while the other cells die).

In some embodiments, the polynucleotide is introduced into a cell by a vector. Vectors can be derived from viral genomes that yield virions or virus-like particles that may or may not replicate independently as extrachromosomal elements. Virion particles containing a polynucleotide encoding a desired polypeptide can be introduced into host cells by infection. In some embodiments, the viral vector becomes integrated into the cellular genome. Viral vectors for transformation of mammalian cells include, but are not limited to, SV40 vectors, and vectors based on papillomavirus, adenovirus, Epstein-Ban virus, vaccinia virus, and retroviruses, such as Rous sarcoma virus, or a mouse leukemia virus, such as Moloney murine leukemia virus.

Also provided are methods of producing cells expressing the polypeptides described herein. In some embodiments, provided herein are methods of producing cells, comprising transfecting cells with a polynucleotide or vector encoding a polypeptide described herein. In some embodiments, the transfected cells express the polypeptide. In some embodiments, the cells are transiently transfected. In some embodiments, the cells are stably transfected. In some embodiments, the polynucleotide encoding a polypeptide is integrated into the genome of the cell. In some embodiments, the transfected polynucleotide encoding a polypeptide is stably expressed in the cell. In other embodiments, the polypeptide is expressed on the surface of the transfected cells.

In some embodiments, the methods further comprise detecting expression of the polypeptide. The transfected cells can be assayed for expression of the polypeptide by any method known in the art. The assays which can be used include, but are not limited to, competitive and non-competitive assay systems using techniques such as Biacore analysis, flow cytometry, FACS analysis, immunofluorescence, immunocytochemistry, Western blot analysis, radioimmunoassay, ELISA, "sandwich" immunoassay, immunoprecipitation assay, precipitation reaction, gel diffusion precipitin reaction, immunodiffusion assay, agglutination assay, complement-fixation assay, immunoradiometric assay, fluorescent immunoassay, and protein A immunoassay. Such assays are routine and well known in the art (see, e.g., Ausubel et al., eds, 1994, Current Protocols in Molecular Biology, Vol. 1, John Wiley & Sons, Inc., New York).

In some embodiments, the methods comprise detecting expression of the polypeptide on the surface of the cell. In some embodiments, the cells are contacted with a detection molecule. In some embodiments, the detection molecule is an antibody to an immunoglobulin heavy chain constant region. In some embodiments, the detection molecule is labeled. In some embodiments, the detection molecule is labeled with a fluorophore or a chromophore. In some embodiments, the methods comprise detecting expression of the polypeptide using flow cytometry. In some embodiments, the methods comprise identifying the cells that are bound by the detection molecule by flow cytometry. As used herein, the phrase "a detection molecule" includes, but is not limited to, a population of detection molecules. For example, a detection molecule may be a solution of antibodies, or a solution of proteins or protein fragments.

Similarly, the phrase "cells bound by a detection molecule" includes, but is not limited to, cells bound by a number of detection molecules.

Flow cytometry and FACS are techniques known to those of skill in the art. Flow cytometry uses the principles of light scattering, light excitation and emission of fluorochrome molecules to generate specific multi-parameter data from cells. The instruments make measurements on cells as the cells flow in a stream one by one through a sensing point. Flow cytometry can be used for purification of cell populations or isolation of individual cells by fluorescence-activated cell sorting or FACS. In some embodiments, the cells are analyzed at 10-20,000 cells per second. In some embodiments, the cells are analyzed at 1,000-10,000 cells per second. In certain embodiments, the cells are analyzed at 100-1000 cells per second. In some embodiments, about $1 \times 10^6$ to $1 \times 10^8$ cells are analyzed. In some embodiments, about $1 \times 10^6$ cells are analyzed. In certain embodiments, about $5 \times 10^6$ cells are analyzed. In some embodiments, about $1 \times 10^7$ cells are analyzed. In some embodiments, about $2.5 \times 10^7$ cells are analyzed. In some embodiments, the cells are analyzed and sorted. For example, about $2.5 \times 10^7$ cells can be run through a FACS instrument and analyzed. Target cells can be sorted into the wells of about eight 96 wells, and 600 to 700 individual clones can be isolated. Thus, the use of flow cytometry allows for rapid screening of large numbers of cells. Similarly, the use of FACS allows for detection and sorting of a large number of cells and isolation of individual cells in a rapid manner.

In some embodiments, the methods of producing cells comprise transfecting cells with a polynucleotide or vector encoding a polypeptide described herein. In some embodiments, the transfected cells express the polypeptide. In some embodiments, the method comprises detecting expression of the polypeptide on the surface of the cells. In some embodiments, the method comprises selecting cells that express the polypeptide. In some embodiments, the cells are contacted with a detection molecule. In some embodiments, the detection molecule is an antibody to an immunoglobulin heavy chain constant region. In some embodiments, the detection molecule is a target of interest (e.g., a protein or fragment thereof). In some embodiments, the detection molecule is labeled. In some embodiments, the detection molecule is labeled with a fluorophore or a chromophore. In some embodiments, the methods comprise identifying the cells that are bound by the detection molecule by flow cytometry. In some embodiments, the methods comprise isolating the cells that are bound by the detection molecule by FACS.

Thus, the invention provides cells comprising a polynucleotide encoding for a polypeptide described herein. In some embodiments, the cells are produced by any of the methods described herein. In some embodiments, the cells comprise a vector comprising a polynucleotide encoding for a polypeptide described herein. In some embodiments, the cells comprise a polypeptide described herein. In some embodiments, the cells comprise a polypeptide comprising an immunoglobulin heavy chain constant region and a non-immunoglobulin transmembrane portion. In some embodiments, the polypeptide is membrane-bound and expressed on the surface of the cells.

The present invention also provides cells that produce a heterodimeric molecule. The heterodimeric molecules are membrane-bound, expressed at the cell surface and are not secreted from the cell. In some embodiments, the heterodimeric molecule comprises a polypeptide described herein and further comprises at least one additional polypeptide. In some embodiments, the additional polypeptide comprises an immunoglobulin heavy chain constant region comprising CH2 and CH3 domains. In some embodiments, the additional polypeptide comprises an immunoglobulin Fc region. In some embodiments, the additional polypeptide comprises an immunoglobulin heavy chain. In certain embodiments, the at least one additional polypeptide comprises an immunoglobulin heavy chain and an immunoglobulin light chain. In certain embodiments, the at least one additional polypeptide comprises a single chain immunoglobulin with an immunoglobulin heavy chain and an immunoglobulin light chain. In some embodiments, the additional polypeptide is an antibody.

In some embodiments, the heterodimeric molecule is a membrane-bound polypeptide covalently associated with a second polypeptide, wherein the membrane-bound polypeptide comprises: (a) an immunoglobulin heavy chain constant region, and (b) a transmembrane portion. In some embodiments, the membrane-bound polypeptide associates with a second polypeptide by forming disulfide bonds. In some embodiments, the membrane-bound polypeptide forms at least one disulfide bond with a second polypeptide to form the heterodimeric molecule.

In some embodiments, the heterodimeric molecule is a membrane-bound polypeptide covalently associated with an immunoglobulin heavy chain, wherein the membrane-bound polypeptide comprises: (a) an immunoglobulin heavy chain constant region, and (b) a transmembrane portion. In some embodiments, the membrane-bound polypeptide associates with the immunoglobulin heavy chain by forming disulfide bonds. In some embodiments, the membrane-bound polypeptide forms at least one disulfide bond with the immunoglobulin heavy chain. In some embodiments, the immunoglobulin heavy chain is paired with an immunoglobulin light chain, so that the heavy chain variable region and the light chain variable region form a single antigen-binding site. In some embodiments, the immunoglobulin heavy chain is part of a single chain immunoglobulin with both an immunoglobulin heavy chain and an immunoglobulin light chain. In some embodiments, the heterodimeric molecule is a monovalent antibody molecule. In some embodiments, the heterodimeric molecules expressed on the surface of a cell do not bind a secreted antibody.

Thus, in some embodiments, a cell comprises: (a) a polynucleotide encoding for a polypeptide comprising an immunoglobulin heavy chain constant region comprising CH2 and CH3 domains and a non-immunoglobulin transmembrane portion; and (b) at least one additional polynucleotide that encodes at least one additional polypeptide. In some embodiments, the at least one additional polypeptide comprises an immunoglobulin heavy chain, and/or an immunoglobulin light chain. In some embodiments, the at least one additional polypeptide comprises a single chain immunoglobulin with an immunoglobulin heavy chain and an immunoglobulin light chain. In some embodiments, the at least one additional polypeptide is an antibody. In some embodiments, the additional polypeptide is an antibody that can be secreted from the cell. In certain embodiments, the polypeptides of the present invention expressed on the surface of a cell do not bind a secreted antibody.

The present invention also provides hybridoma cells and methods of producing hybridomas, wherein the hybridoma expresses a polypeptide and/or a heterodimeric molecule described herein. In some embodiments, a method for producing a hybridoma cell comprises fusing cells expressing a polypeptide of the present invention with an antibody-producing cell. In some embodiments, the fused hybridoma cells express a heterodimeric antibody molecule on the surface of the cells. An antibody-producing cell is any cell that is capable of producing or is producing an antibody molecule including, but not limited to, a B-cell, a plasma cell, a myeloma, a hybridoma, and a recombinant cell. In some embodiments, the antibody-producing cell contributes an immunoglobulin heavy chain to the fused cells wherein the immunoglobulin heavy chain forms a heterodimeric molecule with the polypeptide expressed by the cell. In some embodiments, the antibody-producing cell contributes an immunoglobulin light chain to the fused cells, wherein the immunoglobulin light chain associates with an immunoglobulin heavy chain to form an antigen-binding site. In some embodiments, the antibody-producing cell contributes a single chain immunoglobulin with an immunoglobulin heavy chain and an immunoglobulin light chain to the fused cells, wherein the single chain immunoglobulin forms a heterodimeric molecule with the polypeptide expressed by the cell. In some embodiments, the antibody-producing cell is a mouse cell. In some embodiments, the antibody-producing cell is a human cell. In some embodiments, the antibody-producing cell is a population of antibody-producing cells. In some embodiments, the antibody-producing cells are cells isolated from an immunized animal. In some embodiments, the antibody-producing cells are cells isolated from a naive animal. In other embodiments, the antibody-producing cells comprise a plurality of polynucleotides. In some embodiments, the plurality of polynucleotides encodes a plurality of polypeptides comprising immunoglobulin heavy chains. In some embodiments, the plurality of polynucleotides encodes a plurality of polypeptides comprising immunoglobulin light chains. In some embodiments, the plurality of polynucleotides encodes a plurality of polypeptides comprising a single chain immunoglobulin with an immunoglobulin heavy chain and an immunoglobulin light chain. In some embodiments, the plurality of polynucleotides comprises a DNA library. In some embodiments, the DNA library is generated from cells of an immunized animal. In other embodiments, the DNA library is a naïve library. In some embodiments, the DNA library is a cDNA library. In some embodiments, the method produces a population (e.g., a library) of hybridoma cells that express a plurality of heterodimeric antibody molecules. Also provided are hybridomas or hybridoma libraries produced by the methods described herein.

The present invention also provides methods of producing a cell library that expresses heterodimeric molecules comprising the polypeptides described herein. In some embodiments, a method of producing a cell library comprises transfecting cells expressing a polypeptide of the present invention with a plurality of polynucleotides that encode a plurality of polypeptides. In some embodiments, the transfected cells express a heterodimeric molecule. In some embodiments, the heterodimeric molecule is expressed on the surface of the transfected cells. In some embodiments, the plurality of polynucleotides encodes a plurality of polypeptides comprising an immunoglobulin heavy chain constant region comprising CH2 and CH3 domains. In some embodiments, the plurality of polynucleotides encodes a plurality of polypeptides comprising an immunoglobulin Fc region. In some embodiments, the plurality of polynucleotides encodes a plurality of polypeptides comprising an immunoglobulin heavy chain. In some embodiments, the plurality of polynucleotides encodes a plurality of polypeptides comprising an immunoglobulin heavy chain and an immunoglobulin light chain. In some embodiments, the plurality of polynucleotides encodes a plurality of polypeptides comprising a single chain immunoglobulin with an immunoglobulin heavy chain and an immunoglobulin light chain. In some embodiments, the plurality of polynucleotides encodes a plurality of polypeptides, wherein each polypeptide comprises: (a) an immunoglobulin Fc region, and (b) a randomized polypeptide. In some embodiments, the plurality of polynucleotides comprises a DNA library. In some embodiments, the DNA library is generated from cells of an immunized animal. In other embodiments, the DNA library is generated from cells of a naïve animal. In some embodiments, the library is a naïve library. In some embodiments, the DNA library is a cDNA library. In certain embodiments, the DNA library encodes for a random polypeptide library. Also provided are cell libraries made by any of the methods described herein.

The present invention also provides cells that express the novel polypeptides of the present invention and also produce antibodies. Also provided are methods of producing these cells, wherein the cells express a polypeptide of the present invention, an antibody, and/or a heterodimeric molecule as described herein. In some embodiments, an antibody-producing cell is transfected with a polynucleotide that encodes any of the novel polypeptides described herein. In some embodiments, the transfected cells express the polypeptide. In some embodiments, the transfected cells express a heterodimeric molecule on the surface of the cells. In some embodiments, the heterodimeric molecule comprises the polypeptide and an immunoglobulin heavy chain. In some embodiments, the immunoglobulin heavy chain is associated with an immunoglobulin light chain to form a single antigen-binding site. In some embodiments, the immunoglobulin heavy chain is part of a single chain immunoglobulin. In some embodiments, the antibody-producing cell is a hybridoma library. In some embodiments, the antibody-producing cell is a hybridoma.

The present invention also provides cell libraries comprising the novel polypeptides as described herein. In some embodiments, each cell in a cell library comprises: (a) a first polypeptide comprising an immunoglobulin heavy chain constant region comprising CH2 and CH3 domains; and a transmembrane portion; and (b) a second polypeptide comprising an immunoglobulin heavy chain, wherein the two polypeptides are able to form a heterodimeric molecule. In some embodiments, the two polypeptides covalently associate. In some embodiments, the two polypeptides form at least one disulfide bond. In some embodiments, the heterodimeric molecule is expressed on the surface of the cells. In some embodiments, each cell further comprises an immunoglobulin light chain. In some embodiments, the second polypeptide is a single chain immunoglobulin. In some embodiments, the heterodimeric molecule comprises a single antigen-binding site.

The present invention also provides methods of identifying and/or selecting polypeptides that are not antibodies. The polypeptides can include, but are not limited to, cell surface receptors or fragments thereof, soluble receptors or fragments thereof, cell surface ligands or fragments thereof, and soluble ligands or fragments thereof. The polypeptides can include mutagenized or derivatized versions of proteins. The polypeptides can include randomized polypeptides, for example a randomized polypeptide library.

In some embodiments, each cell in a cell library comprises: (a) a first polypeptide comprising an immunoglobulin heavy chain constant region comprising CH2 and CH3 domains; and a transmembrane portion; and (b) a second polypeptide. In some embodiments, the two polypeptides covalently associate. In some embodiments, the two polypeptides form at least one disulfide bond. In some embodiments, the second polypeptide comprises an immunoglobulin heavy chain constant region comprising CH2 and CH3 domains, wherein the two polypeptides are able to form a heterodimeric molecule. In some embodiments, the second polypeptide comprises an immunoglobulin Fc region. In some embodiments, the second polypeptide comprises a single chain immunoglobulin with an immunoglobulin heavy chain and an immunoglobulin light chain. In some embodiments, the second polypeptide comprises a randomized polypeptide. In some embodiments, the second polypeptide comprises: (a) an immunoglobulin Fc region and (b) a randomized polypeptide.

Randomized polypeptides or a random polypeptide library (and the polynucleotides encoding for them) can be either fully randomized or they can be biased in their randomization. Any method known to those of skill in the art can be used to generate randomized polypeptides or a random peptide library, including but not limited to, chemical synthesis of the nucleotides and/or peptides. (See e.g., US Patent Appl. No. 2003/0170753 and International Appl. No. WO 00/20574).

The cell libraries described herein can be screened for cells producing a specific polypeptide. Thus, provided herein are methods of screening a cell library comprising contacting a cell library described herein with a detection molecule. In some embodiments, the method further comprises identifying the cells that are bound by the detection molecule. In some embodiments, the method further comprises isolating the cells that are bound by the detection molecule. The detection molecule can include, but is not limited to, proteins, carbohydrates, small molecules, and variants thereof. In some embodiments, the detection molecule is a protein or fragment thereof. In some embodiments, the detection molecule is an antigen of interest. In some embodiments, the detection molecule is a cell surface receptor, an antibody, a ligand or fragments thereof. In some embodiments, the detection molecule is labeled. In some embodiments, the detection molecule is labeled with a fluorophore, a chromophore or a magnetic compound. In some embodiments, the cells bound by the detection molecule are identified by flow cytometry. In some embodiments, the cells bound by the detection molecule are isolated by FACS.

IV. Methods of Identifying, Selecting, and/or Isolating Antibodies or Polypeptides The identification of hybridoma cells that produce monoclonal antibodies to an antigen of interest is typically accomplished by ELISA screening of cell supernatants. The supernatants can be produced by random cells isolated by single cell (limiting dilution) cloning techniques. Or the supernatants can be produced by pools of hybridoma cells from a hybridoma library, whereby the cells from any ELISA-positive pool must be sub-cloned and isolated by single cell cloning. These processes have many limitations. In the first case, large numbers of plates containing "single cell" cultures must be screened to find ELISA-positive clones. In the case of hybridoma pool screening, each ELISA-positive pool must be further separated by limiting dilution cloning to isolate a pure clone of the hybridoma of interest. Both of these methods are labor intensive and time consuming. Furthermore, in some circumstances the desired clone may represent an extremely low percentage of the hybridoma library, making the identification of the rare clone difficult. In addition, the ELISA screening approach identifies binding activity to a single antigen. To assess whether an individual hybridoma clone is producing a monoclonal antibody able to bind to more than one antigen, multiple, sequential ELISAs need to be performed.

The novel polypeptides, cells, and cell libraries of the present invention can be used in methods of identifying and isolating a cell producing an antibody specific for an antigen or target of interest. In some embodiments, a method of identifying a cell that produces a specific antibody comprises fusing cells comprising a novel polypeptide as described herein, with an antibody-producing cell to produce a population of hybridoma cells. In some embodiments, the hybridoma cells express a heterodimeric antibody molecule on the surface of the cells. In some embodiments, the method comprises contacting the population of hybridoma cells with a detection molecule. In some embodiments, the method comprises identifying the hybridoma cells that are bound by the detection molecule. In some embodiments, the method comprises isolating the cells that are bound by the detection molecule. In some embodiments, the detection molecule is a target of interest. In some embodiments, the detection molecule is a protein or fragment thereof. In some embodiments, the detection molecule is labeled.

In some embodiments, hybridoma cells producing an antibody molecule are identified using a form of affinity selection known to those of skill in the art as "panning". The cells are incubated with a detection molecule (e.g., an antigen of interest) and cells identified by the detection molecule are isolated. Immunoglobulin DNA from the isolated cells is amplified and reintroduced into cells. The cells are incubated again with the detection molecule and cells bound by the detection molecule are isolated. One or more rounds of selection can enrich for antibodies or fragments thereof with the desired specificity to the target of interest. Thus, rare cells expressing a desired antibody molecule can be selected from a large, highly diverse population.

As described herein, in some embodiments the polypeptide of the invention comprises an immunoglobulin heavy chain constant region comprising CH2 and CH3 and a transmembrane portion. The polypeptide is capable of covalently associating with an immunoglobulin heavy chain-light chain pair expressed by the antibody-producing cell to form a heterodimeric antibody molecule expressed on the surface of the cell. In some embodiments, the heterodimeric antibody molecule comprises a single antigen-binding site and is a monovalent antibody. The single antigen-binding site of the heterodimeric molecule on an individual cell is representative of the binding specificity of the antibody produced and secreted by the individual cell. Thus identifying a cell with a heterodimeric antibody molecule that binds to a specific antigen of interest, allows for isolation of the cell which also produces a secreted antibody with the same binding specificity.

The antibody-producing cell can be any cell that is producing an antibody, whether the cell naturally produces an antibody (e.g., a B-cell) or whether the cell makes an antibody by recombinant means (e.g., a transfected cell). Thus, in some embodiments, the antibody-producing cell is a B-cell, a plasma cell, a hybridoma, a myeloma, or a recombinant cell. In some embodiments, the antibody-producing cell is a mouse cell. In some embodiments, the antibody-producing cell is a human cell. In some embodiments, the antibody-producing cell is a population of antibody-producing cells. In some embodiments, the antibody-producing cells are from an immunized animal. In some embodiments, the antibody-producing cells are from a naïve animal.

In some embodiments, the antibody-producing cells comprise a plurality of polynucleotides. In some embodiments, the plurality of polynucleotides encodes a plurality of polypeptides comprising immunoglobulin heavy chains. In some embodiments, the plurality of polynucleotides encodes a plurality of polypeptides further comprising immunoglobulin light chains. In some embodiments, the plurality of polynucleotides encodes a plurality of polypeptides comprising a single chain immunoglobulin with an immunoglobulin heavy chain and an immunoglobulin light chain. In some embodiments, the plurality of polynucleotides comprises a DNA library. In some embodiments, the DNA library is generated from cells of an immunized animal. In some embodiments, the DNA library is generated from cells of a naïve animal. In some embodiments, the DNA library is a naïve library. In other embodiments, the DNA library is a cDNA library.

The methods provided herein do not limit the type of antibody that is produced by the antibody-producing cells. Thus, in some embodiments, the antibody made by the antibody-producing cell is a recombinant antibody, a monoclonal antibody, a chimeric antibody, a humanized antibody, a human antibody, a single chain antibody, or an antibody fragment. In some embodiments, the antibody made by the antibody-producing cell is a monospecific antibody or a multispecific antibody (e.g., a bispecific antibody). In some embodiments, the antibody made by the antibody-producing cell is an IgA, IgD, IgE, IgG or IgM antibody or a subtype thereof. In some embodiments, the antibody made by the antibody-producing cell is an IgG1 or IgG2 antibody. In some embodiments, the antibody made by the antibody-producing cell is an IgG2 antibody. In some embodiments, the antibody is a murine antibody. In some embodiments, the antibody made by the antibody-producing cell is a humanized antibody. In other embodiments, the antibody is a human antibody.

In some embodiments, the method of identifying a cell that produces a specific antibody comprises transfecting cells comprising a novel polypeptide described herein with at least one polynucleotide encoding at least one additional polypeptide. In some embodiments, the transfected cells express a heterodimeric antibody molecule on the surface of the cells. In some embodiments, the method comprises contacting the transfected cells with a detection molecule. In some embodiments, the method comprises identifying the transfected cells that are bound by the detection molecule. In some embodiments, the method comprises isolating the cells that bound by the detection molecule. In some embodiments, the detection molecule is a target of interest. In some embodiments, the detection molecule is a protein or fragment thereof. In some embodiments, the detection molecule is labeled.

In some embodiments, the at least one polynucleotide comprises a plurality of polynucleotides that encode a plurality of polypeptides. In some embodiments, the plurality of polynucleotides encodes a plurality of polypeptides comprising an immunoglobulin heavy chain. In some embodiments, the plurality of polynucleotides encodes a plurality of polypeptides further comprising an immunoglobulin light chain. In some embodiments, the plurality of polynucleotides encodes a plurality of polypeptides comprising a single chain immunoglobulin with an immunoglobulin heavy chain and an immunoglobulin light chain. In some embodiments, the plurality of polynucleotides comprises a DNA library. In some embodiments, the DNA library is generated from cells of an immunized animal. In some embodiments, the DNA library is generated from cells of a naïve animal. In some embodiments, the DNA library is a naïve library. In other embodiments, the DNA library is a cDNA library.

In some embodiments, the at least one polynucleotide encodes a polypeptide that is a recombinant antibody, a monoclonal antibody, a chimeric antibody, a humanized antibody, a human antibody, a single chain antibody, or an antibody fragment. In some embodiments, the at least one polynucleotide encodes a polypeptide that is a monospecific antibody or a multispecific antibody (e.g., a bispecific antibody). In some embodiments, the at least one polynucleotide encodes a polypeptide that is an IgA, IgD, IgE, IgG or IgM antibody or a subtype thereof. In some embodiments, the at least one polynucleotide encodes a polypeptide that is an IgG1 or IgG2 antibody. In some embodiments, the at least one polynucleotide encodes a polypeptide that is an IgG2 antibody. In some embodiments, the at least one polynucleotide encodes a polypeptide that is a murine antibody. In some embodiments, the at least one polynucleotide encodes a polypeptide that is a humanized antibody. In other embodiments, the at least one polynucleotide encodes a polypeptide that is a human antibody.

In some embodiments, the method of identifying a cell that produces a specific antibody comprises transfecting a cell library with a polynucleotide or vector encoding any of the novel polypeptides described herein, wherein the cell library comprises antibody-producing cells. In some embodiments, the transfected cells express a heterodimeric antibody molecule on the surface of the cells. In some embodiments, the method comprises contacting the transfected cells with a detection molecule. In some embodiments, the method comprises identifying the transfected cells that are bound by the detection molecule. In some embodiments, the method comprises isolating the cells that bound by the detection molecule. In some embodiments, the detection molecule is a target of interest. In some embodiments, the detection molecule is a protein or fragment thereof. In some embodiments, the detection molecule is labeled.

In some embodiments, the cell library is B-cells, plasma cells, hybridomas, myelomas, or recombinant cells. In some embodiments, the cell library is a hybridoma library. In some embodiments, the cell library comprises mouse cells. In some embodiments, the cell library comprises human cells.

In some embodiments, the methods provided herein produce cells or hybridomas that secrete a specific antibody but also express on their cell surface a monovalent heterodimeric antibody molecule that contains a single antigen-binding site representative of the binding specificity of the secreted antibody. This heterodimeric antibody molecule, and hence the antibody-producing cell, can be identified using a detection molecule. In some embodiments, the detection molecule is an antigen of interest. In some embodiments, the detection molecule is a protein or fragment thereof. In some embodiments, the detection molecule is labeled. In some embodiments, the detection molecule is labeled with a fluorophore, a chromophore or a magnetic compound. In some embodiments, the cells bound with the detection molecule are identified by flow cytometry. In some embodiments, the cells bound with the detection molecule are isolated by FACS.

The novel polypeptides, cells, and cell libraries of the present invention can be used in methods of screening for an antibody specific for an antigen or target of interest. In some embodiments, a method of screening for a specific antibody comprises screening the cells or cell libraries that are described herein. In some embodiments, the cells (e.g., cell library) express a heterodimeric molecule on the surface of the cells. As described herein, the heterodimeric molecule expressed on the surface of the cell comprises a binding site that is the same as the binding site of an antibody produced by the cell. In some embodiments, the method of screening for a specific antibody comprises contacting the cells with a detection molecule. The cells expressing a heterodimeric molecule bound by the detection molecule express an antibody molecule specific for the detection molecule. In some embodiments, the method of screening comprises identifying the cells that are bound by the detection molecule. In some embodiments, the method of screening comprises isolating the cells that are bound by the detection molecule. In some embodiments, the method of screening comprises isolating the antibody produced by the cells that are bound by the detection molecule. In some embodiments, the detection molecule is a target of interest. In some embodiments, the detection molecule is a protein or fragment thereof. In some embodiments, the detection molecule is labeled.

In some embodiments, screening for specific antibodies using the Membrane-MAb technique involves iterative rounds of selection followed by amplification. For example, cells (e.g., 293-hMT cells or 293T-hMT cells) are transfected with library DNA. The amount of DNA and the number of cells used for any one transfection will depend on the library and/or library diversity. Once transfected, cells are incubated and allowed to grow for 24-48 hours. Cells are then harvested, washed, and screened with a target molecule (e.g., an antigen of interest). The screening molecule may be directly labeled or may be detected by a second molecule which is labeled. The labeled cells are analyzed and/or sorted using methods known to one of skill in the art, for example, by FACS or by using magnetic beads. Plasmid DNA from the sorted cells is extracted and amplified. Plasmid DNA may be extracted and purified by any wellknown method. For example, plasmid DNA can be extracted using a phenol/chloroform mixture and then ethanol precipitated. The purified plasmid DNA is then used to transform bacteria and amplify the isolated DNA. Or DNA may be isolated from the cells and specific regions amplified by PCR methods known to those of skill in the art. PCR products are subcloned back into the host plasmid which is used to transform bacteria and amplify the plasmid. Using either method, the resulting amplified library output from the first selection is used to transfect fresh cells (e.g., 293-hMT or 293T-hMT cells) and a subsequent round of selection with the same target or antigen is performed. In this manner multiple rounds of selection are performed until the population of antibodies that specifically bind the target or antigen of interest is enriched.

Once the library has been enriched for a population of specific antibody molecules, DNA is isolated and used to transform bacteria. Single colonies are picked and plasmid DNA is isolated. The clonal plasmids are used to transfect mammalian cells (e.g., parental HEK-293 or parental 293T cells) for the production of soluble antibody. The resulting antibody is then tested for specific binding to the desired target by ELISA, FACS and/or Biacore.

Transient transfection of mammalian cells with a plasmid generally results in multiple copies of plasmid per cell. The copy number per cell can range from 100-10,000. The absolute number per cell depends on a variety of factors including, but not limited to, transfection protocol, transfection reagents, plasmid quality, plasmid size, and cellular density. In generating libraries of cell surface-displayed antibodies it is desirable to modulate the amount of antibody-encoding plasmid (or Ab library plasmid) introduced into the cell. In some embodiments, to modulate the plasmid copy number of Ab library plasmid in cells, a separate "carrier" plasmid may be used. The carrier plasmid is mixed with the Ab library plasmid and may take up some of the available "plasmid space". Thus in some embodiments, to modulate the number of Ab library plasmids taken up by the cells, carrier plasmid is mixed with the Ab library plasmid at different ratios and then transfected into cells.

In some embodiments, a method of modulating expression of a polypeptide on the surface of a host cell comprises transfecting into a host cell (a) DNA encoding a polypeptide, and (b) an excess amount of irrelevant DNA. In some embodiments, the polypeptide is a heterodimeric antibody molecule. Thus in some embodiments, a method of modulating expression of a heterodimeric antibody molecule on the surface of a host cell comprises transfecting into a host cell (a) DNA encoding an immunoglobulin, and (b) an excess amount of irrelevant DNA. In some embodiments, the ratio of DNA encoding an immunoglobulin to irrelevant DNA is from 1:10 to 1:1,000,000. In some embodiments, the ratio of DNA encoding an immunoglobulin to irrelevant DNA is 1:10, 1:100, 1:1000, 1:10,000, 1:100,000, 1:1,000,000, or any ratio in between. In some embodiments, the DNA encoding an immunoglobulin is plasmid DNA and the irrelevant DNA is plasmid DNA. In some embodiments, the host cell comprises any of the polypeptides or polynucleotides described herein. In some embodiments, the immunoglobulin comprises an immunoglobulin heavy chain. In some embodiments, the antibody comprises an immunoglobulin light chain. In some embodiments, the immunoglobulin is a single chain antibody molecule with an immunoglobulin heavy chain and an immunoglobulin light chain. In some embodiments, the DNA encoding an immunoglobulin is a DNA library. In some embodiments, the DNA library is generated from cells of an immunized animal. In some embodiments, the DNA library is generated from cells of a naïve animal. In some embodiments, the DNA library is a cDNA library. In some embodiments, the method further comprises contacting the host cell with a detection molecule. In some embodiments, the method comprises identifying the host cells that are bound by the detection molecule. In some embodiments, the method comprises isolating the host cells that are bound by the detection molecule.

Also provided in the present invention are antibodies produced by a cell identified, selected, and/or isolated by any of the methods described herein. Also provided in the present invention are antibodies produced by a cell isolated by any of the methods described herein.

V. Antibodies

As described herein the novel polypeptides and cells of the present invention may be used to identify, select, and/or isolate antibodies that specifically bind targets (e.g., antigens) of interest. In some embodiments, the heterodimeric antibody molecules expressed on the surface of the cells comprise an immunoglobulin heavy chain-light chain pair that forms a single antigen-binding site. The single antigen-binding site is identical to, and/or representative of, the antigen-binding sites on the antibodies produced and secreted by the cells.

The polypeptides, cells and methods provided herein do not limit the type of antibody that is produced. In some embodiments, the antibodies are monoclonal antibodies. Monoclonal antibodies can be prepared using hybridoma methods known to one of skill in the art (see e.g., Kohler and Milstein, 1975, *Nature* 256:495). In some embodiments, a mouse, hamster, or other appropriate host animal, is immunized by multiple subcutaneous, intraperitoneal or intravenous injections of the relevant antigen (e.g., a purified peptide fragment, full-length recombinant protein, fusion protein, etc.). The antigen can be optionally conjugated to a carrier protein such as keyhole limpet hemocyanin (KLH) or serum albumin. The antigen (with or without a carrier protein) is diluted in sterile saline and usually combined with an adjuvant (e.g., Complete or Incomplete Freund's Adjuvant) to form a stable emulsion. In some embodiments, the immunizing antigen can be a human protein or a portion thereof. In some embodiments, the immunizing antigen can be a mouse protein or a portion thereof. In some embodiments, a mouse is immunized with a human antigen. In some embodiments, a mouse is immunized with a mouse antigen. In some embodiments, isolated lymphocytes can be immunized in vitro. In some embodiments, the isolated lymphocytes are non-specifically activated. In some embodiments, the isolated lymphocytes are mouse lymphocytes. In some embodiments, the isolated lymphocytes are human lymphocytes.

Following immunization and/or activation, lymphocytes are isolated and fused with a suitable cell line using, for example, polyethylene glycol to produce hybridomas. The cell line used to produce a hybridoma may include any of the cell lines expressing a novel polypeptide described herein. In some embodiments, the hybridoma cells are selected using specialized media as known in the art and unfused lymphocytes and fusion cells do not survive the selection process. In some embodiments, hybridomas that produce monoclonal antibodies directed against a chosen antigen may be identified by a variety of techniques including, but not limited to, immunoprecipitation, immunoblotting, and in vitro binding assays (e.g., flow cytometry (FACS), enzyme-linked immunosorbent assay (ELISA), radioimmunoassay (RIA)). In other embodiments, the cells are directly selected based upon the antigen binding site expressed on the surface of the cells as part of a heterodimeric antibody molecule using any of the methods as described herein. Hybridomas can be propagated either in in vitro culture using standard methods (Goding, Monoclonal Antibodies: Principles and Practice, Academic Press, 1986) or in in vivo as ascites in an animal. The monoclonal antibodies can be purified from the culture medium or ascites fluid according to standard methods in the art including, but not limited to, affinity chromatography, ion-exchange chromatography, gel electrophoresis, and dialysis.

Alternatively, monoclonal antibodies can be made using recombinant DNA techniques as known to one skilled in the art (see e.g., U.S. Pat. No. 4,816,567). In some embodiments, polynucleotides encoding a monoclonal antibody are isolated from mature B-cells or hybridoma cells, using techniques such as RT-PCR with oligonucleotide primers that specifically amplify the genes encoding the heavy and light chains of antibodies. The sequences of the isolated polynucleotides can be determined using conventional sequencing techniques. The isolated polynucleotides encoding the heavy and light chains can be cloned into suitable expression vectors. These expression vectors produce the monoclonal antibodies when transfected into host cells such as E. coli, simian COS cells, Chinese hamster ovary (CHO) cells, human embryonic kidney cells (HEK), or myeloma cells that do not otherwise produce immunoglobulin proteins. In some embodiments, isolated polynucleotides encoding heavy and light chains are transfected into the cells of the present invention that express the polypeptide comprising an immunoglobulin heavy chain region comprising CH2 and CH3 domains and a transmembrane portion.

Recombinant monoclonal antibodies, or fragments thereof, can also be isolated from phage display libraries expressing CDRs of the desired species (see e.g., McCafferty et al., 1990, Nature, 348:552-554; Clackson et al., 1991, Nature, 352:624-628; and Marks et al., 1991, J. Mol. Biol., 222:581-597).

The polynucleotide(s) encoding a monoclonal antibody can be further modified using recombinant DNA technology to generate alternative antibodies. In some embodiments, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, and/or other biological characteristics of a monoclonal antibody. In some embodiments, site-directed mutagenesis of the CDRs can be used to optimize specificity, affinity, and/or other biological characteristics of a monoclonal antibody.

In some embodiments, the antibody is a humanized antibody. Typically, humanized antibodies are human immunoglobulins in which residues from the complementary determining regions (CDRs) are replaced by residues from CDRs of a non-human species (e.g., mouse, rat, rabbit, hamster) that have the desired specificity, affinity, and/or capability using methods known to one skilled in the art. In some embodiments, the Fv framework region (FR) residues of a human immunoglobulin are replaced with the corresponding framework region residues from a non-human immunoglobulin that has the desired specificity, affinity, and/or capability. In some embodiments, the humanized antibody can be further modified by the substitution of additional residues either in the Fv framework region and/or within the replaced non-human residues to refine and optimize antibody specificity, affinity, and/or capability. In general, the humanized antibody will comprise substantially all of at least one, and typically two or three, variable domains containing all, or substantially all, of the CDRs that correspond to the non-human immunoglobulin whereas all, or substantially all, of the framework regions are those of a human immunoglobulin consensus sequence. In some embodiments, the humanized antibody can also comprise at least a portion of an immunoglobulin constant region or domain (Fc), typically that of a human immunoglobulin. In certain embodiments, such humanized antibodies are used therapeutically because they may reduce antigenicity and HAMA (human anti-mouse antibody) responses when administered to a human subject. One skilled in the art would be able to obtain a functional humanized antibody with reduced immunogenicity following known techniques (see for example U.S. Pat. Nos. 5,225,539; 5,585,089; 5,693,761; and 5,693,762).

In certain embodiments, the antibody is a human antibody. Human antibodies can be directly prepared using various techniques known in the art. Immortalized human B lymphocytes, immunized in vitro or isolated from an immunized individual, that produce an antibody directed against a target antigen can be generated. Alternatively, a human antibody can be selected from a phage library, where that phage library expresses human antibodies (see e.g., Vaughan et al., 1996, Nat. Biotech., 14:309-314; Sheets et al., 1998, PNAS, 95:6157-6162; Hoogenboom and Winter, 1991, J.

*Mol. Biol.*, 227:381; and Marks et al., 1991, *J. Mol. Biol.*, 222:581). Techniques for the generation and use of antibody phage libraries are also described in U.S. Pat. Nos. 5,969, 108; 6,172,197; 5,885,793; 6,521,404; 6,544,731; 6,555, 313; 6,582,915; 6,593,081; 6,300,064; 6,653,068; 6,706, 484; and 7,264,963; and Rothe et al., 2008, *J. Mol. Bio.*, 376:1182-1200. Affinity maturation strategies and chain shuffling strategies are known in the art and may be employed to generate high affinity human antibodies. (Marks et al., 1992, *Bio/Technology*, 10:779-783).

Human antibodies can also be made in transgenic mice containing human immunoglobulin loci that are capable, upon immunization, of producing the full repertoire of human antibodies in the absence of endogenous immunoglobulin production. This approach is described in U.S. Pat. Nos. 5,545,807; 5,545,806; 5,569,825; 5,625,126; 5,633, 425; and 5,661,016.

In certain embodiments, the antibody is a bispecific antibody. Bispecific antibodies are capable of specifically recognizing and binding to at least two different epitopes. The different epitopes can either be within the same molecule or on different molecules. In some embodiments, the antibodies can specifically recognize and bind a first antigen target, as well as a second antigen target, such as an effector molecule on a leukocyte (e.g., CD2, CD3, CD28, or B7) or a Fc receptor (e.g., CD64, CD32, or CD16) so as to focus cellular defense mechanisms to the cell expressing the first antigen target. In some embodiments, the antibodies can be used to direct cytotoxic agents to cells that express a particular target antigen. These antibodies possess an antigen-binding arm and an arm that binds a cytotoxic agent or a radionuclide chelator, such as EOTUBE, DPTA, DOTA, or TETA.

Techniques for making bispecific antibodies are known by those skilled in the art, see for example, Millstein et al., 1983, *Nature*, 305:537-539; Brennan et al., 1985, *Science*, 229:81; Suresh et al., 1986, *Methods in Enzymol.*, 121:120; Traunecker et al., 1991, *EMBO* 1, 10:3655-3659; Shalaby et al., 1992, *J. Exp. Med.*, 175:217-225; Kostelny et al., 1992, *J. Immunol.*, 148:1547-1553; Gruber et al., 1994, 1 *Immunol.*, 152:5368; and U.S. Pat. No. 5,731,168). Bispecific antibodies can be intact antibodies or antibody fragments. Antibodies with more than two valencies are also contemplated. For example, trispecific antibodies can be prepared (Tutt et al., 1991, 1 *Immunol.*, 147:60). Thus, in certain embodiments the antibodies are multispecific.

In some embodiments, the antibody describe herein is a single chain immunoglobulin produced from a single gene construct (see e.g., Lee et al., 1999, *Molecular Immunology*, 36:61-71). The single chain immunoglobulin contains both an immunoglobulin heavy chain and an immunoglobulin light chain in their entirety. For example, the carboxyl end of a light chain is joined, via a Gly-Ser linker peptide, to the amino end of a heavy chain, wherein the light chain comprises a variable region and a constant region and the heavy chain comprises a variable region and CH1, CH2 and CH3. These single chain immunoglobulins form dimeric antibody molecules.

In certain embodiments, the antibodies or other polypeptides described herein may be monospecific.

In certain embodiments, the antibody is an antibody fragment. Antibody fragments may have different functions or capabilities than intact antibodies; for example, antibody fragments can have increased tumor penetration. Various techniques are known for the production of antibody fragments including, but not limited to, proteolytic digestion of intact antibodies. In some embodiments, antibody fragments include a F(ab')2 fragment produced by pepsin digestion of an antibody molecule. In some embodiments, antibody fragments include a Fab fragment generated by reducing the disulfide bridges of an F(ab')2 fragment. In other embodiments, antibody fragments include a Fab fragment generated by the treatment of the antibody molecule with papain and a reducing agent. In certain embodiments, antibody fragments are produced recombinantly. In some embodiments, antibody fragments include Fv or single chain Fv (scFv) fragments. Fab, Fv, and scFv antibody fragments can be expressed in, and secreted from, *E. coli* or other host cells, allowing for the production of large amounts of these fragments. In some embodiments, antibody fragments are isolated from antibody phage libraries as discussed herein. For example, methods can be used for the construction of Fab expression libraries (Huse et al., 1989, Science, 246: 1275-1281) to allow rapid and effective identification of monoclonal Fab fragments with the desired specificity for a protein or derivatives, fragments, analogs or homologs thereof. In some embodiments, antibody fragments are linear antibody fragments as described in U.S. Pat. No. 5,641, 870. In certain embodiments, antibody fragments are monospecific or bispecific. In certain embodiments, the antibody is a scFv. Various techniques can be used for the production of single-chain antibodies specific to a given target antigen (see, e.g., U.S. Pat. No. 4,946,778).

It can further be desirable, especially in the case of antibody fragments, to modify an antibody in order to increase its serum half-life. This can be achieved, for example, by incorporation of a salvage receptor binding epitope into the antibody fragment by mutation of the appropriate region in the antibody fragment or by incorporating the epitope into a peptide tag that is then fused to the antibody fragment at either end or in the middle (e.g., by DNA or peptide synthesis). (See e.g., U.S. Pat. Nos. 6,096, 871 and 6,121,022.)

For the purposes of the present invention, it should be appreciated that modified antibodies, or fragments thereof, can comprise any type of variable region that provides for the association of the antibody with the specific antigen its binds. In this regard, the variable region may be derived from any type of mammal that can be induced to mount a humoral response and generate immunoglobulins against a desired antigen. As such, the variable region of the modified antibodies can be, for example, of human, murine, non-human primate (e.g., cynomolgus monkeys, macaques, etc.) or rabbit origin. In some embodiments, both the variable and constant regions of the modified immunoglobulins are human. In other embodiments, the variable regions of compatible antibodies (usually derived from a non-human source) can be engineered or specifically tailored to improve the binding properties or reduce the immunogenicity of the molecule. In this respect, variable regions useful in the present invention can be humanized or otherwise altered through the inclusion of imported amino acid sequences.

In certain embodiments, the variable domains in both the heavy and light chains are altered by at least partial replacement of one or more CDRs and, if necessary, by partial framework region replacement and sequence modification. Although the CDRs may be derived from an antibody of the same class or even subclass as the antibody from which the framework regions are derived, it is envisaged that the CDRs will be derived from an antibody of a different class and preferably from an antibody from a different species. It may not be necessary to replace all of the CDRs with all of the CDRs from the donor variable region to transfer the antigen binding capacity of one variable domain to another. Rather, it may only be necessary to transfer those residues that are necessary to maintain the activity of the antigen binding site.

Alterations to the variable region notwithstanding, those skilled in the art will appreciate that the modified antibodies of this invention will comprise antibodies (e.g., full-length antibodies or antigen-binding fragments thereof) in which at least a fraction of one or more of the constant region domains has been deleted or otherwise altered so as to provide desired biochemical characteristics, such as increased tumor localization, increased tumor penetration, reduced serum half-life, or increased serum half-life, when compared with an antibody of approximately the same immunogenicity comprising a native or unaltered constant region. In some embodiments, the constant region of the modified antibodies comprises a human constant region. Modifications to the constant region include additions, deletions or substitutions of one or more amino acids in one or more domains. The modified antibodies disclosed herein may comprise alterations or modifications to one or more of the three heavy chain constant domains (CH1, CH2 or CH3) and/or to the light chain constant domain (CL). In some embodiments, one or more domains are partially or entirely deleted from the constant regions of the modified antibodies. In some embodiments, the entire CH2 domain has been removed (ΔCH2 constructs). In some embodiments, the omitted constant region domain is replaced by a short amino acid spacer (e.g., 10 aa residues) that provides some of the molecular flexibility typically imparted by the absent constant region.

In certain embodiments, the modified antibodies are engineered to fuse the CH3 domain directly to the hinge region of the antibody. In other embodiments, a peptide spacer is inserted between the hinge region and the modified CH2 and/or CH3 domains. For example, constructs may be expressed wherein the CH2 domain has been deleted and the remaining CH3 domain (modified or unmodified) is joined to the hinge region with a 5-20 amino acid spacer. Such a spacer may be added to ensure that the regulatory elements of the constant domain remain free and accessible or that the hinge region remains flexible. However, it should be noted that amino acid spacers can, in some cases, prove to be immunogenic and elicit an unwanted immune response against the construct. Accordingly, in certain embodiments, any spacer added to the construct will be relatively non-immunogenic so as to maintain the desired biological qualities of the modified antibodies.

In some embodiments, the modified antibodies may have only a partial deletion of a constant domain or substitution of a few or even a single amino acid. For example, the mutation of a single amino acid in selected areas of the CH2 domain may be enough to substantially reduce Fc binding and thereby increase tumor localization and/or tumor penetration. Similarly, it may be desirable to simply delete a part of one or more constant region domains that control a specific effector function (e.g., complement C1q binding) to be modulated. Such partial deletions of the constant regions may improve selected characteristics of the antibody (serum half-life) while leaving other desirable functions associated with the subject constant region domain intact. Moreover, as alluded to above, the constant regions of the disclosed antibodies may be modified through the mutation or substitution of one or more amino acids that enhances the profile of the resulting construct. In this respect it may be possible to disrupt the activity provided by a conserved binding site (e.g., Fc binding) while substantially maintaining the configuration and immunogenic profile of the modified antibody. In certain embodiments, the modified antibodies comprise the addition of one or more amino acids to the constant region to enhance desirable characteristics such as decreasing or increasing effector function or provide for more cytotoxin or carbohydrate attachment sites.

It is known in the art that the constant region mediates several effector functions. For example, binding of the C1 component of complement to the Fc region of IgG or IgM antibodies (bound to antigen) activates the complement system. Activation of complement is important in the opsonization and lysis of cell pathogens. The activation of complement also stimulates the inflammatory response and can also be involved in autoimmune hypersensitivity. In addition, the Fc region of an antibody can bind to a cell expressing a Fc receptor (FcR). There are a number of Fc receptors that are specific for different classes of antibody, including IgG (gamma receptors), IgE (epsilon receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (ADCC), release of inflammatory mediators, placental transfer and control of immunoglobulin production.

In certain embodiments, the antibodies provide for altered effector functions that, in turn, affect the biological profile of the administered antibody. For example, in some embodiments, the deletion or inactivation (through point mutations or other means) of a constant region domain may reduce Fc receptor binding of the circulating modified antibody thereby increasing tumor localization and/or penetration. In other embodiments, the constant region modifications increase or reduce the serum half-life of the antibody. In some embodiments, the constant region is modified to eliminate disulfide linkages or oligosaccharide moieties allowing for enhanced tumor localization and/or penetration.

In certain embodiments, an antibody does not have one or more effector functions. In some embodiments, the antibody has no antibody-dependent cellular cytoxicity (ADCC) activity and/or no complement-dependent cytoxicity (CDC) activity. In certain embodiments, the antibody does not bind to an Fc receptor and/or complement factors. In certain embodiments, the antibody has no effector function.

The present invention further embraces variants and equivalents that are substantially homologous to the chimeric, humanized and human antibodies, or antibody fragments thereof, set forth herein. These can contain, for example, conservative substitution mutations, i.e. the substitution of one or more amino acids by similar amino acids.

EXAMPLES

Example 1

Generation of Immunoglobulin Constant Region-CD4 Constructs

A construct was designed to contain a signal sequence, a FLAG epitope tag, the hinge region and CH2 and CH3 domains of murine IgG1 and the transmembrane domain (TM) and intracellular domain (ICD) of human CD4, referred to as Membrane-MAb(mIgG1). A second construct was designed to contain a signal sequence, a FLAG epitope tag, the hinge region and CH2 and CH3 domains of human IgG2 and the transmembrane domain (TM) and intracellular domain (ICD) of human CD4, referred to as Membrane-MAb(hIgG2). A third construct was designed to contain a signal sequence, a FLAG epitope tag, the hinge region and CH2 and CH3 domains of human IgG2, the transmembrane domain (TM) and intracellular domain (ICD) of human CD4, and green fluorescent protein (GFP) at the C-terminal end, referred to as Membrane-MAb(hIgG2)-GFP (FIG. 6A).

The portion of the hinge region used in each construct was designed to include the residues C-terminal of the cysteine involved in light chain pairing. The Membrane-MAb (mIgG1) construct was designed in the following order, signal sequence-FLAG-mIgG1 (hinge-CH2-CH3)-hCD4 (TM/ICD) and is shown in SEQ ID NO:24 (nucleotide sequence) and SEQ ID NO:22 (amino acid sequence with signal sequence). The Membrane-MAb(hIgG2) construct was designed in the following order, signal sequence-FLAG-hIgG2 (hinge-CH2-CH3)-hCD4 (TM/ICD) and is shown in SEQ ID NO:25 (nucleotide sequence) and SEQ ID NO:23 (amino acid sequence with signal sequence). The Membrane-MAb(hIgG2)-GFP construct was designed in the following order, signal sequence-FLAG-hIgG2 (hinge-CH2-CH3)-hCD4 (TM/ICD)-GFP and is shown in SEQ ID NO:27 (nucleotide sequence) and SEQ ID NO:26 (amino acid sequence with signal sequence). The Membrane-MAb (hIgG2) and Membrane-Mab(hIgG2)-GFP constructs were designed to have a modification within the CD4 intracellular domain to remove the lck protein binding site. The constructs were generated by chemical synthesis and cloned into mammalian expression vector plasmids by standard techniques.

Example 2

Generation of Cell Line

Figure 2A:
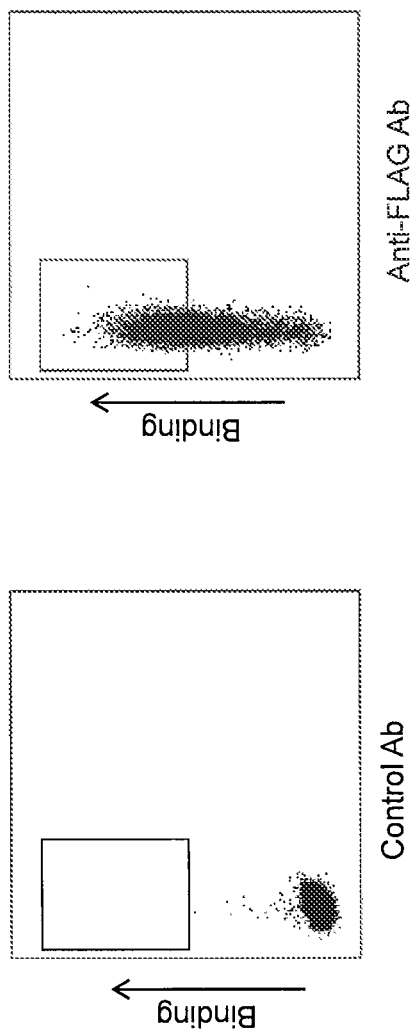

The murine hybridoma fusion partner cell line SP2/0-Ag14 was stably transfected with the Membrane-MAb (mIgG1) construct described in Example 1. $2 \times 10^6$ SP2/0 cells were transfected with 2 ug of the Membrane-MAb (mIgG1) construct using an Amaxa® Nucleofection Kit V (Lonza) following the manufacturer's instructions for program L-013. After 24 hours, the cells were placed under 0.8 mg/ml G418 selection and propagated in culture. Two weeks post-transfection, the cells were characterized by FACS analysis for cell surface expression of the Membrane-MAb (mIgG1) construct. These cells were designated SP2/0-MT. $5 \times 10^6$ transfected cells were incubated with fluorophore-labeled anti-FLAG antibody or an isotype negative control antibody (10 µg/ml) for 30 minutes on ice. The cells were washed, resuspended in DMEM/10% FBS, and were analyzed by flow cytometry. FIG. 2A shows the flow cytometry results with the negative control antibody (left panel) and the number of cells expressing the Membrane-MAb(mIgG1) polypeptide as detected with the anti-FLAG antibody (right panel).

Figure 2B:
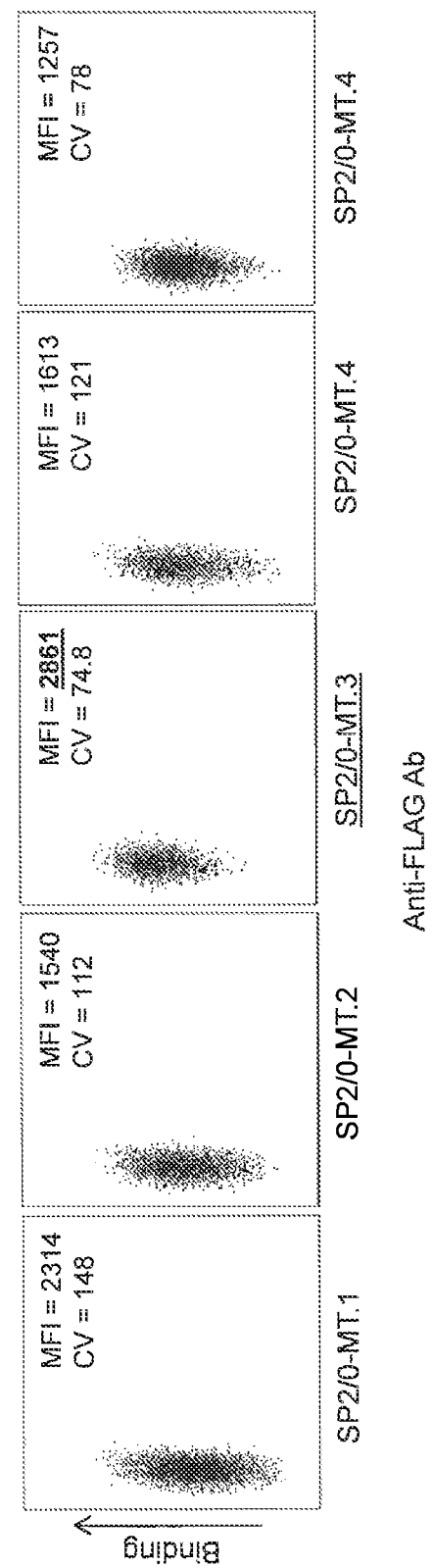

Cells expressing the Membrane-MAb(mIgG1) construct were sorted by FACS at 1 cell per well into 96 well plates and grown in culture under selection with 0.5 mg/ml G418. After 10 days the cell clones from each well were analyzed for expression of the Membrane-MAb(mIgG1) construct by flow cytometry as described above and 5 sub-clones were selected. As shown in FIG. 2B subclone SP2/0-MT.3 was observed to have the highest level of expression of the Membrane-MAb(mIgG1) construct.

Example 3

Use of the Membrane-MAb Technique to Isolate Hybridomas

Recombinant polypeptide fragments of the fri-domain of murine Frizzled 5 (FZD5) and murine Frizzled 8 (FZD8) were generated for use as antigen for antibody production. Standard recombinant DNA technology was used to isolate polynucleotides encoding amino acids 27-157 of FZD5 (SEQ ID NO:19) and amino acids 28-158 of FZD8 (SEQ ID NO:20). The polynucleotides were ligated in-frame N-terminal to a histidine-tag and cloned into a transfer plasmid vector for baculovirus-mediated expression in insect cells. Standard transfection, infection, and cell culture protocols were used to produce recombinant insect cells expressing the corresponding FZD polypeptides.

Mice (n=3) were immunized with both FZD5 and FZD8 antigen proteins using standard techniques. Blood from individual mice was screened approximately 70 days after initial immunization for antigen recognition using ELISA and FACS analysis. The two animals with the highest antibody titers were selected for final antigen boost after which spleen cells were isolated. The isolated splenocytes were fused with the SP2/0-MT cell line described in Example 2 using standard hybridoma fusion techniques. The resulting hybridoma library was named 54L1.

Library 54L1 was screened with labeled FZD5 and labeled FZD8 polypeptides. For labeled FZD5, murine His-tagged fri-domain FZD5 was conjugated to Alexa Fluor™ 488 dye at a 15:1 dye:protein ratio following the manufacturer's protocol (InVitrogen/Molecular Probes). For labeled FZD8, murine His-tagged fri-domain FZD8 was conjugated to Alexa Fluor™ 647 dye at a 15:1 dye:protein ratio following the manufacturer's protocol (InVitrogen/Molecular Probes). The hybridoma cells at $1 \times 10^7$ cells/ml were incubated with Alexa Fluor™ 488-labeled FZD5 (10 µg/ml) and Alexa Fluor 647-labeled FZD8 (10 µg/ml) for 30 minutes at room temperature. The cells were washed, resuspended in DMEM/10% FBS, and were analyzed by flow cytometry (FIG. 3). Individual hybridoma cells bound by both Alexa Fluor 488-labeled FZD5 and Alexa Fluor 647-labeled FZD8 were sorted by FACS at 1 cell per well into 96 well tissue culture plates. As a control, individual cells from the 54L1 library were randomly sorted at 1 cell per a well into 96 wells tissue culture plates. The plates were incubated for 10 days to allow the hybridoma cells to proliferate and the supernatant from each well was screened for the presence of antibody that could bind both FZD5 and FZD8 protein.

For screening by FACS, HEK-293 cells were co-transfected with expression vectors encoding a full-length cDNA clone of FZD5 or FZD8 and the transfection marker GFP. 24 to 48 hours post-transfection, HEK-293 cells were collected and incubated on ice with the anti-FZD5/8 hybridoma supernatants or control IgG. The cells were washed and bound primary antibodies were detected with anti-mouse secondary antibodies conjugated to a fluorescent chromophore. Labeled cells were then analyzed by FACS to identify antibodies that specifically recognized cell surface expression of native FZD5 and/or FZD8.

The use of the SP2/0-MT fusion partner cell line and the Membrane-MAb technique resulted in selection of 526 out of 576 clones (91%) that were capable of binding FZD5 and FZD8. In contrast, the control library screening of random clones resulted in selection of only 11 out of 1705 clones (0.6%) that were capable of binding FZD5 and FZD8 (see Table 1). Thus, use of the Membrane-MAb technique resulted in a dramatic increase identification of hybridomas specific for FZD5 and FZD8.

TABLE 1

| | FACS Positive/Total Clones Tested | Percent Cells Positive |
|---|---|---|
| Random Clones | 11/1705 | 0.6% |
| Sorted Clones | 526/576 | 91% |

As shown in FIG. 3, only a small percentage of the cells in library 54L1 displayed binding to FZD5, FZD8, or both FZD5 and FZD8. The Membrane-MAb technique allowed for direct identification and selection of cells producing an antibody that bound to both FZD5 and FZD8. It should be clear to one of skill in the art that the cells producing antibodies that bind to only FZD5 or only FZD8 could also be selected by the Membrane-MAb technique.

Example 4

Use of the Membrane-MAb Technique to Isolate Hybridomas

A recombinant polypeptide fragment of the extracellular domain of human DDR2 was generated for use as antigen for antibody production. Standard recombinant DNA technology was used to isolate polynucleotides encoding amino acids 1-399 of DDR2 (SEQ ID NO:21). This polynucleotide was ligated in-frame N-terminal to a histidine-tag and cloned into a transfer plasmid vector for baculovirus-mediated expression in insect cells. Standard transfection, infection, and cell culture protocols were used to produce recombinant insect cells expressing the corresponding DDR2 polypeptide.

Mice (n=3) were immunized with purified DDR2 antigen protein using standard techniques. Blood from individual mice was screened approximately 70 days after initial immunization for antigen recognition using ELISA and FACS analysis. The two animals with the highest antibody titers were selected for final antigen boost after which spleen cells were isolated and used to produce a DDR2 hybridoma library by standard hybridoma fusion techniques.

Figure 4:
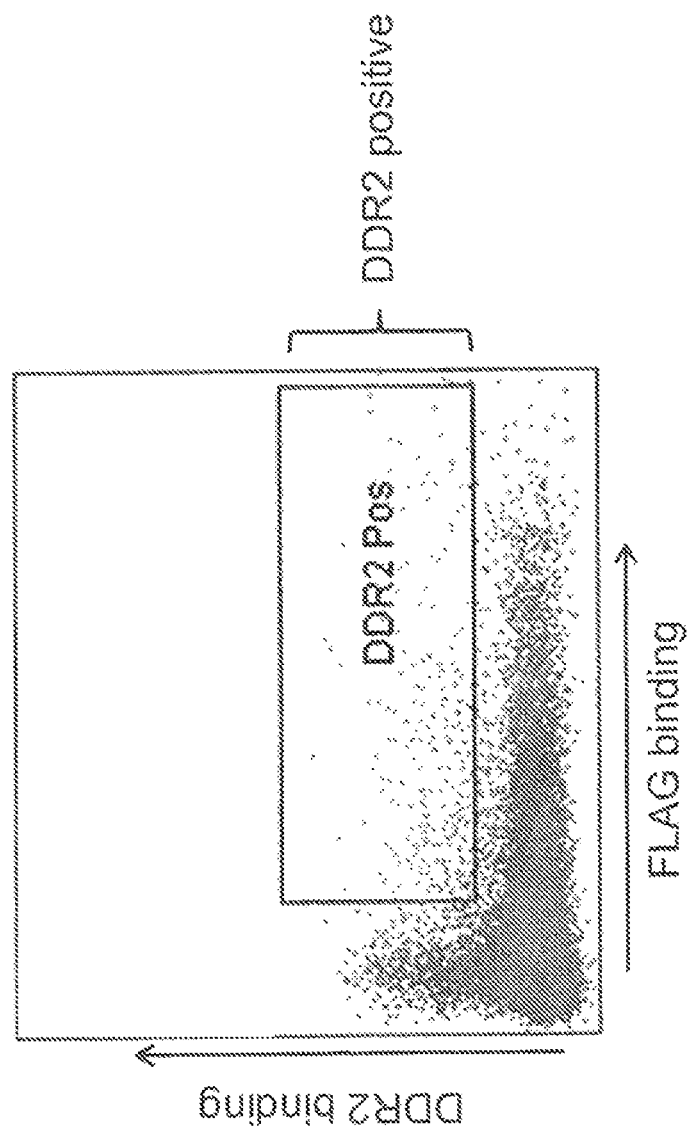

A portion of the DDR2 library was transfected with the Membrane-MAb(mIgG1) construct (described in Example 1). The library was transfected using an Amaxa® Nucleofection Kit V (Lonza) following the manufacturer's instructions for program L-013. $3 \times 10^7$ cells were transfected with 30 µg of Membrane-Mab(mIgG1) construct ("Membrane-MAb library"). After 24 hours, the transfected cells were screened with labeled DDR2 polypeptide. For labeled DDR2, DDR2 polypeptide (as prepared above) was conjugated to Alexa Fluor™ 488 carboxylic acid succinimidyl ester dye at a 15:1 dye:protein ratio following the manufacturer's protocol (InVitrogen/Molecular Probes). The Membrane-MAb library at $1 \times 10^7$ cells/ml was incubated with Alexa Fluor 488-labeled DDR2 (20 µg/ml) and PE-labeled anti-FLAG antibody (10 µg/ml) for 30 minutes on ice. The cells were washed, resuspended in DMEM/10% FBS, and were analyzed by flow cytometry. As shown in FIG. 4 only a minor percentage of the cells in the library displayed binding to DDR2 and anti-FLAG antibody.

Individual hybridoma cells bound by Alexa Fluor 488-labeled DDR2 and PE-labeled anti-FLAG antibody were sorted by FACS at 1 cell per well into 96 well tissue culture plates. Random individual cells from the same library were deposited into wells of 96 wells tissue culture plates as a control. The plates were incubated for 10 days to allow the hybridoma cells to proliferate and subsequently, the supernatant from each well was screened for the presence of antibody that could bind full-length DDR2 protein.

For screening by FACS, HEK-293 cells were co-transfected with expression vectors encoding a full-length cDNA clone of DDR2 and the transfection marker GFP. 24 to 48 hours post-transfection, HEK-293 cells were collected and incubated on ice with the anti-DDR2 hybridoma supernatants or control IgG. The cells were washed and bound primary antibodies were detected with anti-mouse secondary antibodies conjugated to a fluorescent chromophore. Labeled cells were then analyzed by FACS to identify antibodies that specifically recognized cell surface expression of native DDR2.

The use of the Membrane-MAb technique resulted in selection of 141 out of 168 clones (84%) that were capable of binding DDR2. In contrast, the control library screening of random clones resulted in selection of only 16 out of 202 clones (8%) that were capable of binding DDR2 (see Table 2). Thus, use of the Membrane MAb technique resulted in a dramatic increase in identification of cells producing antigen specific antibodies.

TABLE 2

| | FACS Positive/Total Clones Tested | Percent Cells Positive |
|---|---|---|
| Random Clones | 16/202 | 8% |
| Sorted Clones | 141/168 | 84% |

Example 5

Generation of 293-hMT Cell Line

HEK-293 cells were stably transfected with the Membrane-MAb(hIgG2)-GFP construct to generate a cell line stably expressing the Membrane-MAb(hIgG2)-GFP polypeptide (described in Example 1 and depicted in FIG. 6C). $5 \times 10^6$ HEK-293 cells were transfected with 8µg of the Membrane-MAb(hIgG2)-GFP construct using the FuGENE transfection reagent (Roche, Indianapolis, Ind.) following the manufacturer's instructions. After 24 hours, the cells were placed under 0.8 mg/ml G418 selection and propagated in culture. Two weeks post-transfection, the cells were characterized by FACS analysis for expression of the Membrane-MAb(hIgG2)-GFP construct. Subclones of the transfected cells were screened for GFP expression and FIG. 5 shows the flow cytometry results of ten clones.

Example 6

Single Gene Antibody Construct and Library

A parental antibody scaffold was designed as a single protein or single chain antibody (scAb) construct in which the carboxyl terminus of the constant region of the antibody light chain is linked to the amino terminus of the heavy chain variable region via a $(GGGGS)_6$ peptide linker. Cysteine residues in the hinge region were retained to allow for disulfide linkages between two heavy chains or between one heavy chain and a Membrane-MAb construct. The light chain of the single gene antibody encodes a variable region and a human constant region. The heavy chain of the single gene antibody encodes a variable region and human IgG CH1, CH2 and CH3 domains. An expression vector was constructed to produce the single chain antibody and referred to herein as MAbLib construct. The vector was designed so that the light chain variable region and the heavy chain variable region are each flanked by unique restriction sites that allow for removal of the light chain variable region and/or the heavy chain variable region and insertion of new and different variable regions (as depicted in FIG. 6B). The MAbLib construct can be used to generate a wide variety of single chain antibody (scAb) libraries.

Light chain and heavy chain variable regions were PCR amplified from human cDNA by methods well-known to those of skill in the art. Primers containing the restriction sites EcoRv or BsiWI were used in PCR reactions for light chain variable regions. Primers containing the restriction sites MfeI or BlpI were used in PCR reactions for heavy chain variable regions. PCR products containing light chain variable regions were purified, digested with EcoRv and BsiWI and cloned into a similarly digested parental MAbLib vector (described above). This created a scAb library with diversity in the light chain variable region. Subsequently, PCR products containing heavy chain variable regions were purified, digested with MfeI and BlpI and cloned into a similarly digested scAb library containing the diverse light chain variable region. This created a scAb library with diversity in both the light chain and heavy chain variable regions. One of skill in the art would know that the heavy chain variable region may be inserted into the parental MAbLib vector prior to insertion of the light chain variable region.

Example 7

Expression of Heterodimeric Antibody Molecule on Surface of HEK-293 Cells

To validate formation of a heterodimeric antibody molecule on the surface of cells, HEK-293 cells was transfected with DNA encoding an anti-DLL4 single chain antibody and DNA encoding the Membrane-MAb(hIgG2)-GFP protein. A synthetic polynucleotide encoding the 21M18 light chain, a $(GGGGS)_6$ linker, the 21M18 variable heavy chain and CH1 domain was designed. The polynucleotide was synthesized by DNA2.0 (Menlo Park Calif.) and cloned into MAbLib to generate a vector encoding a single chain 21M18 antibody (sc21M18) as described above in Example 6 (sc21M18 SEQ ID NO:33, nucleotide sequence; SEQ ID NO:34, amino acid sequence). Anti-hDLL4 antibody 21M18 has been previously described in U.S. Pat. No. 7,750,124. sc21M18 plasmid DNA was transfected across a range of concentrations (25, 250, 2500, and 25000 ng/ml) and cells were harvested after 48 hours. As controls, cells were transfected with the sc21M18 DNA only (-▲-), with the Membrane-MAb (hIgG2)-GFP DNA only (-■-), A or not transfected (-◆-). For detection of a functional anti-DLL4 antibody molecule on the cell surface, transfected cells were incubated with an hDLL4-rFc fusion protein. Bound hDLL4-rFc was detected with a PE-labeled anti-rabbit Fc antibody. Cells were analyzed by FACS and mean fluorescence intensities (MFI) of the cell populations were determined. As shown in FIG. 7, only cells transfected with the anti-DLL4 sc21M18 DNA and the Membrane-MAb(hIgG2) DNA (-X-) expressed a membrane bound molecule with a functional binding site that specifically bound the DLL4-rFc protein.

Example 8

Use of Carrier Plasmid to Modulate the Display of Antibody Molecule

Transient transfection of mammalian cells with a plasmid generally results in multiple copies of plasmid per cell. The copy number per cell can range from 100-10,000. The absolute number per cell depends on a variety of factors including, but not limited to, transfection protocol, transfection reagents, plasmid quality, plasmid size, and cellular density. In some embodiments, in generating libraries of cell surface-displayed antibodies it is desirable to modulate the amount of antibody-encoding plasmid (or Ab library plasmid) introduced into the cell. To modulate the plasmid copy number of Ab library plasmid in cells, a separate "carrier" plasmid is used. The carrier plasmid is mixed with the Ab library plasmid and takes up some of the available "plasmid space". To modulate the number of Ab library plasmid taken up by the cells, carrier plasmid is mixed with the Ab library plasmid at different ratios and then transfected into cells.

The effect of carrier plasmid on the transfection and display of an Ab-encoding plasmid was tested. The single chain anti-DLL4 antibody (sc21M18) described above was transfected with varying ratios of carrier plasmid. In this study, the carrier plasmid encoded an irrelevant single protein antibody (sc18R5). The cells were also transfected with the Membrane-MAb(hIgG2)-GFP construct. The concentration of Ab library plasmid in the cells could be inferred from the level of surface expression of the anti-DLL4 antibody molecule. Approximately $5\times10^6$ HEK-293 cells were transfected with plasmid DNA and harvested after 48 hours. The plasmid DNA was a mixture of sc21M18 and sc18R5, wherein the ratio of sc21M18 to sc18R5 varied from 1 to 10,000-fold excess of sc18R5 (1, 10, 100, 1000 or 10,000-fold excess). For detection of a functional anti-DLL4 antibody molecule on the cell surface, transfected cells were incubated with an hDLL4-rFc fusion protein. Bound hDLL4-rFc was detected with a PE-labeled anti-rabbit Fc antibody. The percentage of cells which expressed anti-DLL4 antibody was determined by FACS analysis. Cells were also incubated with a control antigen (hJag-rFc, -■-) or only the PE-labeled anti-rabbit Fc antibody (-▲-). As shown in FIG. 8, the amount of carrier plasmid DNA had a clear effect on the percentage of cells expressing anti-DLL4 antibody on the surface of transfected cells.

Example 9

Method of Screening Antibody Library

A study was performed using anti-DLL4 antibody sc21M18 plasmid DNA to validate the Membrane-Mab technique and selection methods. sc21M18 plasmid DNA was mixed with irrelevant antibody sc18R5 plasmid DNA, where the sc18R5 DNA was in 100,000-fold excess. HEK-293 cells were transfected with $7.5\times10^{-6}$ µg sc21M18 plasmid DNA, 0.75 µg sc18R5 plasmid DNA, 14.3 µg of carrier plasmid (kanamycin plasmid), and 15 µg of a plasmid encoding Membrane-MAb(hIgG2)-GFP. Cells were harvested after 48 hours. For detection of a functional anti-DLL4 antibody on the cell surface, transfected cells were incubated with an hDLL4-rFc fusion protein. Bound hDLL4-rFc was detected with a PE-labeled anti-rabbit Fc antibody. Labeled cells were analyzed and sorted by FACS to identify and isolate anti-DLL4 antibody expressing cells. hJag-rFc was used as a control, as this antigen will not be recognized by the anti-DLL4 antibody. Plasmid DNA from FACS-sorted cells was isolated and amplified in bacteria. The amplified plasmid DNA (in combination with the carrier plasmid and plasmid encoding Membrane-MAb(hIgG2)-GFP) was used to transfect fresh HEK-293 cells and another round of selection was performed. This process of amplification and selection was iterated for 4 rounds and FACS results are shown in FIG. 9. Table 3 shows the percentage of cells positive for expression of anti-DLL4 antibody after each round of selection. This study demonstrated that cells expressing anti-DLL4 antibody were identified and enriched over 4 rounds of selection, despite the fact that the sc21M18 DNA had been highly diluted in a background of irrelevant antibody DNA.

TABLE 3

| Round | Plasmid Concentration (µg) sc21M18 or previous round | sc18R5 | Kanamycin | MAb(hIgG2) | % Anti-DLL4 Antibody Positive Cells hDLL4-rFc | hJag1-rFc | No antigen |
|---|---|---|---|---|---|---|---|
| 1 | $7.5 \times 10^{-6}$ | 0.75 | 14.3 | 15 | 0.1 | 0.23 | ND |
| 2 | 0.75 Round 1 | 0 | 15 | 15 | 0.23 | 0.78 | 0.002 |
| 3 | 0.75 Round 2 | 0 | 15 | 15 | 0.9 | 0.08 | ND |
| 4a | 0.75 Round 3 | 0 | 15 | 15 | 2.9 | 0.14 | 0.08 |
| 4b | 7.0 Round 3 | 0 | 0 | 0 | 32.8 | 0.43 | 0.0012 |

Example 10

Generation of an Anti-VEGF Antibody Library and Transfection into 293-hMT Cell Line An antibody library was generated using a MAbLib construct expressing sc21M18 described above in Examples 6 and 7 and immunoglobulin cDNA from mice immunized with human vascular endothelial cell growth factor (hVEGF). Three Balb/c mice were immunized by intraperitoneal injection of hVEGF. The initial injection contained hVEGF in Complete Freund's adjuvant. Subsequent injections contained hVEGF in Incomplete Freund's adjuvant. A total of four intraperitoneal injections were performed over the course of three months. Mice received a final injection of hVEGF in PBS by intravenous tail vein injection. One week after the final injection spleens and lymph nodes were collected from the immunized mice. RNA was isolated and cDNA was generated. DNA encoding murine heavy chain variable regions was amplified by PCR, isolated, and purified. The PCR products were digested with MfeI and BlpI and cloned into a similarly digested sc21M18 construct, thereby replacing the heavy chain variable region of SEQ ID NO:33, with a plurality of murine heavy chain variable regions from hVEGF immunized mice. For this library, the 21M18 light chain was held constant.

A second VEGF library was constructed similar to the library described above with the exception that the 21M18 light chain was replaced with a plurality of human kappa chain variable regions. Human kappa chain variable regions were PCR amplified from pooled human cDNA using human kappa chain specific primers. The PCR products were isolated, purified, and digested with EcoRV and BsiWI and cloned into similarly digested plasmid DNA from the first VEGF library, thereby replacing the 21M18 light chain variable region.

293-hMT Cells were Transfected with the Two Anti-VEGF Antibody Libraries.

It is understood that the examples and embodiments described herein are for illustrative purposes only and that various modifications or changes in light thereof will be suggested to persons skilled in the art and are to be included with the spirit and purview of this application.

All publications, patents and patent applications cited herein are hereby incorporated by reference in their entirety for all purposes to the same extent as if each individual publication, patent or patent application were specifically and individually indicated to be so incorporated by reference.

SEQUENCES

Mouse IgG1 constant region Nucleotide sequence
SEQ ID NO: 1
GGTTGTAAGCCTTGCATATGTACAGTCCCAGAAGTATCATCTGTCTTCATCTTCCCCCCA

AAGCCCAAGGATGTGCTCACCATTACTCTGACTCCTAAGGICACGTGTGTTGTGGTAGAC

ATCAGCAAGGATGATCCCGAGGTCCAGTTCAGCTGGTTTGTAGATGATGTGGAGGTGCAC

ACAGCTCAGACGCAACCCCGGGAGGAGCAGTTCAACAGCACTTTCCGCTCAGTCAGTGAA

CTTCCCATCATGCACCAGGACTGGCTCAATGGCAAGGAGTTCAAATGCAGGGTCAACAGT

GCAGCTTTCCCTGCCCCCATCGAGAAAACCATCTCCAAAACCAAAGGCAGACCGAAGGCT

CCACAGGTGTACACCATTCCACCTCCCAAGGAGCAGATGGCCAAGGATAAAGTCAGTCTG

ACCTGCATGATAACAGACTTCTTCCCTGAAGACATTACTGTGGAGTGGCAGTGGAATGGG

CAGCCAGCGGAGAACTACAAGAACACTCAGCCCATCATGGACACAGATGGCTCTTACTTC

GTCTACAGCAAGCTCAATGTGCAGAAGAGCAACTGGGAGGCAGGAAATACTTTCACCTGC

TCTGTGTTACATGAGGGCCTGCACAACCACCATACTGAGAAGAGCCTCTCCCACTCTCCT

GGTAAA

Mouse IgG1 constant region Amino acid sequence
SEQ ID NO: 2
GCKPCICTVPEVSSVFIFPPKPKDVLTITLTPKVTCVVVDISKDDPEVQFSWFVDDVEVH

TAQTQPREEQFNSTFRSVSELPIMHQDWLNGKEFKCRVNSAAFPAPIEKTISKTKGRPKA

PQVYTIPPPKEQMAKDKVSLTCMITDFFPEDITVEWQWNGQPAENYKNTQPIMDTDGSYF

VYSKLNVQKSNWEAGNTFTCSVLHEGLHNHHTEKSLSHSPGK

Mouse IgG2a constant region Nucleotide sequence
SEQ ID NO: 3
ATCAAGCCCTGTCCTCCATGCAAATGCCCAGCACCTAACCTCTTGGGTGGACCATCCGTC

TTCATCTTCCCTCCAAAGATCAAGGATGTACTCATGATCTCCCTGAGCCCCATAGTCACA

TGTGTGGTGGTGGATGTGAGCGAGGATGACCCAGATGTCCAGATCAGCTGGTTTGTGAAC

AACGTGGAAGTACACAGCTCAGACACAAACCCATAGAGAGGATTACAACAGTACTCTC

CGGGTGGTCAGTGCCCTCCCCATCCAGCACCAGGACTGGATGAGTGGCAAGGAGTTCAAA

TGCAAGGTCAACAACAAAGACCTGCCAGCGCCCATCGAGAGAACCATCTCAAAACCCAAA

GGGTCAGTAAGAGCTCCACAGGTATATGTCTTGCCTCCACCAGAAGAAGAGATGACTAAG

AAACAGGTCACTCTGACCTGCATGGTCACAGACTTCATGCCTGAAGACATTTACGTGGAG

TGGACCAACAACGGGAAAACAGAGCTAAACTACAAGAACACTGAACCAGTCCTGGACTCT

GATGGTTCTTACTTCATGTACAGCAAGCTGAGAGTGGAAAAGAAGAACTGGGTGGAAAGA

AATAGCTACTCCTGTTCAGTGGTCCACGAGGGTCTGCACAATCACCACACGACTAAGAGC

TTCTCCCGGACTCCGGGTAAA

Mouse IgG2a constant region Amino acid sequence
SEQ ID NO: 4
IKPCPPCKCPAPNLLGGPSVFIFPPKIKDVLMISLSPIVTCVVVDVSEDDPDVQISWFVN

NVEVHTAQTQTHREDYNSTLRVVSALPIQHQDWMSGKEFKCKVNNKDLPAPIERTISKPK

GSVRAPQVYVLPPPEEEMTKKQVTLTCMVTDFMPEDIYVEWTNNGKTELNYKNTEPVLDS

DGSYFMYSKLRVEKKNWVERNSYSCSVVHEGLHNHHTTKSFSRTPGK

Human IgG1 constant region Nucleotide sequence
SEQ ID NO: 5
ACTCACACATGCCCACCGTGCCCAGCACCTGAACTCCTGGGGGGACCGTCAGTCTTCCTC

TTCCCCCCAAAACCCAAGGACACCCTCATGATCTCCCGGACCCCTGAGGTCACATGCGTG

GTGGTGGACGTGAGCCACGAAGACCCTGAGGTCAAGTTCAACTGGTACGTGGACGGCGTG

GAGGTGCATAATGCCAAGACAAAGCCGCGGGAGGAGCAGTACAACAGCACGTACCGTGTG

-continued

```
GTCAGCGTCCTCACCGTCCTGCACCAGGACTGGCTGAATGGCAAGGAGTACAAGTGCAAG

GTCTCCAACAAAGCCCTCCCAGCCCCCATCGAGAAAACCATCTCCAAAGCCAAAGGGCAG

CCCCGAGAACCACAGGTGTACACCCTGCCCCCATCCCGGGATGAGCTGACCAAGAACCAG

GTCAGCCTGACCTGCCTGGTCAAAGGCTTCTATCCCAGCGACATCGCCGTGGAGTGGGAG

AGCAATGGGCAGCCGGAGAACAACTACAAGACCACGCCTCCCGTGCTGGACTCCGACGGC

TCCTTCTTCCTCTACAGCAAGCTCACCGTGGACAAGAGCAGGTGGCAGCAGGGGAACGTC

TTCTCATGCTCCGTGATGCATGAGGCTCTGCACAACCACTACACGCAGAAGAGCCTCTCC

CTGTCTCCGGGTAAA
```

Human IgG1 constant region Amino acid sequence
SEQ ID NO: 6

```
THTCPPCPAPELLGGPSVFLFPPKPKDTLMISRTPEVTCVVVDVSHEDPEVKFNWYVDGV

EVHNAKTKPREEQYNSTYRVVSVLTVLHQDWLNGKEYKCKVSNKALPAPIEKTISKAKGQ

PREPQVYTLPPSRDELTKNQVSLTCLVKGFYPSDIAVEWESNGQPENNYKTTPPVLDSDG

SFFLYSKLTVDKSRWQQGNVFSCSVMHEALHNHYTQKSLSLSPGK
```

Human IgG2 constant region Nucleotide sequence
SEQ ID NO: 7

```
TGTGTCGAGTGCCCACCTTGCCCAGCACCACCTGTGGCAGGACCTTCAGTCTTCCTCTTC

CCCCCAAAACCCAAGGACACCCTCATGATCTCCCGGACCCCTGAGGTCACATGCGTGGTG

GTGGACGTGAGCCACGAAGACCCCGAGGTCCAGTTTAATTGGTATGTCGACGGCGTGGAG

GTGCATAATGCCAAGACAAAGCCACGGGAGGAGCAGTTCAACAGCACATTCAGGGTGGTC

AGCGTCCTCACCGTTGTGCACCAGGACTGGCTGAACGGCAAGGAGTACAAGTGCAAGGTG

TCCAACAAAGGCCTCCCAGCCCCCATCGAGAAAACCATCTCCAAAACCAAAGGGCAGCCC

AGAGAACCACAGGTGTACACCCTGCCCCCATCCCGGGAGGAGATGACCAAGAACCAGGTC

AGCCTGACCTGCCTGGTGAAGGGATTTTATCCTTCCGACATCGCCGTGGAGTGGGAGAGC

AATGGGCAGCCTGAGAACAACTACAAGACCACACCTCCCATGCTGGACTCCGACGGCTCC

TTCTTCCTGTATTCCAAACTCACCGTGGACAAGAGCAGGTGGCAGCAGGGGAACGTCTTC

TCATGCTCCGTGATGCATGAGGCTCTGCACAACCACTACACACAGAAGAGCCTCTCCCTG

TCCCCTGGA
```

Human IgG2 constant region Amino acid sequence
SEQ ID NO: 8

```
CVECPPCPAPPVAGPSVFLFPPKPKDTLMISRTPEVTCVVVDVSHEDPEVQFNWYVDGVE

VHNAKTKPREEQFNSTFRVVSVLTVVHQDWLNGKEYKCKVSNKGLPAPIEKTISKTKGQP

REPQVYTLPPSREEMTKNQVSLTCLVKGFYPSDIAVEWESNGQPENNYKTTPPMLDSDGS

FFLYSKLTVDKSRWQQGNVFSCSVMHEALHNHYTQKSLSLSPG
``` mIgG1-hCD4 construct without signal sequence and without
FLAG tag Nucleotide sequence
SEQ ID NO: 9

```
GCGATCGCGGGTTGTAAGCCTTGCATATGTACAGTCCCAGAAGTATCATCTGTCTTCATC

TTCCCCCCAAAGCCCAAGGATGTGCTCACCATTACTCTGACTCCTAAGGTCACGTGTGTT

GTGGTAGACATCAGCAAGGATGATCCCGAGGTCCAGTTCAGCTGGTTTGTAGATGATGTG

GAGGTGCACACAGCTCAGACGCAACCCCGGGAGGAGCAGTTCAACAGCACTTTCCGCTCA

GTCAGTGAACTTCCCATCATGCACCAGGACTGGCTCAATGGCAAGGAGTTCAAATGCAGG

GTCAACAGTGCAGCTTTCCCTGCCCCCATCGAGAAAACCATCTCCAAAACCAAAGGCAGA

CCGAAGGCTCCACAGGTGTACACCATTCCACCTCCCAAGGAGCAGATGGCCAAGGATAAA

GTCAGTCTGACCTGCATGATAACAGACTTCTTCCCTGAAGACATTACTGTGGAGTGGCAG
```

-continued

```
TGGAATGGGCAGCCAGCGGAGAACTACAAGAACACTCAGCCCATCATGGACACAGATGGC

TCTTACTTCGTCTACAGCAAGCTCAATGTGCAGAAGAGCAACTGGGAGGCAGGAAATACT

TTCACCTGCTCTGTGTTACATGAGGGCCTGCACAACCACCATACTGAGAAGAGCCTCTCC

CACTCTCCTGGTAAAGGGCGCGCCATGGCCCTGATTGTGCTGGGGGGCGTCGCCGGCCTC

CTGCTTTTCATTGGGCTAGGCATCTTCTTCTGTGTCAGGTGCCGGCACCGAAGGCGCCAA

GCAGAGCGGATGTCTCAGATCAAGAGACTCCTCAGTGAGAAGAAGACCTGCCAGTGCCCT

CACCGGTTTCAGAAGACATGTAGCCCCATTTAG
``` mIgG1-hCD4 construct without signal sequence and without
FLAG tag Amino acid sequence
SEQ ID NO: 10

```
AIAGCKPCICTVPEVSSVFIFPPKPKDVLTITLTPKVTCVVVDISKDDPEVQFSWFVDDV

EVHTAQTQPREEQFNSTFRSVSELPIMHQDWLNGKEFKCRVNSAAFPAPIEKTISKTKGR

PKAPQVYTIPPPKEQMAKDKVSLTCMITDFFPEDITVEWQWNGQPAENYKNTQPIMDTDG

SYFVYSKLNVQKSNWEAGNTFTCSVLHEGLHNHHTEKSLSHSPGKGRAMALIVLGGVAGL

LLFIGLGIFFCVRCRHRRRQAERMSQIKRLLSEKKTCQCPHRFQKTCSPI
``` hIgG2-hCD4* construct without signal sequence and without
FLAG tag Nucleotide sequence
SEQ ID NO: 11

```
GCGATCGCGAACGGATGTGTCGAGTGCCCACCTTGCCCAGCACCACCTGTGGCAGGACCT

TCAGTCTTCCTCTTCCCCCCAAAACCCAAGGACACCCTCATGATCTCCCGGACCCCTGAG

GTCACATGCGTGGTGGTGGACGTGAGCCACGAAGACCCCGAGGTCCAGTTTAATTGGTAT

GTCGACGGCGTGGAGGTGCATAATGCCAAGACAAAGCCACGGGAGGAGCAGTTCAACAGC

ACATTCAGGGTGGTCAGCGTCCTCACCGTTGTGCACCAGGACTGGCTGAACGGCAAGGAG

TACAAGTGCAAGGTGTCCAACAAAGGCCTCCCAGCCCCCATCGAGAAAACCATCTCCAAA

ACCAAAGGGCAGCCCAGAGAACCACAGGTGTACACCCTGCCCCCATCCCGGGAGGAGATG

ACCAAGAACCAGGTCAGCCTGACCTGCCTGGTGAAGGGATTTTATCCTTCCGACATCGCC

GTGGAGTGGGAGAGCAATGGGCAGCCTGAGAACAACTACAAGACCACACCTCCCATGCTG

GACTCCGACGGCTCCTTCTTCCTGTATTCCAAACTCACCGTGGACAAGAGCAGGTGGCAG

CAGGGGAACGTCTTCTCATGCTCCGTGATGCATGAGGCTCTGCACAACCACTACACACAG

AAGAGCCTCTCCCTGTCCCCTGGAAAGGGGCGCGCCATGGCCCTGATTGTGCTGGGGGGC

GTCGCCGGCCTCCTGCTTTTCATTGGGCTCGGCATCTTCTTCTGTGTCCGCTGCCGGCAC

CGACGCCGCCAAGCAGAGCGGATGTCTCAGATCAAGAGACTCCTCAGTGAGAAGAAGACC

GCACAGTGCCCTCACCGGTTTCAGAAGACATGTAGCCCCATTTAG
``` hIgG2-hCD4* construct without signal sequence and without
FLAG tag Amino acid sequence
SEQ ID NO: 12

```
AIANGCVECPPCPAPPVAGPSVFLFPPKPKDTLMISRTPEVTCVVVDVSHEDPEVQFNWY

VDGVEVHNAKTKPREEQFNSTFRVVSVLTVVHQDWLNGKEYKCKVSNKGLPAPIEKTISK

TKGQPREPQVYTLPPSREEMTKNQVSLTCLVKGFYPSDIAVEWESNGQPENNYKTTPPML

DSDGSFFLYSKLTVDKSRWQQGNVFSCSVMHEALHNHYTQKSLSLSPGKGRAMALIVLGG

VAGLLLFIGLGIFFCVRCRHRRRQAERMSQIKRLLSEKKTAQCPHRFQKTCSPI
```
*CD4 Intracellular domain region is modified, amino acid
change is underlined Human CD4 TM sequence
SEQ ID NO: 13
MALIVLGGVAGLLLFIGLGIFF Human CD4 TM-ICD sequence

```
                                                    SEQ ID NO: 14
MALIVLGGVAGLLLFIGLGIFFCVRCHRRRQAERMSQIKRLLSEKKTCQCPHRFQKTCSPI

Human CD4 TM-ICD*
                                                    SEQ ID NO: 15
MALIVLGGVAGLLLFIGLGIFFCVRCHRRRQAERMSQIKRLLSEKKTAQCPHRFQKTCSPI
*CD4 Intracellular domain region is modified, amino acid
change is underlined Mouse CD4 TM sequence
                                                    SEQ ID NO: 16
FLACVLGGSFGFLGFLGLCILC Mouse CD4 TM-ICD sequence
                                                    SEQ ID NO: 17
FLACVLGGSFGFLGFLGLCILCCVRCRHQQRQAARMSQIKRLLSEKKTCQCPHRMQKSHNLI FLAG tag
                                                    SEQ ID NO: 18
DYKDDDDK Human FZD5 Fri-domain sequence (Amino acids 27-157)
                                                    SEQ ID NO: 19
ASKAPVCQEITVPMCRGIGYNLTHMPNQFNHDTQDEAGLEVHQFWPLVEIQCSPDLRFFL

CSMYTPICLPDYHKPLPPCRSVCERAKAGCSPLMRQYGFAMPERMSCDRLPVLGRDAEVL

CMDYNRSEATT

Human FZD8 Fri-domain sequence (Amino acids 28-158)
                                                    SEQ ID NO: 20
ASAKELACQEITVPLCKGIGYNYTYMPNQFNHDTQDEAGLEVHQFWPLVEIQCSPDLKFF

LCSMYTPICLEDYKKPLPPCRSVCERAKAGCAPLMRQYGFAWPDRMRCDRLPEQGNPDTL

CMDYNRTDLTT

Human DDR2 Amino acids 1-399
                                                    SEQ ID NO: 21
MILIPRMLLVLFLLLPILSSAKAQVNPAICRYPLGMSGGQIPDEDITASSQWSESTAAKY

GRLDSEEGDGAWCPEIPVEPDDLKEFLQIDLHTLHFITLVGTQGRHAGGHGIEFAPMYKI

NYSRDGTRWISWRNRHGKQVLDGNSNPYDIFLKDLEPPIVARFVRFIPVTDHSMNVCMRV

ELYGCVWLDGLVSYNAPAGQQFVLPGGSIIYLNDSVYDGAVGYSMTEGLGQLTDGVSGLD

DFTQTHEYHVWPGYDYVGWRNESATNGYIEIMFEFDRIRNFTTMKVHCNNMFAKGVKIFK

EVQCYFRSEASEWEPNAISFPLVLDDVNPSARFVTVPLHHRMASAIKCQYHFADTWMMFS

EITFQSDAAMYNNSEALPTSPMAPTTYDPMLKVDDSNTR mIgG1-hCD4 construct with signal sequence and with FLAG
tag Amino Acid sequence
                                                    SEQ ID NO: 22
MSALLILALVGAAVADYKDHDGDYKDHDIDYKDDDDKAIAGCKPCICTVPEVSSVFIFPP

KPKDVLTITLTPKVTCVVVDISKDDPEVQFSWFVDDVEVHTAQTQPREEQFNSTFRSVSE

LPIMHQDWLNGKEFKCRVNSAAFPAPIEKTISKTKGRPKAPQVYTIPPPKEQMAKDKVSL

TCMITDFFPEDITVEWQWNGQPAENYKNTQPIMDTDGSYFVYSKLNVQKSNWEAGNTFTC

SVLHEGLHNHHTEKSLSHSPGKGRAMALIVLGGVAGLLLFIGLGIFFCVRCHRRRQAER

MSQIKRLLSEKKTCQCPHRFQKTCSPI hIgG2-hCD4* construct with signal sequence and with FLAG
tag Amino Acid sequence
                                                    SEQ ID NO: 23
MSALLILALVGAAVADYKDHDGDYKDHDIDYKDDDDKAIANGCVECPPCPAPPVAGPSVF

LFPPKPKDTLMISRTPEVTCVVVDVSHEDPEVQFNWYVDGVEVHNAKTKPREEQFNSTFR

VVSVLTVVHQDWLNGKEYKCKVSNKGLPAPIEKTISKTKGQPREPQVYTLPPSREEMTKN

QVSLTCLVKGFYPSDIAVEWESNGQPENNYKTTPPMLDSDGSFFLYSKLTVDKSRWQQGN

VFSCSVMHEALHNHYTQKSLSLSPGKGRAMALIVLGGVAGLLLFIGLGIFFCVRCHRRR
```

QAERMSQIKRLLSEKKTAQCPHRFQKTCSPI
*CD4 Intracellular domain region is modified, amino acid change is underlined mIgG1-hCD4 construct with signal sequence and with FLAG tag Nucleotide sequence

SEQ ID NO: 24

ATGTCTGCACTTCTGATCCTAGCTCTTGTTGGAGCTGCAGTTGCTGACTACAAAGACCAT

GACGGTGATTATAAAGATCATGACATCGATTACAAGGATGACGATGACAAGGCGATCGCG

GGTTGTAAGCCTTGCATATGTACAGTCCCAGAAGTATCATCTGTCTTCATCTTCCCCCCA

AAGCCCAAGGATGTGCTCACCATTACTCTGACTCCTAAGGTCACGTGTGTTGTGGTAGAC

ATCAGCAAGGATGATCCCGAGGTCCAGTTCAGCTGGTTTGTAGATGATGTGGAGGTGCAC

ACAGCTCAGACGCAACCCCGGGAGGAGCAGTTCAACAGCACTTTCCGCTCAGTCAGTGAA

CTTCCCATCATGCACCAGGACTGGCTCAATGGCAAGGAGTTCAAATGCAGGGTCAACAGT

GCAGCTTTCCCTGCCCCCATCGAGAAAACCATCTCCAAAACCAAAGGCAGACCGAAGGCT

CCACAGGTGTACACCATTCCACCTCCCAAGGAGCAGATGGCCAAGGATAAAGTCAGTCTG

ACCTGCATGATAACAGACTTCTTCCCTGAAGACATTACTGTGGAGTGGCAGTGGAATGGG

CAGCCAGCGGAGAACTACAAGAACACTCAGCCCATCATGGACACAGATGGCTCTTACTTC

GTCTACAGCAAGCTCAATGTGCAGAAGAGCAACTGGGAGGCAGGAAATACTTTCACCTGC

TCTGTGTTACATGAGGGCCTGCACAACCACCATACTGAGAAGAGCCTCTCCCACTCTCCT

GGTAAAGGGCGCGCCATGGCCCTGATTGTGCTGGGGGGCGTCGCCGGCCTCCTGCTTTTC

ATTGGGCTAGGCATCTTCTTCTGTGTCAGGTGCCGGCACCGAAGGCGCCAAGCAGAGCGG

ATGTCTCAGATCAAGAGACTCCTCAGTGAGAAGAAGACCTGCCAGTGCCCTCACCGGTTT

CAGAAGACATGTAGCCCCATTTAG hIgG2-hCD4* construct with signal sequence and with FLAG tag Nucleotide sequence

SEQ ID NO: 25

ATGTCTGCACTCCTGATCCTCGCTCTCGTTGGAGCTGCAGTTGCTGACTACAAAGACCAT

GACGGAGATTATAAAGATCATGACATCGATTACAAGGATGACGATGACAAGGCGATCGCG

AACGGATGTGTCGAGTGCCCACCTTGCCCAGCACCACCTGTGGCAGGACCTTCAGTCTTC

CTCTTCCCCCCAAAACCCAAGGACACCCTCATGATCTCCCGGACCCCTGAGGTCACATGC

GTGGTGGTGGACGTGAGCCACGAAGACCCCGAGGTCCAGTTTAATTGGTATGTCGACGGC

GTGGAGGTGCATAATGCCAAGACAAAGCCACGGGAGGAGCAGTTCAACAGCACATTCAGG

GTGGTCAGCGTCCTCACCGTTGTGCACCAGGACTGGCTGAACGGCAAGGAGTACAAGTGC

AAGGTGTCCAACAAAGGCCTCCCAGCCCCCATCGAGAAAACCATCTCCAAAACCAAAGGG

CAGCCCAGAGAACCACAGGTGTACACCCTGCCCCCATCCCGGGAGGAGATGACCAAGAAC

CAGGTCAGCCTGACCTGCCTGGTGAAGGGATTTTATCCTTCCGACATCGCCGTGGAGTGG

GAGAGCAATGGGCAGCCTGAGAACAACTACAAGACCACACCTCCCATGCTGGACTCCGAC

GGCTCCTTCTTCCTGTATTCCAAACTCACCGTGGACAAGAGCAGGTGGCAGCAGGGGAAC

GTCTTCTCATGCTCCGTGATGCATGAGGCTCTGCACAACCACTACACACAGAAGAGCCTC

TCCCTGTCCCCTGGAAAGGGGCGCGCCATGGCCCTGATTGTGCTGGGGGGCGTCGCCGGC

CTCCTGCTTTTCATTGGGCTCGGCATCTTCTTCTGTGTCCGCTGCCGGCACCGACGCCGC

CAAGCAGAGCGGATGTCTCAGATCAAGAGACTCCTCAGTGAGAAGAAGACCGCACAGTGC

CCTCACCGGTTTCAGAAGACATGTAGCCCCATTTAG hIgG2-hCD4-GFP construct with signal sequence and with FLAG tag Amino Acid sequence

SEQ ID NO: 26

-continued

MSALLILALVGAAVADYKDHDGDYKDHDIDYKDDDDKAIANGCVECPPCPAPPVAGPSVF

LFPPKPKDTLMISRTPEVTCVVVDVSHEDPEVQFNWYVDGVEVHNAKTKPREEQFNSTFR

VVSVLTVVHQDWLNGKEYKCKVSNKGLPAPIEKTISKTKGQPREPQVYTLPPSREEMTKN

QVSLTCLVKGFYPSDIAVEWESNGQPENNYKTTPPMLDSDGSFFLYSKLTVDKSRWQQGN

VFSCSVMHEALHNHYTQKSLSLSPGKGRAMALIVLGGVAGLLLFIGLGIFFCVRCRHRRR

QAERMSQIKRLLSEKKTAQCPHRFQKTCSPIMVSKGEELFTGVVPILVELDGDVNGHKFS

VSGEGEGDATYGKLTLKFICTTGKLPVPWPTLVTTLTYGVQCFARYPDHMKQHDFFKSAM

PEGYVQERTIFFKDDGNYKTRAEVKFEGDTLVNRIELKGIDFKEDGNILGHKLEYNYNSH

KVYITADKQKNGIKVNFKTRHNIEDGSVQLADHYQQNTPIGDGPVLLPDNHYLSTQSALS

KDPNEKRDHMVLLEFVTAAGITLGMDELYK hIgG2-hCD4-GFP construct with signal sequence and with
FLAG tag Nucleotide sequence
SEQ ID NO: 27

ATGTCTGCACTCCTGATCCTCGCTCTCGTTGGAGCTGCAGTTGCTGACTACAAAGACCAT

GACGGAGATTATAAAGATCATGACATCGATTACAAGGATGACGATGACAAGGCGATCGCG

AACGGATGTGTCGAGTGCCCACCTTGCCCAGCACCACCTGTGGCAGGACCTTCAGTCTTC

CTCTTCCCCCCAAAACCCAAGGACACCCTCATGATCTCCCGGACCCCTGAGGTCACATGC

GTGGTGGTGGACGTGAGCCACGAAGACCCCGAGGTCCAGTTTAATTGGTATGTCGACGGC

GTGGAGGTGCATAATGCCAAGACAAAGCCACGGGAGGAGCAGTTCAACAGCACATTCAGG

GTGGTCAGCGTCCTCACCGTTGTGCACCAGGACTGGCTGAACGGCAAGGAGTACAAGTGC

AAGGTGTCCAACAAAGGCCTCCCAGCCCCCATCGAGAAAACCATCTCCAAAACCAAAGGG

CAGCCCAGAGAACCACAGGTGTACACCCTGCCCCCATCCCGGGAGGAGATGACCAAGAAC

CAGGTCAGCCTGACCTGCCTGGTGAAGGGATTTTATCCTTCCGACATCGCCGTGGAGTGG

GAGAGCAATGGGCAGCCTGAGAACAACTACAAGACCACACCTCCCATGCTGGACTCCGAC

GGCTCCTTCTTCCTGTATTCCAAACTCACCGTGGACAAGAGCAGGTGGCAGCAGGGGAAC

GTCTTCTCATGCTCCGTGATGCATGAGGCTCTGCACAACCACTACACACAGAAGAGCCTC

TCCCTGTCCCCTGGAAAGGGGCGCGCCATGGCCCTGATTGTGCTGGGGGGCGTCGCCGGC

CTCCTGCTTTTCATTGGGCTCGGCATCTTCTTCTGTGTCCGCTGCCGGCACCGACGCCGC

CAAGCAGAGCGGATGTCTCAGATCAAGAGACTCCTCAGTGAGAAGAAGACCGCACAGTGC

CCTCACCGGTTTCAGAAGACATGTAGCCCCATTATGGTGAGCAAGGGCGAGGAGCTGTTC

ACCGGGGTGGTGCCCATCCTGGTCGAGCTGGACGGCGACGTAAACGGCCACAAGTTCAGC

GTGTCCGGCGAGGGCGAGGGCGATGCCACCTACGGCAAGCTGACCCTGAAGTTCATCTGC

ACCACCGGCAAGCTGCCCGTGCCCTGGCCCACCCTCGTGACCACCTTGACCTACGGCGTG

CAGTGCTTCGCCCGCTACCCCGACCACATGAAGCAGCACGACTTCTTCAAGTCCGCCATG

CCCGAAGGCTACGTCCAGGAGCGCACCATCTTCTTCAAGGACGACGGCAACTACAAGACC

CGCGCCGAGGTGAAGTTCGAGGGCGACACCCTGGTGAACCGCATCGAGCTGAAGGGCATC

GACTTCAAGGAGGACGGCAACATCCTGGGGCACAAGCTGGAGTACAACTACAACAGCCAC

AAGGTCTATATCACCGCCGACAAGCAGAAGAACGGCATCAAGGTGAACTTCAAGACCCGC

CACAACATCGAGGACGGCAGCGTGCAGCTCGCCGACCACTACCAGCAGAACACCCCCATC

GGCGACGGCCCCGTGCTGCTGCCCGACAACCACTACCTGAGCACCCAGTCCGCCCTGAGC

AAAGACCCCAACGAGAAGCGCGATCACATGGTCCTGCTGGAGTTCGTGACCGCCGCCGGG

ATCACTCTCGGCATGGACGAGCTGTACAAGTAGTAG

-continued hIgG2-hCD4-GFP construct without signal sequence and
without FLAG tag Amino Acid sequence
SEQ ID NO: 28

CVECPPCPAPPVAGPSVFLFPPKPKDTLMISRTPEVTCVVVDVSHEDPEVQFNWYVDGVE

VHNAKTKPREEQFNSTFRVVSVLTVVHQDWLNGKEYKCKVSNKGLPAPIEKTISKTKGQP

REPQVYTLPPSREEMTKNQVSLTCLVKGFYPSDIAVEWESNGQPENNYKTTPPMLDSDGS

FFLYSKLTVDKSRWQQGNVFSCSVMHEALHNHYTQKSLSLSPGKGRAMALIVLGGVAGLL

LFIGLGIFFCVRCRHRRRQAERMSQIKRLLSEKKTAQCPHRFQKTCSPIMVSKGEELFTG

VVPILVELDGDVNGHKFSVSGEGEGDATYGKLTLKFICTTGKLPVPWPTLVTTLTYGVQC

FARYPDHMKQHDFFKSAMPEGYVQERTIFFKDDGNYKTRAEVKFEGDTLVNRIELKGIDF

KEDGNILGHKLEYNYNSHKVYITADKQKNGIKVNFKTRHNIEDGSVQLADHYQQNTPIGD

GPVLLPDNHYLSTQSALSKDPNEKRDHMVLLEFVTAAGITLGMDELYK hIgG2-hCD4-GFP construct without signal sequence and
without FLAG tag Nucleotide sequence
SEQ ID NO: 29

TGTGTCGAGTGCCCACCTTGCCCAGCACCACCTGTGGCAGGACCTTCAGTCTTCCTCTTC

CCCCCAAAACCCAAGGACACCCTCATGATCTCCCGGACCCCTGAGGTCACATGCGTGGTG

GTGGACGTGAGCCACGAAGACCCCGAGGTCCAGTTTAATTGGTATGTCGACGGCGTGGAG

GTGCATAATGCCAAGACAAAGCCACGGGAGGAGCAGTTCAACAGCACATTCAGGGTGGTC

AGCGTCCTCACCGTTGTGCACCAGGACTGGCTGAACGGCAAGGAGTACAAGTGCAAGGTG

TCCAACAAAGGCCTCCCAGCCCCCATCGAGAAAACCATCTCCAAAACCAAAGGGCAGCCC

AGAGAACCACAGGTGTACACCCTGCCCCCATCCCGGGAGGAGATGACCAAGAACCAGGTC

AGCCTGACCTGCCTGGTGAAGGGATTTTATCCTTCCGACATCGCCGTGGAGTGGGAGAGC

AATGGGCAGCCTGAGAACAACTACAAGACCACACCTCCCATGCTGGACTCCGACGGCTCC

TTCTTCCTGTATTCCAAACTCACCGTGGACAAGAGCAGGTGGCAGCAGGGGAACGTCTTC

TCATGCTCCGTGATGCATGAGGCTCTGCACAACCACTACACACAGAAGAGCCTCTCCCTG

TCCCCTGGAAAGGGGCGCGCCATGGCCCTGATTGTGCTGGGGGGCGTCGCCGGCCTCCTG

CTTTTCATTGGGCTCGGCATCTTCTTCTGTGTCCGCTGCCGGCACCGACGCCGCCAAGCA

GAGCGGATGTCTCAGATCAAGAGACTCCTCAGTGAGAAGAAGACCGCACAGTGCCCTCAC

CGGTTTCAGAAGACATGTAGCCCCATTATGGTGAGCAAGGGCGAGGAGCTGTTCACCGGG

GTGGTGCCCATCCTGGTCGAGCTGGACGGCGACGTAAACGGCCACAAGTTCAGCGTGTCC

GGCGAGGGCGAGGGCGATGCCACCTACGGCAAGCTGACCCTGAAGTTCATCTGCACCACC

GGCAAGCTGCCCGTGCCCTGGCCCACCCTCGTGACCACCTTGACCTACGGCGTGCAGTGC

TTCGCCCGCTACCCCGACCACATGAAGCAGCACGACTTCTTCAAGTCCGCCATGCCCGAA

GGCTACGTCCAGGAGCGCACCATCTTCTTCAAGGACGACGGCAACTACAAGACCCGCGCC

GAGGTGAAGTTCGAGGGCGACACCCTGGTGAACCGCATCGAGCTGAAGGGCATCGACTTC

AAGGAGGACGGCAACATCCTGGGGCACAAGCTGGAGTACAACTACAACAGCCACAAGGTC

TATATCACCGCCGACAAGCAGAAGAACGGCATCAAGGTGAACTTCAAGACCCGCCACAAC

ATCGAGGACGGCAGCGTGCAGCTCGCCGACCACTACCAGCAGAACACCCCCATCGGCGAC

GGCCCCGTGCTGCTGCCCGACAACCACTACCTGAGCACCCAGTCCGCCCTGAGCAAAGAC

CCCAACGAGAAGCGCGATCACATGGTCCTGCTGGAGTTCGTGACCGCCGCCGGGATCACT

CTCGGCATGGACGAGCTGTACAAGTAGTAG hIgG2-hCD4-GFP construct - predicted mature protein
Amino Acid sequence
SEQ ID NO: 30

-continued

```
DYKDHDGDYKDHDIDYKDDDDKAIANGCVECPPCPAPPVAGPSVFLFPPKPKDTLMISRT

PEVTCVVVDVSHEDPEVQFNWYVDGVEVHNAKTKPREEQFNSTFRVVSVLTVVHQDWLNG

KEYKCKVSNKGLPAPIEKTISKTKGQPREPQVYTLPPSREEMTKNQVSLTCLVKGFYPSD

IAVEWESNGQPENNYKTTPPMLDSDGSFFLYSKLTVDKSRWQQGNVFSCSVMHEALHNHY

TQKSLSLSPGKGRAMALIVLGGVAGLLLFIGLGIFFCVRCRHRRRQAERMSQIKRLLSEK

KTAQCPHRFQKTCSPIMVSKGEELFTGVVPILVELDGDVNGHKFSVSGEGEGDATYGKLT

LKFICTTGKLPVPWPTLVTTLTYGVQCFARYPDHMKQHDFFKSAMPEGYVQERTIFFKDD

GNYKTRAEVKFEGDTLVNRIELKGIDFKEDGNILGHKLEYNYNSHKVYITADKQKNGIKV

NFKTRHNIEDGSVQLADHYQQNTPIGDGPVLLPDNHYLSTQSALSKDPNEKRDHMVLLEF

VTAAGITLGMDELYK
``` mIgG1-hCD4 construct - predicted mature protein
Amino Acid sequence
SEQ ID NO: 31
```
DYKDHDGDYKDHDIDYKDDDDKAIAGCKPCICTVPEVSSVFIFPPKPKDVLTITLTPKVT

CVVVDISKDDPEVQFSWFVDDVEVHTAQTQPREEQFNSTFRSVSELPIMHQDWLNGKEFK

CRVNSAAFPAPIEKTISKTKGRPKAPQVYTIPPPKEQMAKDKVSLTCMITDFFPEDITVE

WQWNGQPAENYKNTQPIMDTDGSYFVYSKLNVQKSNWEAGNTFTCSVLHEGLHNHHTEKS

LSHSPGKGRAMALIVLGGVAGLLLFIGLGIFFCVRCRHRRRQAERMSQIKRLLSEKKTCQ

CPHRFQKTCSPI
``` hIgG2-hCD4 construct - predicted mature protein
Amino Acid sequence
SEQ ID NO: 32
```
DYKDHDGDYKDHDIDYKDDDDKAIANGCVECPPCPAPPVAGPSVFLFPPKPKDTLMISRT

PEVTCVVVDVSHEDPEVQFNWYVDGVEVHNAKTKPREEQFNSTFRVVSVLTVVHQDWLNG

KEYKCKVSNKGLPAPIEKTISKTKGQPREPQVYTLPPSREEMTKNQVSLTCLVKGFYPSD

IAVEWESNGQPENNYKTTPPMLDSDGSFFLYSKLTVDKSRWQQGNVFSCSVMHEALHNHY

TQKSLSLSPGKGRAMALIVLGGVAGLLLFIGLGIFFCVRCRHRRRQAERMSQIKRLLSEK

KTAQCPHRFQKTCSPI
```

MAbLib construct (sc21M18 sequence) predicted signal
sequence underlined Nucleotide sequence
SEQ ID NO: 33
```
ATGGTACTCCAAACCCAAGTATTCATCTCGCTGCTGTTGTGGATTAGCGGAGCGTATGGA

GATATCGTCATGACACAGTCACCGGACTCGCTTGCAGTATCGCTCGGCGAGAGGGCCACC

ATTTCGTGTCGCGCTTCAGAGTCAGTCGATAACTACGGGATCTCGTTTATGAAGTGGTTT

CAGCAGAAGCCCGGACAACCACCGAAGTTGCTCATCTACGCGGCTTCAAATCAGGGGTCA

GGGGTCCCTGACAGATTTTCCGGCTCCGGTTCCGGTACAGATTTCACGCTGACCATCTCG

TCGCTGCAGGCCGAGGACGTGGCCGTGTATTACTGCCAGCAGTCAAAAGAGGTCCCCTGG

ACTTTTGGGGGTGGGACGAAAGTGGAGATCAAGCGTACGGTGGCGGCACCTTCAGTGTTT

ATCTTCCCGCCGTCCGACGAACAGCTTAAGTCCGGTACGGCGTCGGTAGTCTGCCTGCTG

AACAATTTCTATCCCAGGGAAGCGAAAGTACAATGGAAGGTCGACAATGCCCTCCAGAGC

GGGAATAGCCAAGAATCGGTCACAGAACAGGATTCGAAGGACTCAACGTATAGCCTTTCG

TCCACACTTACACTCTCGAAAGCTGACTATGAGAAGCATAAGGTCTATGCATGTGAAGTC

ACTCATCAAGGTCTTTCGTCGCCCGTAACCAAGAGCTTCAACCGCGGAGAGTGTGGAGGA

GGTGGTGGATCAGGCGGTGGTGGGTCGGGAGGGGGTGGCAGCGGAGGAGGGGGATCCGGT

GGAGGGGGTAGCGGGGGAGGAGGGAGCCAGGTGCAATTGGTGCAGTCCGGGGCAGAAGTG
```

-continued

```
AAGAAGCCTGGCGCGTCAGTGAAGATCAGCTGCAAAGCCTCGGGGTATTCCTTTACAGCA

TACTACATTCACTGGGTCAAACAGGCGCCAGGACAGGGGTTGGAGTGGATTGGATACATT

TCCTCGTACAACGGGGCCACGAACTACAATCAGAAATTCAAAGGACGGGTGACGTTTACT

ACGGACACCAGCACTTCGACGGCTACATGGAGCTTCGATCACTCCGGTCCGATGACACG

GCTGTATACTACTGTGCCAGAGATTATGATTATGATGTGGGAATGGACTACTGGGGACAG

GGGACATTGGTAACAGTGAGCTCAGCCAGCACAAAGGGCCCTAGCGTCTTCCCTCTGGCC

CCCTGCAGCAGGAGCACCAGCGAGAGCACAGCCGCCCTGGGCTGCCTGGTCAAGGACTAC

TTCCCCGAACCGGTGACGGTGTCGTGGAACTCAGGCGCTCTGACCAGCGGCGTGCACACC

TTCCCAGCTGTCCTACAGTCCTCAGGACTCTACTCCCTCAGCAGCGTGGTGACCGTGCCC

TCCAGCAACTTCGGCACCCAGACCTACACCTGCAACGTAGATCACAAGCCCAGCAACACC

AAGGTGGACAAGACAGTTGAGCGCAAATGTTGTGTCGAGTGCCCACCGTGCCCAGCACCA

CCTGTGGCAGGACCGTCAGTCTTCCTCTTCCCCCCAAAACCCAAGGACACCCTCATGATC

TCCCGGACCCCTGAGGTCACGTGCGTGGTGGTGGACGTGAGCCACGAAGACCCCGAGGTC

CAGTTCAACTGGTACGTGGACGGCGTGGAGGTGCATAATGCCAAGACAAAGCCACGGGAG

GAGCAGTTCAACAGCACGTTCCGTGTGGTCAGCGTCCTCACCGTTGTGCACCAGGACTGG

CTGAACGGCAAGGAGTACAAGTGCAAGGTCTCCAACAAAGGCCTCCCAGCCCCCATCGAG

AAAACCATCTCCAAAACCAAAGGGCAGCCCCGAGAACCACAGGTGTACACCCTGCCCCCA

TCCCGGGAGGAGATGACCAAGAACCAGGTCAGCCTGACCTGCCTGGTCAAAGGCTTCTAC

CCCAGCGACATCGCCGTGGAGTGGGAGAGCAATGGGCAGCCGGAGAACAACTACAAGACC

ACACCTCCCATGCTGGACTCCGACGGCTCCTTCTTCCTCTACAGCAAGCTCACCGTGGAC

AAGAGCAGGTGGCAGCAGGGGAACGTCTTCTCATGCTCCGTGATGCATGAGGCTCTGCAC

AACCACTACACGCAGAAGAGCCTCTCCCTGTCTCCGGGTAAA
```

MAbLib construct (sc21M18 sequence) predicted signal
sequence underlined Amino Acid sequence
SEQ ID NO: 34

<u>MVLQTQVFISLLLWISGAYG</u>DIVMTQSPDSLAVSLGERATISCRASESVDNYGISFMKWF

QQKPGQPPKLLIYAASNQGSGVPDRFSGSGSGTDFTLTISSLQAEDVAVYYCQQSKEVPW

TFGGGTKVEIKRTVAAPSVFIFPPSDEQLKSGTASVVCLLNNFYPREAKVQWKVDNALQS

GNSQESVTEQDSKDSTYSLSSTLTLSKADYEKHKVYACEVTHQGLSSPVTKSFNRGECGG

GGGSGGGGSGGGGSGGGGSGGGGSGGGGSQVQLVQSGAEVKKPGASVKISCKASGYSFTA

YYIHWVKQAPGQGLEWIGYISSYNGATNYNQKFKGRVTFTTDTSTSTAYMELRSLRSDDT

AVYYCARDYDYDVGMDYWGQGTLVTVSSASTKGPSVFPLAPCSRSTSESTAALGCLVKDY

FPEPVTVSWNSGALTSGVHTFPAVLQSSGLYSLSSVVTVPSSNFGTQTYTCNVDHKPSNT

KVDKTVERKCCVECPPCPAPPVAGPSVFLFPPKPKDTLMISRTPEVTCVVVDVSHEDPEV

QFNWYVDGVEVHNAKTKPREEQFNSTFRVVSVLTVVHQDWLNGKEYKCKVSNKGLPAPIE

KTISKTKGQPREPQVYTLPPSREEMTKNQVSLTCLVKGFYPSDIAVEWESNGQPENNYKT

TPPMLDSDGSFFLYSKLTVDKSRWQQGNVFSCSVMHEALHNHYTQKSLSLSPGK

What is claimed is:

1. A method of producing a host cell, comprising
    (a) transfecting a cell with a polynucleotide that encodes a polypeptide, wherein the polypeptide comprises (i) an extracellular portion comprising an immunoglobulin heavy chain constant region comprising CH2 and CH3 domains; and (ii) a non-immunoglobulin transmembrane portion, wherein the polypeptide comprises a sequence at least 80% identical to SEQ ID NO:10, SEQ ID NO:12, SEQ ID NO:22, SEQ ID NO:23, SEQ ID NO:26, SEQ ID NO:28, SEQ ID NO:30, SEQ ID NO:31, or SEQ ID NO:32; and
    (b) incubating the cell to allow expression of the polypeptide.

2. The method of claim 1, wherein the polypeptide comprises a sequence at least 80% identical to SEQ ID NO:12.

3. The method of claim 1, wherein the polypeptide comprises SEQ ID NO:10, SEQ ID NO: 12, SEQ ID NO:22, SEQ ID NO:23, SEQ ID NO:26, SEQ ID NO:28, SEQ ID NO:30, SEQ ID NO:31, or SEQ ID NO:32.

4. The method of claim 1, wherein the polypeptide comprises SEQ ID NO:12.

5. The method of claim 1, wherein the cell is transiently transfected.

6. The method of claim 1, wherein the cell is stably transfected.

7. The method of claim 1, wherein the polynucleotide encoding the polypeptide is integrated into the genome of the cell.

8. The method of claim 1, wherein the polynucleotide encoding the polypeptide is stably expressed.

9. The method of claim 1, wherein the polypeptide is membrane-bound and expressed on the surface of the cell.

10. The method of claim 1, further comprising (c) detecting expression of the polypeptide on the surface of the cell using a detection molecule.

11. The method of claim 10, wherein the detection molecule is labeled.

12. The method of claim 10, further comprising (d) isolating a cell that expresses the polypeptide on the surface of the cell.

13. The method of claim 12, wherein isolating a cell expressing the polypeptide comprises using flow cytometry or fluorescence-activated cell sorting (FACS).

14. The method of claim 1, wherein the cell is a mammalian cell.

15. The method of claim 1, wherein the cell is a fusion partner cell line.

16. The method of claim 1, wherein the cell is selected from the group consisting of Sp2/0, Sp2/0-Ag14, YB2/0, K6H6/B5, NS-1, FO, Y3/Ag 1.2.3, P3X63Ag8.653, HeLa, BHK, CV-1, 3T3, L-cell, TC7, HEK-293, 293T, CHO, and variants thereof.

17. A host cell produced by the method of claim 1.

* * * * *

SEQUENCE LISTING

<160> NUMBER OF SEQ ID NOS: 34

<210> SEQ ID NO 1
<211> LENGTH: 666

<212> TYPE: DNA
<213> ORGANISM: Artificial Sequence
<220> FEATURE:
<223> OTHER INFORMATION: Mouse IgG1 constant region

<400> SEQUENCE: 1

```
ggttgtaagc cttgcatatg tacagtccca gaagtatcat ctgtcttcat cttccccca      60
aagcccaagg atgtgctcac cattactctg actcctaagg tcacgtgtgt tgtggtagac    120
atcagcaagg atgatcccga ggtccagttc agctggtttg tagatgatgt ggaggtgcac    180
acagctcaga cgcaacccg ggaggagcag ttcaacagca ctttccgctc agtcagtgaa     240
cttcccatca tgcaccagga ctggctcaat ggcaaggagt tcaaatgcag ggtcaacagt    300
gcagctttcc ctgcccccat cgagaaaacc atctccaaaa ccaaaggcag accgaaggct    360
ccacaggtgt acaccattcc acctcccaag gagcagatgg ccaaggataa agtcagtctg    420
acctgcatga taacagactt cttccctgaa gacattactg tggagtggca gtggaatggg    480
cagccagcgg agaactacaa gaacactcag cccatcatgg acacagatgg ctcttacttc    540
gtctacagca agctcaatgt gcagaagagc aactgggagg caggaaatac tttcacctgc    600
tctgtgttac atgagggcct gcacaaccac catactgaga agagcctctc ccactctcct    660
ggtaaa                                                                666
```

<210> SEQ ID NO 2
<211> LENGTH: 222
<212> TYPE: PRT
<213> ORGANISM: Artificial Sequence
<220> FEATURE:
<223> OTHER INFORMATION: Mouse IgG1 constant region

<400> SEQUENCE: 2

```
Gly Cys Lys Pro Cys Ile Cys Thr Val Pro Glu Val Ser Ser Val Phe
  1               5                  10                  15

Ile Phe Pro Pro Lys Pro Lys Asp Val Leu Thr Ile Thr Leu Thr Pro
             20                  25                  30

Lys Val Thr Cys Val Val Val Asp Ile Ser Lys Asp Asp Pro Glu Val
         35                  40                  45

Gln Phe Ser Trp Phe Val Asp Asp Val Glu Val His Thr Ala Gln Thr
     50                  55                  60

Gln Pro Arg Glu Glu Gln Phe Asn Ser Thr Phe Arg Ser Val Ser Glu
 65                  70                  75                  80

Leu Pro Ile Met His Gln Asp Trp Leu Asn Gly Lys Glu Phe Lys Cys
                 85                  90                  95

Arg Val Asn Ser Ala Ala Phe Pro Ala Pro Ile Glu Lys Thr Ile Ser
            100                 105                 110

Lys Thr Lys Gly Arg Pro Lys Ala Pro Gln Val Tyr Thr Ile Pro Pro
        115                 120                 125

Pro Lys Glu Gln Met Ala Lys Asp Lys Val Ser Leu Thr Cys Met Ile
    130                 135                 140

Thr Asp Phe Phe Pro Glu Asp Ile Thr Val Glu Trp Gln Trp Asn Gly
145                 150                 155                 160

Gln Pro Ala Glu Asn Tyr Lys Asn Thr Gln Pro Ile Met Asp Thr Asp
                165                 170                 175

Gly Ser Tyr Phe Val Tyr Ser Lys Leu Asn Val Gln Lys Ser Asn Trp
            180                 185                 190

Glu Ala Gly Asn Thr Phe Thr Cys Ser Val Leu His Glu Gly Leu His
        195                 200                 205
```

Asn His His Thr Glu Lys Ser Leu Ser His Ser Pro Gly Lys
    210                 215                 220

<210> SEQ ID NO 3
<211> LENGTH: 681
<212> TYPE: DNA
<213> ORGANISM: Artificial Sequence
<220> FEATURE:
<223> OTHER INFORMATION: Mouse IgG2a constant region

<400> SEQUENCE: 3

```
atcaagccct gtcctccatg caaatgccca gcacctaacc tcttgggtgg accatccgtc      60
ttcatcttcc ctccaaagat caaggatgta ctcatgatct ccctgagccc catagtcaca     120
tgtgtggtgg tggatgtgag cgaggatgac ccagatgtcc agatcagctg gtttgtgaac     180
aacgtggaag tacacacagc tcagacacaa acccatagag aggattacaa cagtactctc     240
cgggtggtca gtgccctccc catccagcac caggactgga tgagtggcaa ggagttcaaa     300
tgcaaggtca acaacaaaga cctgccagcg cccatcgaga aaccatctc aaaacccaaa      360
gggtcagtaa gagctccaca ggtatatgtc ttgcctccac cagaagaaga tgactaag      420
aaacaggtca ctctgacctg catggtcaca gacttcatgc ctgaagacat ttacgtggag     480
tggaccaaca acgggaaaac agagctaaac tacaagaaca ctgaaccagt cctggactct     540
gatggttctt acttcatgta cagcaagctg agagtggaaa agaagaactg ggtggaaaga     600
aatagctact cctgttcagt ggtccacgag ggtctgcaca atcaccacac gactaagagc     660
ttctcccgga ctccgggtaa a                                              681
```

<210> SEQ ID NO 4
<211> LENGTH: 227
<212> TYPE: PRT
<213> ORGANISM: Artificial Sequence
<220> FEATURE:
<223> OTHER INFORMATION: Mouse IgG2a constant region

<400> SEQUENCE: 4

Ile Lys Pro Cys Pro Cys Lys Cys Pro Ala Pro Asn Leu Leu Gly
1               5                   10                  15

Gly Pro Ser Val Phe Ile Phe Pro Pro Lys Ile Lys Asp Val Leu Met
            20                  25                  30

Ile Ser Leu Ser Pro Ile Val Thr Cys Val Val Val Asp Val Ser Glu
        35                  40                  45

Asp Asp Pro Asp Val Gln Ile Ser Trp Phe Val Asn Asn Val Glu Val
50                  55                  60

His Thr Ala Gln Thr Gln Thr His Arg Glu Asp Tyr Asn Ser Thr Leu
65                  70                  75                  80

Arg Val Val Ser Ala Leu Pro Ile Gln His Gln Asp Trp Met Ser Gly
                85                  90                  95

Lys Glu Phe Lys Cys Lys Val Asn Asn Lys Asp Leu Pro Ala Pro Ile
            100                 105                 110

Glu Arg Thr Ile Ser Lys Pro Lys Gly Ser Val Arg Ala Pro Gln Val
        115                 120                 125

Tyr Val Leu Pro Pro Pro Glu Glu Glu Met Thr Lys Lys Gln Val Thr
        130                 135                 140

Leu Thr Cys Met Val Thr Asp Phe Met Pro Glu Asp Ile Tyr Val Glu
145                 150                 155                 160

Trp Thr Asn Asn Gly Lys Thr Glu Leu Asn Tyr Lys Asn Thr Glu Pro

```
                        165                 170                 175
Val Leu Asp Ser Asp Gly Ser Tyr Phe Met Tyr Ser Lys Leu Arg Val
            180                 185                 190

Glu Lys Lys Asn Trp Val Glu Arg Asn Ser Tyr Ser Cys Ser Val Val
            195                 200                 205

His Glu Gly Leu His Asn His Thr Thr Lys Ser Phe Ser Arg Thr
            210                 215                 220

Pro Gly Lys
225
```

<210> SEQ ID NO 5
<211> LENGTH: 675
<212> TYPE: DNA
<213> ORGANISM: Artificial Sequence
<220> FEATURE:
<223> OTHER INFORMATION: Human IgG1 constant region

<400> SEQUENCE: 5

```
actcacacat gcccaccgtg cccagcacct gaactcctgg ggggaccgtc agtcttcctc     60
ttccccccaa aacccaagga caccctcatg atctcccgga cccctgaggt cacatgcgtg    120
gtggtggacg tgagccacga agaccctgag gtcaagttca actggtacgt ggacggcgtg    180
gaggtgcata atgccaagac aaagccgcgg gaggagcagt acaacagcac gtaccgtgtg    240
gtcagcgtcc tcaccgtcct gcaccaggac tggctgaatg gcaaggagta caagtgcaag    300
gtctccaaca aagccctccc agcccccatc gagaaaacca tctccaaagc caaagggcag    360
ccccgagaac cacaggtgta caccctgccc ccatcccggg atgagctgac caagaaccag    420
gtcagcctga cctgcctggt caaaggcttc tatcccagcg acatcgccgt ggagtgggag    480
agcaatgggc agccggagaa caactacaag accacgcctc ccgtgctgga ctccgacggc    540
tccttcttcc tctacagcaa gctcaccgtg gacaagagca ggtggcagca ggggaacgtc    600
ttctcatgct ccgtgatgca tgaggctctg cacaaccact acacgcagaa gagcctctcc    660
ctgtctccgg gtaaa                                                    675
```

<210> SEQ ID NO 6
<211> LENGTH: 225
<212> TYPE: PRT
<213> ORGANISM: Artificial Sequence
<220> FEATURE:
<223> OTHER INFORMATION: Human IgG1 constant region

<400> SEQUENCE: 6

```
Thr His Thr Cys Pro Pro Cys Pro Ala Pro Glu Leu Leu Gly Gly Pro
1               5                   10                  15

Ser Val Phe Leu Phe Pro Pro Lys Pro Lys Asp Thr Leu Met Ile Ser
            20                  25                  30

Arg Thr Pro Glu Val Thr Cys Val Val Val Asp Val Ser His Glu Asp
        35                  40                  45

Pro Glu Val Lys Phe Asn Trp Tyr Val Asp Gly Val Glu Val His Asn
    50                  55                  60

Ala Lys Thr Lys Pro Arg Glu Glu Gln Tyr Asn Ser Thr Tyr Arg Val
65                  70                  75                  80

Val Ser Val Leu Thr Val Leu His Gln Asp Trp Leu Asn Gly Lys Glu
            85                  90                  95

Tyr Lys Cys Lys Val Ser Asn Lys Ala Leu Pro Ala Pro Ile Glu Lys
            100                 105                 110
```

```
Thr Ile Ser Lys Ala Lys Gly Gln Pro Arg Glu Pro Gln Val Tyr Thr
            115                 120                 125

Leu Pro Pro Ser Arg Asp Glu Leu Thr Lys Asn Gln Val Ser Leu Thr
        130                 135                 140

Cys Leu Val Lys Gly Phe Tyr Pro Ser Asp Ile Ala Val Glu Trp Glu
145                 150                 155                 160

Ser Asn Gly Gln Pro Glu Asn Asn Tyr Lys Thr Thr Pro Pro Val Leu
                165                 170                 175

Asp Ser Asp Gly Ser Phe Phe Leu Tyr Ser Lys Leu Thr Val Asp Lys
            180                 185                 190

Ser Arg Trp Gln Gln Gly Asn Val Phe Ser Cys Ser Val Met His Glu
        195                 200                 205

Ala Leu His Asn His Tyr Thr Gln Lys Ser Leu Ser Leu Ser Pro Gly
    210                 215                 220

Lys
225

<210> SEQ ID NO 7
<211> LENGTH: 669
<212> TYPE: DNA
<213> ORGANISM: Artificial Sequence
<220> FEATURE:
<223> OTHER INFORMATION: Human IgG2 constant region

<400> SEQUENCE: 7
tgtgtcgagt gcccaccttg cccagcacca cctgtggcag gaccttcagt cttcctcttc     60
cccccaaaac ccaaggacac cctcatgatc tcccggaccc ctgaggtcac atgcgtggtg    120
gtggacgtga gccacgaaga ccccgaggtc cagtttaatt ggtatgtcga cggcgtggag    180
gtgcataatg ccaagacaaa gccacgggag gagcagttca acagcacatt cagggtggtc    240
agcgtcctca ccgttgtgca ccaggactgg ctgaacggca aggagtacaa gtgcaaggtg    300
tccaacaaag gcctcccagc ccccatcgag aaaaccatct ccaaaaccaa agggcagccc    360
agagaaccac aggtgtacac cctgccccca tcccgggagg agatgaccaa gaaccaggtc    420
agcctgacct gcctggtgaa gggattttat ccttccgaca tcgccgtgga gtgggagagc    480
aatgggcagc ctgagaacaa ctacaagacc acacctccca tgctggactc cgacggctcc    540
ttcttcctgt attccaaact caccgtggac aagagcaggt ggcagcaggg gaacgtcttc    600
tcatgctccg tgatgcatga ggctctgcac aaccactaca cacagaagag cctctccctg    660
tccctggga                                                           669

<210> SEQ ID NO 8
<211> LENGTH: 223
<212> TYPE: PRT
<213> ORGANISM: Artificial Sequence
<220> FEATURE:
<223> OTHER INFORMATION: Human IgG2 constant region

<400> SEQUENCE: 8

Cys Val Glu Cys Pro Pro Cys Pro Ala Pro Pro Val Ala Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Val Asp Val Ser His Glu Asp Pro
        35                  40                  45

Glu Val Gln Phe Asn Trp Tyr Val Asp Gly Val Glu Val His Asn Ala
    50                  55                  60
```

```
Lys Thr Lys Pro Arg Glu Glu Gln Phe Asn Ser Thr Phe Arg Val Val
 65                  70                  75                  80

Ser Val Leu Thr Val Val His Gln Asp Trp Leu Asn Gly Lys Glu Tyr
                 85                  90                  95

Lys Cys Lys Val Ser Asn Lys Gly Leu Pro Ala Pro Ile Glu Lys Thr
            100                 105                 110

Ile Ser Lys Thr Lys Gly Gln Pro Arg Glu Pro Gln Val Tyr Thr Leu
            115                 120                 125

Pro Pro Ser Arg Glu Glu Met Thr Lys Asn Gln Val Ser Leu Thr Cys
130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Met Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
            195                 200                 205

Leu His Asn His Tyr Thr Gln Lys Ser Leu Ser Leu Ser Pro Gly
        210                 215                 220

<210> SEQ ID NO 9
<211> LENGTH: 873
<212> TYPE: DNA
<213> ORGANISM: Artificial Sequence
<220> FEATURE:
<223> OTHER INFORMATION: mIgG1-hCD4 construct without signal sequence
      and without FLAG tag

<400> SEQUENCE: 9
gcgatcgcgg gttgtaagcc ttgcatatgt acagtcccag aagtatcatc tgtcttcatc      60
ttccccccaa agcccaagga tgtgctcacc attactctga ctcctaaggt cacgtgtgtt     120
gtggtagaca tcagcaagga tgatcccgag gtccagttca gctggtttgt agatgatgtg     180
gaggtgcaca cagctcagac gcaaccccgg gaggagcagt tcaacagcac tttccgctca     240
gtcagtgaac ttcccatcat gcaccaggac tggctcaatg gcaaggagtt caaatgcagg     300
gtcaacagtg cagcttttcc tgcccccatc gagaaaacca tctccaaaac caaaggcaga     360
ccgaaggctc acaggtgtat accattcca cctcccaagg agcagatggc aaggataaa      420 gtcagtctga cctgcatgat aacagacttc ttccctgaag acattactgt ggagtggcag     480
tggaatgggc agccagcgga gaactacaag aacactcagc ccatcatgga cacagatggc     540
tcttacttcg tctacagcaa gctcaatgtg cagaagagca ctgggaggc aggaaatact     600 ttcacctgct ctgtgttaca tgagggcctg cacaaccacc atactgagaa gagcctctcc     660
cactctcctg gtaaagggcg cgccatggcc ctgattgtgc tggggggcgt cgccggcctc     720
ctgcttttca ttgggctagg catcttcttc tgtgtcaggt gccggcaccg aaggcgccaa     780
gcagagcgga tgtctcagat caagagactc ctcagtgaga agaagacctg ccagtgccct     840
caccggtttc agaagacatg tagccccatt tag                                 873

<210> SEQ ID NO 10
<211> LENGTH: 290
<212> TYPE: PRT
<213> ORGANISM: Artificial Sequence
<220> FEATURE:
<223> OTHER INFORMATION: mIgG1-hCD4 construct without signal sequence
``` and without FLAG tag

<400> SEQUENCE: 10

| Ala | Ile | Ala | Gly | Cys | Lys | Pro | Cys | Ile | Cys | Thr | Val | Pro | Glu | Val | Ser |
|---|---|---|---|---|---|---|---|---|---|---|---|---|---|---|---|
| 1 | | | | 5 | | | | | 10 | | | | | 15 | |

| Ser | Val | Phe | Ile | Phe | Pro | Pro | Lys | Pro | Lys | Asp | Val | Leu | Thr | Ile | Thr |
|---|---|---|---|---|---|---|---|---|---|---|---|---|---|---|---|
| | | | 20 | | | | | 25 | | | | | 30 | | |

| Leu | Thr | Pro | Lys | Val | Thr | Cys | Val | Val | Val | Asp | Ile | Ser | Lys | Asp | Asp |
|---|---|---|---|---|---|---|---|---|---|---|---|---|---|---|---|
| | | 35 | | | | | 40 | | | | | 45 | | | |

| Pro | Glu | Val | Gln | Phe | Ser | Trp | Phe | Val | Asp | Asp | Val | Glu | Val | His | Thr |
|---|---|---|---|---|---|---|---|---|---|---|---|---|---|---|---|
| | 50 | | | | | 55 | | | | | 60 | | | | |

| Ala | Gln | Thr | Gln | Pro | Arg | Glu | Glu | Gln | Phe | Asn | Ser | Thr | Phe | Arg | Ser |
|---|---|---|---|---|---|---|---|---|---|---|---|---|---|---|---|
| 65 | | | | | 70 | | | | | 75 | | | | | 80 |

| Val | Ser | Glu | Leu | Pro | Ile | Met | His | Gln | Asp | Trp | Leu | Asn | Gly | Lys | Glu |
|---|---|---|---|---|---|---|---|---|---|---|---|---|---|---|---|
| | | | | 85 | | | | | 90 | | | | | 95 | |

| Phe | Lys | Cys | Arg | Val | Asn | Ser | Ala | Ala | Phe | Pro | Ala | Pro | Ile | Glu | Lys |
|---|---|---|---|---|---|---|---|---|---|---|---|---|---|---|---|
| | | | 100 | | | | | 105 | | | | | 110 | | |

| Thr | Ile | Ser | Lys | Thr | Lys | Gly | Arg | Pro | Lys | Ala | Pro | Gln | Val | Tyr | Thr |
|---|---|---|---|---|---|---|---|---|---|---|---|---|---|---|---|
| | | 115 | | | | | 120 | | | | | 125 | | | |

| Ile | Pro | Pro | Pro | Lys | Glu | Gln | Met | Ala | Lys | Asp | Lys | Val | Ser | Leu | Thr |
|---|---|---|---|---|---|---|---|---|---|---|---|---|---|---|---|
| | 130 | | | | | 135 | | | | | 140 | | | | |

| Cys | Met | Ile | Thr | Asp | Phe | Phe | Pro | Glu | Asp | Ile | Thr | Val | Glu | Trp | Gln |
|---|---|---|---|---|---|---|---|---|---|---|---|---|---|---|---|
| 145 | | | | | 150 | | | | | 155 | | | | | 160 |

| Trp | Asn | Gly | Gln | Pro | Ala | Glu | Asn | Tyr | Lys | Asn | Thr | Gln | Pro | Ile | Met |
|---|---|---|---|---|---|---|---|---|---|---|---|---|---|---|---|
| | | | | 165 | | | | | 170 | | | | | 175 | |

| Asp | Thr | Asp | Gly | Ser | Tyr | Phe | Val | Tyr | Ser | Lys | Leu | Asn | Val | Gln | Lys |
|---|---|---|---|---|---|---|---|---|---|---|---|---|---|---|---|
| | | | 180 | | | | | 185 | | | | | 190 | | |

| Ser | Asn | Trp | Glu | Ala | Gly | Asn | Thr | Phe | Thr | Cys | Ser | Val | Leu | His | Glu |
|---|---|---|---|---|---|---|---|---|---|---|---|---|---|---|---|
| | | 195 | | | | | 200 | | | | | 205 | | | |

| Gly | Leu | His | Asn | His | His | Thr | Glu | Lys | Ser | Leu | Ser | His | Ser | Pro | Gly |
|---|---|---|---|---|---|---|---|---|---|---|---|---|---|---|---|
| | 210 | | | | | 215 | | | | | 220 | | | | |

| Lys | Gly | Arg | Ala | Met | Ala | Leu | Ile | Val | Leu | Gly | Gly | Val | Ala | Gly | Leu |
|---|---|---|---|---|---|---|---|---|---|---|---|---|---|---|---|
| 225 | | | | | 230 | | | | | 235 | | | | | 240 |

| Leu | Leu | Phe | Ile | Gly | Leu | Gly | Ile | Phe | Phe | Cys | Val | Arg | Cys | Arg | His |
|---|---|---|---|---|---|---|---|---|---|---|---|---|---|---|---|
| | | | | 245 | | | | | 250 | | | | | 255 | |

| Arg | Arg | Arg | Gln | Ala | Glu | Arg | Met | Ser | Gln | Ile | Lys | Arg | Leu | Leu | Ser |
|---|---|---|---|---|---|---|---|---|---|---|---|---|---|---|---|
| | | | 260 | | | | | 265 | | | | | 270 | | |

| Glu | Lys | Lys | Thr | Cys | Gln | Cys | Pro | His | Arg | Phe | Gln | Lys | Thr | Cys | Ser |
|---|---|---|---|---|---|---|---|---|---|---|---|---|---|---|---|
| | | 275 | | | | | 280 | | | | | 285 | | | |

| Pro | Ile |
|---|---|
| | 290 |

<210> SEQ ID NO 11
<211> LENGTH: 885
<212> TYPE: DNA
<213> ORGANISM: Artificial Sequence
<220> FEATURE:
<223> OTHER INFORMATION: hIgG2-hCD4 construct without signal sequence
      and without FLAG tag

<400> SEQUENCE: 11
gcgatcgcga acggatgtgt cgagtgccca ccttgcccag caccacctgt ggcaggacct    60
tcagtcttcc tcttcccccc aaaacccaag gacaccctca tgatctcccg gacccctgag   120
gtcacatgcg tggtggtgga cgtgagccac gaagaccccg aggtccagtt taattggtat   180
gtcgacggcg tggaggtgca taatgccaag acaaagccac gggaggagca gttcaacagc   240

```
acattcaggg tggtcagcgt cctcaccgtt gtgcaccagg actggctgaa cggcaaggag    300
tacaagtgca aggtgtccaa caaaggcctc ccagccccca tcgagaaaac catctccaaa    360
accaaagggc agcccagaga accacaggtg tacaccctgc ccccatcccg ggaggagatg    420
accaagaacc aggtcagcct gacctgcctg gtgaagggat tttatccttc cgacatcgcc    480
gtggagtggg agagcaatgg gcagcctgag aacaactaca agaccacacc tcccatgctg    540
gactccgacg gctccttctt cctgtattcc aaactcaccg tggacaagag caggtggcag    600
caggggaacg tcttctcatg ctccgtgatg catgaggctc tgcacaacca ctacacacag    660
aagagcctct ccctgtcccc tggaaagggg cgcgccatgg ccctgattgt gctgggggc     720 gtcgccggcc tcctgctttt cattgggctc ggcatcttct tctgtgtccg ctgccggcac    780
cgacgccgcc aagcagagcg gatgtctcag atcaagagac tcctcagtga gaagaagacc    840
gcacagtgcc ctcaccggtt tcagaagaca tgtagcccca tttag                    885
```

<210> SEQ ID NO 12
<211> LENGTH: 294
<212> TYPE: PRT
<213> ORGANISM: Artificial Sequence
<220> FEATURE:
<223> OTHER INFORMATION: hIgG2-hCD4 construct without signal sequence
      and without FLAG tag
<220> FEATURE:
<221> NAME/KEY: MISC_FEATURE
<222> LOCATION: (281)..(281)
<223> OTHER INFORMATION: CD4 Intracellular domain region is modified,
      amino acid change

<400> SEQUENCE: 12

```
Ala Ile Ala Asn Gly Cys Val Glu Cys Pro Pro Cys Pro Ala Pro Pro
1               5                   10                  15

Val Ala Gly Pro Ser Val Phe Leu Phe Pro Pro Lys Pro Lys Asp Thr
                20                  25                  30

Leu Met Ile Ser Arg Thr Pro Glu Val Thr Cys Val Val Val Asp Val
            35                  40                  45

Ser His Glu Asp Pro Glu Val Gln Phe Asn Trp Tyr Val Asp Gly Val
        50                  55                  60

Glu Val His Asn Ala Lys Thr Lys Pro Arg Glu Glu Gln Phe Asn Ser
65                  70                  75                  80

Thr Phe Arg Val Val Ser Val Leu Thr Val Val His Gln Asp Trp Leu
                85                  90                  95

Asn Gly Lys Glu Tyr Lys Cys Lys Val Ser Asn Lys Gly Leu Pro Ala
            100                 105                 110

Pro Ile Glu Lys Thr Ile Ser Lys Thr Lys Gly Gln Pro Arg Glu Pro
        115                 120                 125

Gln Val Tyr Thr Leu Pro Pro Ser Arg Glu Glu Met Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Met Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
```

```
                210                 215                 220
Leu Ser Pro Gly Lys Gly Arg Ala Met Ala Leu Ile Val Leu Gly Gly
225                 230                 235                 240

Val Ala Gly Leu Leu Leu Phe Ile Gly Leu Gly Ile Phe Phe Cys Val
                245                 250                 255

Arg Cys Arg His Arg Arg Arg Gln Ala Glu Arg Met Ser Gln Ile Lys
            260                 265                 270

Arg Leu Leu Ser Glu Lys Lys Thr Ala Gln Cys Pro His Arg Phe Gln
        275                 280                 285

Lys Thr Cys Ser Pro Ile
    290

<210> SEQ ID NO 13
<211> LENGTH: 22
<212> TYPE: PRT
<213> ORGANISM: Artificial Sequence
<220> FEATURE:
<223> OTHER INFORMATION: Human CD4 TM

<400> SEQUENCE: 13

Met Ala Leu Ile Val Leu Gly Gly Val Ala Gly Leu Leu Leu Phe Ile
1               5                   10                  15

Gly Leu Gly Ile Phe Phe
            20

<210> SEQ ID NO 14
<211> LENGTH: 62
<212> TYPE: PRT
<213> ORGANISM: Artificial Sequence
<220> FEATURE:
<223> OTHER INFORMATION: Human CD4 TM-ICD

<400> SEQUENCE: 14

Met Ala Leu Ile Val Leu Gly Gly Val Ala Gly Leu Leu Leu Phe Ile
1               5                   10                  15

Gly Leu Gly Ile Phe Phe Cys Val Arg Cys Arg His Arg Arg Arg Gln
            20                  25                  30

Ala Glu Arg Met Ser Gln Ile Lys Arg Leu Leu Ser Glu Lys Lys Thr
        35                  40                  45

Cys Gln Cys Pro His Arg Phe Gln Lys Thr Cys Ser Pro Ile
    50                  55                  60

<210> SEQ ID NO 15
<211> LENGTH: 62
<212> TYPE: PRT
<213> ORGANISM: Artificial Sequence
<220> FEATURE:
<223> OTHER INFORMATION: Human CD4 TM-ICD
<220> FEATURE:
<221> NAME/KEY: MISC_FEATURE
<222> LOCATION: (49)..(49)
<223> OTHER INFORMATION: CD4 Intracellular domain region is modified,
      amino acid change

<400> SEQUENCE: 15

Met Ala Leu Ile Val Leu Gly Gly Val Ala Gly Leu Leu Leu Phe Ile
1               5                   10                  15

Gly Leu Gly Ile Phe Phe Cys Val Arg Cys Arg His Arg Arg Arg Gln
            20                  25                  30

Ala Glu Arg Met Ser Gln Ile Lys Arg Leu Leu Ser Glu Lys Lys Thr
        35                  40                  45
```

```
Ala Gln Cys Pro His Arg Phe Gln Lys Thr Cys Ser Pro Ile
        50                  55                  60

<210> SEQ ID NO 16
<211> LENGTH: 22
<212> TYPE: PRT
<213> ORGANISM: Artificial Sequence
<220> FEATURE:
<223> OTHER INFORMATION: Mouse CD4 TM

<400> SEQUENCE: 16

Phe Leu Ala Cys Val Leu Gly Gly Ser Phe Gly Phe Leu Gly Phe Leu
1               5                   10                  15

Gly Leu Cys Ile Leu Cys
            20

<210> SEQ ID NO 17
<211> LENGTH: 62
<212> TYPE: PRT
<213> ORGANISM: Artificial Sequence
<220> FEATURE:
<223> OTHER INFORMATION: Mouse CD4 TM-ICD

<400> SEQUENCE: 17

Phe Leu Ala Cys Val Leu Gly Gly Ser Phe Gly Phe Leu Gly Phe Leu
1               5                   10                  15

Gly Leu Cys Ile Leu Cys Cys Val Arg Cys Arg His Gln Gln Arg Gln
            20                  25                  30

Ala Ala Arg Met Ser Gln Ile Lys Arg Leu Leu Ser Glu Lys Lys Thr
        35                  40                  45

Cys Gln Cys Pro His Arg Met Gln Lys Ser His Asn Leu Ile
    50                  55                  60

<210> SEQ ID NO 18
<211> LENGTH: 8
<212> TYPE: PRT
<213> ORGANISM: Artificial Sequence
<220> FEATURE:
<223> OTHER INFORMATION: FLAG tag

<400> SEQUENCE: 18

Asp Tyr Lys Asp Asp Asp Asp Lys
1               5

<210> SEQ ID NO 19
<211> LENGTH: 131
<212> TYPE: PRT
<213> ORGANISM: Artificial Sequence
<220> FEATURE:
<223> OTHER INFORMATION: Human FZD5 Fri-domain sequence (Amino acids
      27-157)

<400> SEQUENCE: 19

Ala Ser Lys Ala Pro Val Cys Gln Glu Ile Thr Val Pro Met Cys Arg
1               5                   10                  15

Gly Ile Gly Tyr Asn Leu Thr His Met Pro Asn Gln Phe Asn His Asp
            20                  25                  30

Thr Gln Asp Glu Ala Gly Leu Glu Val His Gln Phe Trp Pro Leu Val
        35                  40                  45

Glu Ile Gln Cys Ser Pro Asp Leu Arg Phe Phe Leu Cys Ser Met Tyr
    50                  55                  60

Thr Pro Ile Cys Leu Pro Asp Tyr His Lys Pro Leu Pro Pro Cys Arg
65                  70                  75                  80
```

Ser Val Cys Glu Arg Ala Lys Ala Gly Cys Ser Pro Leu Met Arg Gln
            85                  90                  95

Tyr Gly Phe Ala Trp Pro Glu Arg Met Ser Cys Asp Arg Leu Pro Val
            100                 105                 110

Leu Gly Arg Asp Ala Glu Val Leu Cys Met Asp Tyr Asn Arg Ser Glu
            115                 120                 125

Ala Thr Thr
    130

<210> SEQ ID NO 20
<211> LENGTH: 131
<212> TYPE: PRT
<213> ORGANISM: Artificial Sequence
<220> FEATURE:
<223> OTHER INFORMATION: Human FZD8 Fri-domain sequence (Amino acids
      28-158)

<400> SEQUENCE: 20

Ala Ser Ala Lys Glu Leu Ala Cys Gln Glu Ile Thr Val Pro Leu Cys
1               5                   10                  15

Lys Gly Ile Gly Tyr Asn Tyr Thr Tyr Met Pro Asn Gln Phe Asn His
            20                  25                  30

Asp Thr Gln Asp Glu Ala Gly Leu Glu Val His Gln Phe Trp Pro Leu
            35                  40                  45

Val Glu Ile Gln Cys Ser Pro Asp Leu Lys Phe Phe Leu Cys Ser Met
        50                  55                  60

Tyr Thr Pro Ile Cys Leu Glu Asp Tyr Lys Lys Pro Leu Pro Pro Cys
65              70                  75                  80

Arg Ser Val Cys Glu Arg Ala Lys Ala Gly Cys Ala Pro Leu Met Arg
            85                  90                  95

Gln Tyr Gly Phe Ala Trp Pro Asp Arg Met Arg Cys Asp Arg Leu Pro
            100                 105                 110

Glu Gln Gly Asn Pro Asp Thr Leu Cys Met Asp Tyr Asn Arg Thr Asp
            115                 120                 125

Leu Thr Thr
    130

<210> SEQ ID NO 21
<211> LENGTH: 399
<212> TYPE: PRT
<213> ORGANISM: Artificial Sequence
<220> FEATURE:
<223> OTHER INFORMATION: Human DDR2 Amino acids 1-399

<400> SEQUENCE: 21

Met Ile Leu Ile Pro Arg Met Leu Leu Val Leu Phe Leu Leu Leu Pro
1               5                   10                  15

Ile Leu Ser Ser Ala Lys Ala Gln Val Asn Pro Ala Ile Cys Arg Tyr
            20                  25                  30

Pro Leu Gly Met Ser Gly Gly Gln Ile Pro Asp Glu Asp Ile Thr Ala
            35                  40                  45

Ser Ser Gln Trp Ser Glu Ser Thr Ala Ala Lys Tyr Gly Arg Leu Asp
        50                  55                  60

Ser Glu Glu Gly Asp Gly Ala Trp Cys Pro Glu Ile Pro Val Glu Pro
65              70                  75                  80

Asp Asp Leu Lys Glu Phe Leu Gln Ile Asp Leu His Thr Leu His Phe
            85                  90                  95

```
Ile Thr Leu Val Gly Thr Gln Gly Arg His Ala Gly His Gly Ile
            100                 105                 110

Glu Phe Ala Pro Met Tyr Lys Ile Asn Tyr Ser Arg Asp Gly Thr Arg
            115                 120                 125

Trp Ile Ser Trp Arg Asn Arg His Gly Lys Gln Val Leu Asp Gly Asn
        130                 135                 140

Ser Asn Pro Tyr Asp Ile Phe Leu Lys Asp Leu Glu Pro Pro Ile Val
145                 150                 155                 160

Ala Arg Phe Val Arg Phe Ile Pro Val Thr Asp His Ser Met Asn Val
                165                 170                 175

Cys Met Arg Val Glu Leu Tyr Gly Cys Val Trp Leu Asp Gly Leu Val
                180                 185                 190

Ser Tyr Asn Ala Pro Ala Gly Gln Gln Phe Val Leu Pro Gly Gly Ser
            195                 200                 205

Ile Ile Tyr Leu Asn Asp Ser Val Tyr Asp Gly Ala Val Gly Tyr Ser
        210                 215                 220

Met Thr Glu Gly Leu Gly Gln Leu Thr Asp Gly Val Ser Gly Leu Asp
225                 230                 235                 240

Asp Phe Thr Gln Thr His Glu Tyr His Val Trp Pro Gly Tyr Asp Tyr
                245                 250                 255

Val Gly Trp Arg Asn Glu Ser Ala Thr Asn Gly Tyr Ile Glu Ile Met
                260                 265                 270

Phe Glu Phe Asp Arg Ile Arg Asn Phe Thr Thr Met Lys Val His Cys
            275                 280                 285

Asn Asn Met Phe Ala Lys Gly Val Lys Ile Phe Lys Glu Val Gln Cys
        290                 295                 300

Tyr Phe Arg Ser Glu Ala Ser Glu Trp Glu Pro Asn Ala Ile Ser Phe
305                 310                 315                 320

Pro Leu Val Leu Asp Asp Val Asn Pro Ser Ala Arg Phe Val Thr Val
                325                 330                 335

Pro Leu His His Arg Met Ala Ser Ala Ile Lys Cys Gln Tyr His Phe
                340                 345                 350

Ala Asp Thr Trp Met Met Phe Ser Glu Ile Thr Phe Gln Ser Asp Ala
            355                 360                 365

Ala Met Tyr Asn Asn Ser Glu Ala Leu Pro Thr Ser Pro Met Ala Pro
        370                 375                 380

Thr Thr Tyr Asp Pro Met Leu Lys Val Asp Asp Ser Asn Thr Arg
385                 390                 395

<210> SEQ ID NO 22
<211> LENGTH: 327
<212> TYPE: PRT
<213> ORGANISM: Artificial Sequence
<220> FEATURE:
<223> OTHER INFORMATION: mIgG1-hCD4 construct with signal sequence and
      with FLAG tag

<400> SEQUENCE: 22

Met Ser Ala Leu Leu Ile Leu Ala Leu Val Gly Ala Ala Val Ala Asp
1               5                   10                  15

Tyr Lys Asp His Asp Gly Asp Tyr Lys Asp His Asp Ile Asp Tyr Lys
            20                  25                  30

Asp Asp Asp Asp Lys Ala Ile Ala Gly Cys Lys Pro Cys Ile Cys Thr
        35                  40                  45

Val Pro Glu Val Ser Ser Val Phe Ile Phe Pro Pro Lys Pro Lys Asp
    50                  55                  60
```

```
Val Leu Thr Ile Thr Leu Thr Pro Lys Val Cys Val Val Asp
 65              70                  75                  80

Ile Ser Lys Asp Asp Pro Glu Val Gln Phe Ser Trp Phe Val Asp Asp
                 85                  90                  95

Val Glu Val His Thr Ala Gln Thr Gln Pro Arg Glu Glu Gln Phe Asn
                100                 105                 110

Ser Thr Phe Arg Ser Val Ser Glu Leu Pro Ile Met His Gln Asp Trp
            115                 120                 125

Leu Asn Gly Lys Glu Phe Lys Cys Arg Val Asn Ser Ala Ala Phe Pro
        130                 135                 140

Ala Pro Ile Glu Lys Thr Ile Ser Lys Thr Lys Gly Arg Pro Lys Ala
145                 150                 155                 160

Pro Gln Val Tyr Thr Ile Pro Pro Lys Glu Gln Met Ala Lys Asp
                165                 170                 175

Lys Val Ser Leu Thr Cys Met Ile Thr Asp Phe Phe Pro Glu Asp Ile
            180                 185                 190

Thr Val Glu Trp Gln Trp Asn Gly Gln Pro Ala Glu Asn Tyr Lys Asn
            195                 200                 205

Thr Gln Pro Ile Met Asp Thr Asp Gly Ser Tyr Phe Val Tyr Ser Lys
        210                 215                 220

Leu Asn Val Gln Lys Ser Asn Trp Glu Ala Gly Asn Thr Phe Thr Cys
225                 230                 235                 240

Ser Val Leu His Glu Gly Leu His Asn His His Thr Glu Lys Ser Leu
                245                 250                 255

Ser His Ser Pro Gly Lys Gly Arg Ala Met Ala Leu Ile Val Leu Gly
            260                 265                 270

Gly Val Ala Gly Leu Leu Leu Phe Ile Gly Leu Gly Ile Phe Phe Cys
        275                 280                 285

Val Arg Cys Arg His Arg Arg Gln Ala Glu Arg Met Ser Gln Ile
290                 295                 300

Lys Arg Leu Leu Ser Glu Lys Lys Thr Cys Gln Cys Pro His Arg Phe
305                 310                 315                 320

Gln Lys Thr Cys Ser Pro Ile
                325

<210> SEQ ID NO 23
<211> LENGTH: 331
<212> TYPE: PRT
<213> ORGANISM: Artificial Sequence
<220> FEATURE:
<223> OTHER INFORMATION: hIgG2-hCD4 construct with signal sequence and
      with FLAG tag
<220> FEATURE:
<221> NAME/KEY: MISC_FEATURE
<222> LOCATION: (318)..(318)
<223> OTHER INFORMATION: CD4 Intracellular domain region is modified,
      amino acid change

<400> SEQUENCE: 23

Met Ser Ala Leu Leu Ile Leu Ala Leu Val Gly Ala Ala Val Ala Asp
1               5                  10                  15

Tyr Lys Asp His Asp Gly Asp Tyr Lys Asp His Asp Ile Asp Tyr Lys
                20                  25                  30

Asp Asp Asp Asp Lys Ala Ile Ala Asn Gly Cys Val Glu Cys Pro Pro
            35                  40                  45

Cys Pro Ala Pro Pro Val Ala Gly Pro Ser Val Phe Leu Phe Pro Pro
        50                  55                  60
```

Lys Pro Lys Asp Thr Leu Met Ile Ser Arg Thr Pro Glu Val Thr Cys
65                  70                  75                  80

Val Val Val Asp Val Ser His Glu Asp Pro Glu Val Gln Phe Asn Trp
            85                  90                  95

Tyr Val Asp Gly Val Glu Val His Asn Ala Lys Thr Lys Pro Arg Glu
        100                 105                 110

Glu Gln Phe Asn Ser Thr Phe Arg Val Val Ser Val Leu Thr Val Val
    115                 120                 125

His Gln Asp Trp Leu Asn Gly Lys Glu Tyr Lys Cys Lys Val Ser Asn
130                 135                 140

Lys Gly Leu Pro Ala Pro Ile Glu Lys Thr Ile Ser Lys Thr Lys Gly
145                 150                 155                 160

Gln Pro Arg Glu Pro Gln Val Tyr Thr Leu Pro Pro Ser Arg Glu Glu
                165                 170                 175

Met Thr Lys Asn Gln Val Ser Leu Thr Cys Leu Val Lys Gly Phe Tyr
            180                 185                 190

Pro Ser Asp Ile Ala Val Glu Trp Glu Ser Asn Gly Gln Pro Glu Asn
        195                 200                 205

Asn Tyr Lys Thr Thr Pro Pro Met Leu Asp Ser Asp Gly Ser Phe Phe
    210                 215                 220

Leu Tyr Ser Lys Leu Thr Val Asp Lys Ser Arg Trp Gln Gln Gly Asn
225                 230                 235                 240

Val Phe Ser Cys Ser Val Met His Glu Ala Leu His Asn His Tyr Thr
                245                 250                 255

Gln Lys Ser Leu Ser Leu Ser Pro Gly Lys Gly Arg Ala Met Ala Leu
            260                 265                 270

Ile Val Leu Gly Gly Val Ala Gly Leu Leu Leu Phe Ile Gly Leu Gly
        275                 280                 285

Ile Phe Phe Cys Val Arg Cys Arg His Arg Arg Arg Gln Ala Glu Arg
    290                 295                 300

Met Ser Gln Ile Lys Arg Leu Leu Ser Glu Lys Lys Thr Ala Gln Cys
305                 310                 315                 320

Pro His Arg Phe Gln Lys Thr Cys Ser Pro Ile
                325                 330

<210> SEQ ID NO 24
<211> LENGTH: 984
<212> TYPE: DNA
<213> ORGANISM: Artificial Sequence
<220> FEATURE:
<223> OTHER INFORMATION: mIgG1-hCD4 construct with signal sequence and
      with FLAG tag

<400> SEQUENCE: 24
atgtctgcac ttctgatcct agctcttgtt ggagctgcag ttgctgacta caaagaccat    60
gacggtgatt ataagatca tgacatcgat tacaaggatg acgatgacaa ggcgatcgcg   120
ggttgtaagc cttgcatatg tacagtccca gaagtatcat ctgtcttcat cttcccccca   180
aagcccaagg atgtgctcac cattactctg actcctaagg tcacgtgtgt tgtggtagac   240
atcagcaagg atgatcccga ggtccagttc agctggtttg tagatgatgt ggaggtgcac   300
acagctcaga cgcaacccg ggaggagcag ttcaacagca ctttccgctc agtcagtgaa   360
cttcccatca tgcaccagga ctggctcaat ggcaaggagt tcaaatgcag ggtcaacagt   420
gcagctttcc ctgcccccat cgagaaaacc atctccaaaa ccaaaggcag accgaaggct   480

```
ccacaggtgt acaccattcc acctcccaag gagcagatgg ccaaggataa agtcagtctg    540
acctgcatga taacagactt cttccctgaa gacattactg tggagtggca gtggaatggg    600
cagccagcgg agaactacaa gaacactcag cccatcatgg acacagatgg ctcttacttc    660
gtctacagca agctcaatgt gcagaagagc aactgggagg caggaaatac tttcacctgc    720
tctgtgttac atgagggcct gcacaaccac atactgaga agagcctctc ccactctcct    780
ggtaaagggc gcgccatggc cctgattgtg ctgggggggcg tcgccggcct cctgcttttc    840
attgggctag gcatcttctt ctgtgtcagg tgccggcacc gaaggcgcca agcagagcgg    900
atgtctcaga tcaagagact cctcagtgag aagaagacct gccagtgccc tcaccggttt    960
cagaagacat gtagcccat ttag                                            984

<210> SEQ ID NO 25
<211> LENGTH: 996
<212> TYPE: DNA
<213> ORGANISM: Artificial Sequence
<220> FEATURE:
<223> OTHER INFORMATION: hIgG2-hCD4 construct with signal sequence and
      with FLAG tag

<400> SEQUENCE: 25
atgtctgcac tcctgatcct cgctctcgtt ggagctgcag ttgctgacta caaagaccat    60
gacggagatt ataaagatca tgacatcgat tacaaggatg acgatgacaa ggcgatcgcg    120
aacggatgtg tcgagtgccc accttgccca gcaccacctg tggcaggacc ttcagtcttc    180
ctcttccccc caaacccaa ggacaccctc atgatctccc ggaccctga ggtcacatgc      240 gtggtggtgg acgtgagcca cgaagacccc gaggtccagt taattggta tgtcgacggc    300 gtggaggtgc ataatgccaa gacaaagcca cgggaggagc agttcaacag cacattcagg    360
gtggtcagcg tcctcaccgt tgtgcaccag gactggctga acggcaagga gtacaagtgc    420
aaggtgtcca caaaggcct cccagccccc atcgagaaaa ccatctccaa aaccaaaggg    480
cagcccagag aaccacaggt gtacaccctg cccccatccc gggaggagat gaccaagaac    540
caggtcagcc tgacctgcct ggtgaaggga ttttatcctt ccgacatcgc cgtggagtgg    600
gagagcaatg ggcagcctga gaacaactac aagaccacac tcccatgct ggactccgac     660 ggctccttct cctgtatc caaactcacc gtggacaaga gcaggtggca gcaggggaac    720
gtcttctcat gctccgtgat gcatgaggct ctgcacaacc actacacaca gaagagcctc    780
tccctgtccc ctggaaaggg gcgcgccatg gccctgattg tgctgggggg gtcgccggc     840 ctcctgcttt tcattgggct cggcatcttc ttctgtgtcc gctgccggca ccgacgcgc    900 caagcagagc ggatgtctca gatcaagaga ctcctcagtg agaagaagac cgcacagtgc    960
cctcaccggt ttcagaagac atgtagcccc atttag                              996

<210> SEQ ID NO 26
<211> LENGTH: 570
<212> TYPE: PRT
<213> ORGANISM: Artificial Sequence
<220> FEATURE:
<223> OTHER INFORMATION: hIgG2-hCD4-GFP construct with signal sequence
      and with FLAG tag

<400> SEQUENCE: 26

Met Ser Ala Leu Leu Ile Leu Ala Leu Val Gly Ala Ala Val Ala Asp
1               5                   10                  15

Tyr Lys Asp His Asp Gly Asp Tyr Lys Asp His Asp Ile Asp Tyr Lys
            20                  25                  30
```

-continued

```
Asp Asp Asp Asp Lys Ala Ile Ala Asn Gly Cys Val Glu Cys Pro Pro
             35                  40                  45
Cys Pro Ala Pro Pro Val Ala Gly Pro Ser Val Phe Leu Phe Pro Pro
     50                  55                  60
Lys Pro Lys Asp Thr Leu Met Ile Ser Arg Thr Pro Glu Val Thr Cys
 65              70                  75                  80
Val Val Val Asp Val Ser His Glu Asp Pro Glu Val Gln Phe Asn Trp
                 85                  90                  95
Tyr Val Asp Gly Val Glu Val His Asn Ala Lys Thr Lys Pro Arg Glu
             100                 105                 110
Glu Gln Phe Asn Ser Thr Phe Arg Val Val Ser Val Leu Thr Val Val
         115                 120                 125
His Gln Asp Trp Leu Asn Gly Lys Glu Tyr Lys Cys Lys Val Ser Asn
     130                 135                 140
Lys Gly Leu Pro Ala Pro Ile Glu Lys Thr Ile Ser Lys Thr Lys Gly
145                 150                 155                 160
Gln Pro Arg Glu Pro Gln Val Tyr Thr Leu Pro Pro Ser Arg Glu Glu
                 165                 170                 175
Met Thr Lys Asn Gln Val Ser Leu Thr Cys Leu Val Lys Gly Phe Tyr
             180                 185                 190
Pro Ser Asp Ile Ala Val Glu Trp Glu Ser Asn Gly Gln Pro Glu Asn
         195                 200                 205
Asn Tyr Lys Thr Thr Pro Pro Met Leu Asp Ser Asp Gly Ser Phe Phe
     210                 215                 220
Leu Tyr Ser Lys Leu Thr Val Asp Lys Ser Arg Trp Gln Gln Gly Asn
225                 230                 235                 240
Val Phe Ser Cys Ser Val Met His Glu Ala Leu His Asn His Tyr Thr
                 245                 250                 255
Gln Lys Ser Leu Ser Leu Ser Pro Gly Lys Gly Arg Ala Met Ala Leu
             260                 265                 270
Ile Val Leu Gly Gly Val Ala Gly Leu Leu Leu Phe Ile Gly Leu Gly
         275                 280                 285
Ile Phe Phe Cys Val Arg Cys Arg His Arg Arg Gln Ala Glu Arg
     290                 295                 300
Met Ser Gln Ile Lys Arg Leu Leu Ser Glu Lys Lys Thr Ala Gln Cys
305                 310                 315                 320
Pro His Arg Phe Gln Lys Thr Cys Ser Pro Ile Met Val Ser Lys Gly
                 325                 330                 335
Glu Glu Leu Phe Thr Gly Val Val Pro Ile Leu Val Glu Leu Asp Gly
             340                 345                 350
Asp Val Asn Gly His Lys Phe Ser Val Ser Gly Glu Gly Glu Gly Asp
         355                 360                 365
Ala Thr Tyr Gly Lys Leu Thr Leu Lys Phe Ile Cys Thr Thr Gly Lys
     370                 375                 380
Leu Pro Val Pro Trp Pro Thr Leu Val Thr Thr Leu Thr Tyr Gly Val
385                 390                 395                 400
Gln Cys Phe Ala Arg Tyr Pro Asp His Met Lys Gln His Asp Phe Phe
                 405                 410                 415
Lys Ser Ala Met Pro Glu Gly Tyr Val Gln Glu Arg Thr Ile Phe Phe
             420                 425                 430
Lys Asp Asp Gly Asn Tyr Lys Thr Arg Ala Glu Val Lys Phe Glu Gly
         435                 440                 445
```

```
Asp Thr Leu Val Asn Arg Ile Glu Leu Lys Gly Ile Asp Phe Lys Glu
            450                 455                 460

Asp Gly Asn Ile Leu Gly His Lys Leu Glu Tyr Asn Tyr Asn Ser His
465                 470                 475                 480

Lys Val Tyr Ile Thr Ala Asp Lys Gln Lys Asn Gly Ile Lys Val Asn
                485                 490                 495

Phe Lys Thr Arg His Asn Ile Glu Asp Gly Ser Val Gln Leu Ala Asp
                500                 505                 510

His Tyr Gln Gln Asn Thr Pro Ile Gly Asp Gly Pro Val Leu Leu Pro
            515                 520                 525

Asp Asn His Tyr Leu Ser Thr Gln Ser Ala Leu Ser Lys Asp Pro Asn
530                 535                 540

Glu Lys Arg Asp His Met Val Leu Leu Glu Phe Val Thr Ala Ala Gly
545                 550                 555                 560

Ile Thr Leu Gly Met Asp Glu Leu Tyr Lys
                565                 570

<210> SEQ ID NO 27
<211> LENGTH: 1716
<212> TYPE: DNA
<213> ORGANISM: Artificial Sequence
<220> FEATURE:
<223> OTHER INFORMATION: hIgG2-hCD4-GFP construct with signal sequence
      and with FLAG tag

<400> SEQUENCE: 27
atgtctgcac tcctgatcct cgctctcgtt ggagctgcag ttgctgacta caaagaccat      60
gacggagatt ataaagatca tgacatcgat tacaaggatg acgatgacaa ggcgatcgcg     120
aacggatgtg tcgagtgccc accttgccca gcaccacctg tggcaggacc ttcagtcttc     180
ctcttccccc caaaacccaa ggacaccctc atgatctccc ggacccctga ggtcacatgc     240
gtggtggtgg acgtgagcca cgaagacccc gaggtccagt taattggta tgtcgacggc     300 gtggaggtgc ataatgccaa gacaaagcca cgggaggagc agttcaacag cacattcagg     360
gtggtcagcg tcctcaccgt tgtgcaccag gactggctga acggcaagga gtacaagtgc     420
aaggtgtcca acaaaggcct cccagccccc atcgagaaaa ccatctccaa aaccaaaggg     480
cagcccagag aaccacaggt gtacaccctg ccccatccc gggaggagat gaccaagaac     540
caggtcagcc tgacctgcct ggtgaaggga ttttatcctt ccgacatcgc cgtggagtgg     600
gagagcaatg gcagcctga gaacaactac aagaccacac tcccatgct ggactccgac     660 ggctccttct tcctgtattc caaactcacc gtggacaaga gcaggtggca gcagggaaac     720
gtcttctcat gctccgtgat gcatgaggct ctgcacaacc actacacaca gaagagcctc     780
tccctgtccc ctggaaaggg cgcgccatg gccctgattg tgctggggg cgtcgccggc     840 ctcctgcttt tcattgggct cggcatcttc ttctgtgtcc gctgccggca ccgacgccgc     900
caagcagagc ggatgtctca gatcaagaga ctcctcagtg agaagaagac cgcacagtgc     960
cctcaccggt tcagaagac atgtagcccc attatggtga gcaagggcga ggagctgttc    1020
accggggtgg tgcccatcct ggtcgagctg gacggcgacg taaacggcca caagttcagc    1080
gtgtccggcg agggcgaggg cgatgccacc tacggcaagc tgaccctgaa gttcatctgc    1140
accaccggca agctgcccgt gccctggccc accctcgtga ccaccttgac ctacggcgtg    1200
cagtgcttcg cccgctaccc cgaccacatg aagcagcacg acttcttcaa gtccgccatg    1260
cccgaaggct acgtccagga gcgcaccatc ttcttcaagg acgacggcaa ctacaagacc    1320
```

```
cgcgccgagg tgaagttcga gggcgacacc ctggtgaacc gcatcgagct gaagggcatc    1380
gacttcaagg aggacggcaa catcctgggg cacaagctgg agtacaacta caacagccac    1440
aaggtctata tcaccgccga caagcagaag aacggcatca aggtgaactt caagacccgc    1500
cacaacatcg aggacggcag cgtgcagctc gccgaccact accagcagaa caccccccatc    1560 ggcgacggcc ccgtgctgct gcccgacaac cactacctga gcacccagtc cgccctgagc    1620
aaagacccca cgagaagcg cgatcacatg gtcctgctgg agttcgtgac cgccgccggg    1680
atcactctcg gcatggacga gctgtacaag tagtag                              1716
```

<210> SEQ ID NO 28
<211> LENGTH: 528
<212> TYPE: PRT
<213> ORGANISM: Artificial Sequence
<220> FEATURE:
<223> OTHER INFORMATION: hIgG2-hCD4-GFP construct without signal
      sequence and without FLAG tag

<400> SEQUENCE: 28

```
Cys Val Glu Cys Pro Pro Cys Pro Ala Pro Pro Val Ala Gly Pro Ser
1               5                   10                  15

Val Phe Leu Phe Pro Pro Lys Pro Lys Asp Thr Leu Met Ile Ser Arg
            20                  25                  30

Thr Pro Glu Val Thr Cys Val Val Asp Val Ser His Glu Asp Pro
        35                  40                  45

Glu Val Gln Phe Asn Trp Tyr Val Asp Gly Val Glu Val His Asn Ala
    50                  55                  60

Lys Thr Lys Pro Arg Glu Gln Phe Asn Ser Thr Phe Arg Val Val
65                  70                  75                  80

Ser Val Leu Thr Val Val His Gln Asp Trp Leu Asn Gly Lys Glu Tyr
                85                  90                  95

Lys Cys Lys Val Ser Asn Lys Gly Leu Pro Ala Pro Ile Glu Lys Thr
            100                 105                 110

Ile Ser Lys Thr Lys Gly Gln Pro Arg Glu Pro Gln Val Tyr Thr Leu
        115                 120                 125

Pro Pro Ser Arg Glu Glu Met Thr Lys Asn Gln Val Ser Leu Thr Cys
    130                 135                 140

Leu Val Lys Gly Phe Tyr Pro Ser Asp Ile Ala Val Glu Trp Glu Ser
145                 150                 155                 160

Asn Gly Gln Pro Glu Asn Asn Tyr Lys Thr Thr Pro Pro Met Leu Asp
                165                 170                 175

Ser Asp Gly Ser Phe Phe Leu Tyr Ser Lys Leu Thr Val Asp Lys Ser
            180                 185                 190

Arg Trp Gln Gln Gly Asn Val Phe Ser Cys Ser Val Met His Glu Ala
        195                 200                 205

Leu His Asn His Tyr Thr Gln Lys Ser Leu Ser Leu Ser Pro Gly Lys
    210                 215                 220

Gly Arg Ala Met Ala Leu Ile Val Leu Gly Gly Val Ala Gly Leu Leu
225                 230                 235                 240

Leu Phe Ile Gly Leu Gly Ile Phe Phe Cys Val Arg Cys Arg His Arg
                245                 250                 255

Arg Arg Gln Ala Glu Arg Met Ser Gln Ile Lys Arg Leu Leu Ser Glu
            260                 265                 270

Lys Lys Thr Ala Gln Cys Pro His Arg Phe Gln Lys Thr Cys Ser Pro
        275                 280                 285
```

```
Ile Met Val Ser Lys Gly Glu Glu Leu Phe Thr Gly Val Val Pro Ile
290                 295                 300

Leu Val Glu Leu Asp Gly Asp Val Asn Gly His Lys Phe Ser Val Ser
305                 310                 315                 320

Gly Glu Gly Glu Gly Asp Ala Thr Tyr Gly Lys Leu Thr Leu Lys Phe
            325                 330                 335

Ile Cys Thr Thr Gly Lys Leu Pro Val Pro Trp Pro Thr Leu Val Thr
                340                 345                 350

Thr Leu Thr Tyr Gly Val Gln Cys Phe Ala Arg Tyr Pro Asp His Met
            355                 360                 365

Lys Gln His Asp Phe Phe Lys Ser Ala Met Pro Glu Gly Tyr Val Gln
370                 375                 380

Glu Arg Thr Ile Phe Phe Lys Asp Asp Gly Asn Tyr Lys Thr Arg Ala
385                 390                 395                 400

Glu Val Lys Phe Glu Gly Asp Thr Leu Val Asn Arg Ile Glu Leu Lys
            405                 410                 415

Gly Ile Asp Phe Lys Glu Asp Gly Asn Ile Leu Gly His Lys Leu Glu
                420                 425                 430

Tyr Asn Tyr Asn Ser His Lys Val Tyr Ile Thr Ala Asp Lys Gln Lys
            435                 440                 445

Asn Gly Ile Lys Val Asn Phe Lys Thr Arg His Asn Ile Glu Asp Gly
450                 455                 460

Ser Val Gln Leu Ala Asp His Tyr Gln Gln Asn Thr Pro Ile Gly Asp
465                 470                 475                 480

Gly Pro Val Leu Leu Pro Asp Asn His Tyr Leu Ser Thr Gln Ser Ala
            485                 490                 495

Leu Ser Lys Asp Pro Asn Glu Lys Arg Asp His Met Val Leu Leu Glu
                500                 505                 510

Phe Val Thr Ala Ala Gly Ile Thr Leu Gly Met Asp Glu Leu Tyr Lys
            515                 520                 525

<210> SEQ ID NO 29
<211> LENGTH: 1590
<212> TYPE: DNA
<213> ORGANISM: Artificial Sequence
<220> FEATURE:
<223> OTHER INFORMATION: hIgG2-hCD4-GFP construct without signal
      sequence and without FLAG tag

<400> SEQUENCE: 29
tgtgtcgagt gcccaccttg cccagcacca cctgtggcag gaccttcagt cttcctcttc      60
cccccaaaac ccaaggacac cctcatgatc tcccggaccc ctgaggtcac atgcgtggtg     120
gtggacgtga gccacgaaga ccccgaggtc cagtttaatt ggtatgtcga cggcgtggag     180
gtgcataatg ccaagacaaa gccacgggag gagcagttca acagcacatt cagggtggtc     240
agcgtcctca ccgttgtgca ccaggactgg ctgaacggca aggagtacaa gtgcaaggtg     300
tccaacaaag gcctcccagc ccccatcgag aaaaccatct ccaaaaccaa agggcagccc     360
agagaaccac aggtgtacac cctgccccca tcccgggagg agatgaccaa gaaccaggtc     420
agcctgacct gcctggtgaa gggattttat ccttccgaca tcgccgtgga gtgggagagc     480
aatgggcagc ctgagaacaa ctacaagacc acacctccca tgctggactc cgacggctcc     540
ttcttcctgt attccaaact caccgtggac aagagcaggt ggcagcaggg gaacgtcttc     600
tcatgctccg tgatgcatga ggctctgcac aaccactaca cacagaagag cctctccctg     660
tcccctggaa aggggcgcgc catggccctg attgtgctgg gggcgtcgc cggcctcctg     720
```

```
cttttcattg ggctcggcat cttcttctgt gtccgctgcc ggcaccgacg ccgccaagca      780
gagcggatgt ctcagatcaa gagactcctc agtgagaaga agaccgcaca gtgccctcac      840
cggtttcaga agacatgtag ccccattatg gtgagcaagg gcgaggagct gttcaccggg      900
gtggtgccca tcctggtcga gctggacggc gacgtaaacg gccacaagtt cagcgtgtcc      960
ggcgagggcg agggcgatgc cacctacggc aagctgaccc tgaagttcat ctgcaccacc     1020
ggcaagctgc ccgtgccctg gcccaccctc gtgaccacct tgacctacgg cgtgcagtgc     1080
ttcgcccgct accccgacca catgaagcag cacgacttct tcaagtccgc catgcccgaa     1140
ggctacgtcc aggagcgcac catcttcttc aaggacgacg gcaactacaa gacccgcgcc     1200
gaggtgaagt tcgagggcga caccctggtg aaccgcatcg agctgaaggg catcgacttc     1260
aaggaggacg gcaacatcct ggggcacaag ctggagtaca actacaacag ccacaaggtc     1320
tatatcaccg ccgacaagca gaagaacggc atcaaggtga acttcaagac ccgccacaac     1380
atcgaggacg gcagcgtgca gctcgccgac cactaccagc agaacacccc catcggcgac     1440
ggccccgtgc tgctgcccga caaccactac ctgagcaccc agtccgccct gagcaaagac     1500
cccaacgaga agcgcgatca catggtcctg ctggagttcg tgaccgccgc cgggatcact     1560
ctcggcatgg acgagctgta caagtagtag                                      1590
```

<210> SEQ ID NO 30
<211> LENGTH: 555
<212> TYPE: PRT
<213> ORGANISM: Artificial Sequence
<220> FEATURE:
<223> OTHER INFORMATION: hIgG2-hCD4-GFP construct, mature protein

<400> SEQUENCE: 30

```
Asp Tyr Lys Asp His Asp Gly Asp Tyr Lys Asp His Asp Ile Asp Tyr
1               5                   10                  15

Lys Asp Asp Asp Asp Lys Ala Ile Ala Asn Gly Cys Val Glu Cys Pro
            20                  25                  30

Pro Cys Pro Ala Pro Pro Val Ala Gly Pro Ser Val Phe Leu Phe Pro
        35                  40                  45

Pro Lys Pro Lys Asp Thr Leu Met Ile Ser Arg Thr Pro Glu Val Thr
    50                  55                  60

Cys Val Val Val Asp Val Ser His Glu Asp Pro Glu Val Gln Phe Asn
65                  70                  75                  80

Trp Tyr Val Asp Gly Val Glu Val His Asn Ala Lys Thr Lys Pro Arg
                85                  90                  95

Glu Glu Gln Phe Asn Ser Thr Phe Arg Val Val Ser Val Leu Thr Val
            100                 105                 110

Val His Gln Asp Trp Leu Asn Gly Lys Glu Tyr Lys Cys Lys Val Ser
        115                 120                 125

Asn Lys Gly Leu Pro Ala Pro Ile Glu Lys Thr Ile Ser Lys Thr Lys
    130                 135                 140

Gly Gln Pro Arg Glu Pro Gln Val Tyr Thr Leu Pro Pro Ser Arg Glu
145                 150                 155                 160

Glu Met Thr Lys Asn Gln Val Ser Leu Thr Cys Leu Val Lys Gly Phe
                165                 170                 175

Tyr Pro Ser Asp Ile Ala Val Glu Trp Glu Ser Asn Gly Gln Pro Glu
            180                 185                 190

Asn Asn Tyr Lys Thr Thr Pro Pro Met Leu Asp Ser Asp Gly Ser Phe
        195                 200                 205
```

Phe Leu Tyr Ser Lys Leu Thr Val Asp Lys Ser Arg Trp Gln Gln Gly
              210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly Lys Gly Arg Ala Met Ala
                245                 250                 255

Leu Ile Val Leu Gly Val Ala Gly Leu Leu Phe Ile Gly Leu
                260                 265                 270

Gly Ile Phe Phe Cys Val Arg Cys Arg His Arg Arg Gln Ala Glu
                275                 280                 285

Arg Met Ser Gln Ile Lys Arg Leu Leu Ser Glu Lys Lys Thr Ala Gln
    290                 295                 300

Cys Pro His Arg Phe Gln Lys Thr Cys Ser Pro Ile Met Val Ser Lys
305                 310                 315                 320

Gly Glu Glu Leu Phe Thr Gly Val Val Pro Ile Leu Val Glu Leu Asp
                325                 330                 335

Gly Asp Val Asn Gly His Lys Phe Ser Val Ser Gly Glu Gly Gly
                340                 345                 350

Asp Ala Thr Tyr Gly Lys Leu Thr Leu Lys Phe Ile Cys Thr Thr Gly
                355                 360                 365

Lys Leu Pro Val Pro Trp Pro Thr Leu Val Thr Thr Leu Thr Tyr Gly
370                 375                 380

Val Gln Cys Phe Ala Arg Tyr Pro Asp His Met Lys Gln His Asp Phe
385                 390                 395                 400

Phe Lys Ser Ala Met Pro Glu Gly Tyr Val Gln Glu Arg Thr Ile Phe
                405                 410                 415

Phe Lys Asp Asp Gly Asn Tyr Lys Thr Arg Ala Glu Val Lys Phe Glu
                420                 425                 430

Gly Asp Thr Leu Val Asn Arg Ile Glu Leu Lys Gly Ile Asp Phe Lys
                435                 440                 445

Glu Asp Gly Asn Ile Leu Gly His Lys Leu Glu Tyr Asn Tyr Asn Ser
    450                 455                 460

His Lys Val Tyr Ile Thr Ala Asp Lys Gln Lys Asn Gly Ile Lys Val
465                 470                 475                 480

Asn Phe Lys Thr Arg His Asn Ile Glu Asp Gly Ser Val Gln Leu Ala
                485                 490                 495

Asp His Tyr Gln Gln Asn Thr Pro Ile Gly Asp Gly Pro Val Leu Leu
                500                 505                 510

Pro Asp Asn His Tyr Leu Ser Thr Gln Ser Ala Leu Ser Lys Asp Pro
                515                 520                 525

Asn Glu Lys Arg Asp His Met Val Leu Leu Glu Phe Val Thr Ala Ala
    530                 535                 540

Gly Ile Thr Leu Gly Met Asp Glu Leu Tyr Lys
545                 550                 555

<210> SEQ ID NO 31
<211> LENGTH: 312
<212> TYPE: PRT
<213> ORGANISM: Artificial Sequence
<220> FEATURE:
<223> OTHER INFORMATION: mIgG1-hCD4 construct, mature protein

<400> SEQUENCE: 31

Asp Tyr Lys Asp His Asp Gly Asp Tyr Lys Asp His Asp Ile Asp Tyr
1               5                   10                  15

```
Lys Asp Asp Asp Asp Lys Ala Ile Ala Gly Cys Lys Pro Cys Ile Cys
                20                  25                  30

Thr Val Pro Glu Val Ser Ser Val Phe Ile Phe Pro Pro Lys Pro Lys
            35                  40                  45

Asp Val Leu Thr Ile Thr Leu Thr Pro Lys Val Thr Cys Val Val Val
         50                  55                  60

Asp Ile Ser Lys Asp Asp Pro Glu Val Gln Phe Ser Trp Phe Val Asp
65                  70                  75                  80

Asp Val Glu Val His Thr Ala Gln Thr Gln Pro Arg Glu Glu Gln Phe
                85                  90                  95

Asn Ser Thr Phe Arg Ser Val Ser Glu Leu Pro Ile Met His Gln Asp
            100                 105                 110

Trp Leu Asn Gly Lys Glu Phe Lys Cys Arg Val Asn Ser Ala Ala Phe
        115                 120                 125

Pro Ala Pro Ile Glu Lys Thr Ile Ser Lys Thr Lys Gly Arg Pro Lys
    130                 135                 140

Ala Pro Gln Val Tyr Thr Ile Pro Pro Pro Lys Glu Gln Met Ala Lys
145                 150                 155                 160

Asp Lys Val Ser Leu Thr Cys Met Ile Thr Asp Phe Phe Pro Glu Asp
                165                 170                 175

Ile Thr Val Glu Trp Gln Trp Asn Gly Gln Pro Ala Glu Asn Tyr Lys
            180                 185                 190

Asn Thr Gln Pro Ile Met Asp Thr Asp Gly Ser Tyr Phe Val Tyr Ser
        195                 200                 205

Lys Leu Asn Val Gln Lys Ser Asn Trp Glu Ala Gly Asn Thr Phe Thr
    210                 215                 220

Cys Ser Val Leu His Glu Gly Leu His Asn His His Thr Glu Lys Ser
225                 230                 235                 240

Leu Ser His Ser Pro Gly Lys Gly Arg Ala Met Ala Leu Ile Val Leu
                245                 250                 255

Gly Gly Val Ala Gly Leu Leu Leu Phe Ile Gly Leu Gly Ile Phe Phe
            260                 265                 270

Cys Val Arg Cys Arg His Arg Arg Gln Ala Glu Arg Met Ser Gln
        275                 280                 285

Ile Lys Arg Leu Leu Ser Glu Lys Lys Thr Cys Gln Cys Pro His Arg
    290                 295                 300

Phe Gln Lys Thr Cys Ser Pro Ile
305                 310

<210> SEQ ID NO 32
<211> LENGTH: 316
<212> TYPE: PRT
<213> ORGANISM: Artificial Sequence
<220> FEATURE:
<223> OTHER INFORMATION: hIgG2-hCD4 construct, mature protein

<400> SEQUENCE: 32

Asp Tyr Lys Asp His Asp Gly Asp Tyr Lys Asp His Asp Ile Asp Tyr
1               5                   10                  15

Lys Asp Asp Asp Asp Lys Ala Ile Ala Asn Gly Cys Val Glu Cys Pro
                20                  25                  30

Pro Cys Pro Ala Pro Pro Val Ala Gly Pro Ser Val Phe Leu Phe Pro
            35                  40                  45

Pro Lys Pro Lys Asp Thr Leu Met Ile Ser Arg Thr Pro Glu Val Thr
        50                  55                  60
```

Cys Val Val Asp Val Ser His Glu Asp Pro Glu Val Gln Phe Asn
65                  70                  75                  80

Trp Tyr Val Asp Gly Val Glu Val His Asn Ala Lys Thr Lys Pro Arg
                85                  90                  95

Glu Glu Gln Phe Asn Ser Thr Phe Arg Val Val Ser Val Leu Thr Val
            100                 105                 110

Val His Gln Asp Trp Leu Asn Gly Lys Glu Tyr Lys Cys Lys Val Ser
        115                 120                 125

Asn Lys Gly Leu Pro Ala Pro Ile Glu Lys Thr Ile Ser Lys Thr Lys
130                 135                 140

Gly Gln Pro Arg Glu Pro Gln Val Tyr Thr Leu Pro Pro Ser Arg Glu
145                 150                 155                 160

Glu Met Thr Lys Asn Gln Val Ser Leu Thr Cys Leu Val Lys Gly Phe
                165                 170                 175

Tyr Pro Ser Asp Ile Ala Val Glu Trp Glu Ser Asn Gly Gln Pro Glu
            180                 185                 190

Asn Asn Tyr Lys Thr Thr Pro Pro Met Leu Asp Ser Asp Gly Ser Phe
        195                 200                 205

Phe Leu Tyr Ser Lys Leu Thr Val Asp Lys Ser Arg Trp Gln Gln Gly
210                 215                 220

Asn Val Phe Ser Cys Ser Val Met His Glu Ala Leu His Asn His Tyr
225                 230                 235                 240

Thr Gln Lys Ser Leu Ser Leu Ser Pro Gly Lys Gly Arg Ala Met Ala
                245                 250                 255

Leu Ile Val Leu Gly Gly Val Ala Gly Leu Leu Leu Phe Ile Gly Leu
            260                 265                 270

Gly Ile Phe Phe Cys Val Arg Cys Arg His Arg Arg Arg Gln Ala Glu
        275                 280                 285

Arg Met Ser Gln Ile Lys Arg Leu Leu Ser Glu Lys Lys Thr Ala Gln
290                 295                 300

Cys Pro His Arg Phe Gln Lys Thr Cys Ser Pro Ile
305                 310                 315

<210> SEQ ID NO 33
<211> LENGTH: 2142
<212> TYPE: DNA
<213> ORGANISM: Artificial Sequence
<220> FEATURE:
<223> OTHER INFORMATION: MAbLib construct (sc21M18 sequence)
<220> FEATURE:
<221> NAME/KEY: misc_feature
<222> LOCATION: (1)..(60)
<223> OTHER INFORMATION: signal

<400> SEQUENCE: 33
atggtactcc aaacccaagt attcatctcg ctgctgttgt ggattagcgg agcgtatgga      60
gatatcgtca tgacacagtc accgactcg cttgcagtat cgctcggcga gagggccacc     120
atttcgtgtc gcgcttcaga gtcagtcgat aactacggga tctcgtttat gaagtggttt     180
cagcagaagc ccggacaacc accgaagttg ctcatctacg cggcttcaaa tcagggtgtca     240 ggggtccctg acagattttc cggctccggt tccggtacag atttcacgct gaccatctcg     300
tcgctgcagg ccgaggacgt ggccgtgtat tactgccagc agtcaaaaga ggtcccctgg     360
acttttgggg gtgggacgaa agtggagatc aagcgtacgg tggcggcacc ttcagtgttt     420
atcttcccgc cgtccgacga acagcttaag tccggtacgg cgtcggtagt ctgcctgctg     480

-continued

```
aacaatttct atcccaggga agcgaaagta caatggaagg tcgacaatgc cctccagagc    540
gggaatagcc aagaatcggt cacagaacag gattcgaagg actcaacgta tagcctttcg    600
tccacactta cactctcgaa agctgactat gagaagcata aggtctatgc atgtgaagtc    660
actcatcaag gtctttcgtc gcccgtaacc aagagcttca accgcggaga gtgtggagga    720
ggtggtggat caggcggtgg tgggtcggga ggggtggca gcgaggagg gggatccggt      780
ggaggggta gcggggagg agggagccag gtgcaattgg tgcagtccgg ggcagaagtg       840
aagaagcctg gcgcgtcagt gaagatcagc tgcaaagcct cggggtattc ctttacagca    900
tactacattc actgggtcaa acaggcgcca ggacaggggt tggagtggat tggatacatt    960
tcctcgtaca acgggccac gaactacaat cagaaattca aggacgggt gacgtttact      1020
acggacacca gcacttcgac ggcgtacatg gagcttcgat cactccggtc cgatgacacg    1080
gctgtatact actgtgccag agattatgat tatgatgtgg gaatggacta ctggggacag    1140
gggacattgg taacagtgag ctcagccagc acaaagggcc ctagcgtctt ccctctggcc    1200
ccctgcagca ggagcaccag cgagagcaca gccgccctgg gctgcctggt caaggactac    1260
ttccccgaac cggtgacggt gtcgtggaac tcaggcgctc tgaccagcgg cgtgcacacc    1320
ttcccagctg tcctacagtc ctcaggactc tactccctca gcagcgtggt gaccgtgccc    1380
tccagcaact tcggcaccca gacctacacc tgcaacgtag atcacaagcc cagcaacacc    1440
aaggtggaca agacagttga gcgcaaatgt tgtgtcgagt gcccaccgtg cccagcacca    1500
cctgtggcag gaccgtcagt cttcctcttc cccccaaaac ccaaggacac cctcatgatc    1560
tcccggaccc ctgaggtcac gtgcgtggtg gtggacgtga gccacgaaga ccccgaggtc    1620
cagttcaact ggtacgtgga cggcgtggag gtgcataatg ccaagacaaa gccacgggag    1680
gagcagttca acagcacgtt ccgtgtggtc agcgtcctca ccgttgtgca ccaggactgg    1740
ctgaacggca aggagtacaa gtgcaaggtc tccaacaaag gcctcccagc ccccatcgag    1800
aaaaccatct ccaaaaccaa agggcagccc cgagaaccac aggtgtacac cctgcccca    1860
tcccgggagg agatgaccaa gaaccaggtc agcctgacct gcctggtcaa aggcttctac    1920
cccagcgaca tcgccgtgga gtgggagagc aatgggcagc cggagaacaa ctacaagacc    1980
acacctccca tgctggactc cgacggctcc ttcttcctct acagcaagct caccgtggac    2040
aagagcaggt ggcagcaggg gaacgtcttc tcatgctccg tgatgcatga ggctctgcac    2100
aaccactaca cgcagaagag cctctccctg tctccgggta aa                       2142
```

<210> SEQ ID NO 34
<211> LENGTH: 714
<212> TYPE: PRT
<213> ORGANISM: Artificial Sequence
<220> FEATURE:
<223> OTHER INFORMATION: MAbLib construct (sc21M18 sequence)
<220> FEATURE:
<221> NAME/KEY: MISC_FEATURE
<222> LOCATION: (1)..(20)
<223> OTHER INFORMATION: signal

<400> SEQUENCE: 34

```
Met Val Leu Gln Thr Gln Val Phe Ile Ser Leu Leu Trp Ile Ser
1               5                   10                  15

Gly Ala Tyr Gly Asp Ile Val Met Thr Gln Ser Pro Asp Ser Leu Ala
            20                  25                  30

Val Ser Leu Gly Glu Arg Ala Thr Ile Ser Cys Arg Ala Ser Glu Ser
        35                  40                  45
```

-continued

Val Asp Asn Tyr Gly Ile Ser Phe Met Lys Trp Phe Gln Gln Lys Pro
    50                  55                  60

Gly Gln Pro Pro Lys Leu Leu Ile Tyr Ala Ala Ser Asn Gln Gly Ser
65                  70                  75                  80

Gly Val Pro Asp Arg Phe Ser Gly Ser Gly Ser Gly Thr Asp Phe Thr
                85                  90                  95

Leu Thr Ile Ser Ser Leu Gln Ala Glu Asp Val Ala Val Tyr Tyr Cys
                100                 105                 110

Gln Gln Ser Lys Glu Val Pro Trp Thr Phe Gly Gly Gly Thr Lys Val
                115                 120                 125

Glu Ile Lys Arg Thr Val Ala Ala Pro Ser Val Phe Ile Phe Pro Pro
        130                 135                 140

Ser Asp Glu Gln Leu Lys Ser Gly Thr Ala Ser Val Val Cys Leu Leu
145                 150                 155                 160

Asn Asn Phe Tyr Pro Arg Glu Ala Lys Val Gln Trp Lys Val Asp Asn
                165                 170                 175

Ala Leu Gln Ser Gly Asn Ser Gln Glu Ser Val Thr Glu Gln Asp Ser
                180                 185                 190

Lys Asp Ser Thr Tyr Ser Leu Ser Ser Thr Leu Thr Leu Ser Lys Ala
            195                 200                 205

Asp Tyr Glu Lys His Lys Val Tyr Ala Cys Glu Val Thr His Gln Gly
        210                 215                 220

Leu Ser Ser Pro Val Thr Lys Ser Phe Asn Arg Gly Glu Cys Gly Gly
225                 230                 235                 240

Gly Gly Gly Ser Gly Gly Gly Gly Ser Gly Gly Gly Gly Ser Gly Gly
                245                 250                 255

Gly Gly Ser Gly Gly Gly Gly Ser Gly Gly Gly Gly Ser Gln Val Gln
                260                 265                 270

Leu Val Gln Ser Gly Ala Glu Val Lys Lys Pro Gly Ala Ser Val Lys
            275                 280                 285

Ile Ser Cys Lys Ala Ser Gly Tyr Ser Phe Thr Ala Tyr Tyr Ile His
        290                 295                 300

Trp Val Lys Gln Ala Pro Gly Gln Gly Leu Glu Trp Ile Gly Tyr Ile
305                 310                 315                 320

Ser Ser Tyr Asn Gly Ala Thr Asn Tyr Asn Gln Lys Phe Lys Gly Arg
                325                 330                 335

Val Thr Phe Thr Thr Asp Thr Ser Thr Ala Tyr Met Glu Leu
                340                 345                 350

Arg Ser Leu Arg Ser Asp Asp Thr Ala Val Tyr Tyr Cys Ala Arg Asp
            355                 360                 365

Tyr Asp Tyr Asp Val Gly Met Asp Tyr Trp Gly Gln Gly Thr Leu Val
        370                 375                 380

Thr Val Ser Ser Ala Ser Thr Lys Gly Pro Ser Val Phe Pro Leu Ala
385                 390                 395                 400

Pro Cys Ser Arg Ser Thr Ser Glu Ser Thr Ala Ala Leu Gly Cys Leu
                405                 410                 415

Val Lys Asp Tyr Phe Pro Glu Pro Val Thr Val Ser Trp Asn Ser Gly
                420                 425                 430

Ala Leu Thr Ser Gly Val His Thr Phe Pro Ala Val Leu Gln Ser Ser
            435                 440                 445

Gly Leu Tyr Ser Leu Ser Ser Val Val Thr Val Pro Ser Ser Asn Phe
        450                 455                 460

Gly Thr Gln Thr Tyr Thr Cys Asn Val Asp His Lys Pro Ser Asn Thr

-continued

```
            465                 470                 475                 480
Lys Val Asp Lys Thr Val Glu Arg Lys Cys Cys Val Glu Cys Pro Pro
                485                 490                 495

Cys Pro Ala Pro Pro Val Ala Gly Pro Ser Val Phe Leu Phe Pro Pro
                500                 505                 510

Lys Pro Lys Asp Thr Leu Met Ile Ser Arg Thr Pro Glu Val Thr Cys
                515                 520                 525

Val Val Val Asp Val Ser His Glu Asp Pro Glu Val Gln Phe Asn Trp
                530                 535                 540

Tyr Val Asp Gly Val Glu Val His Asn Ala Lys Thr Lys Pro Arg Glu
545                 550                 555                 560

Glu Gln Phe Asn Ser Thr Phe Arg Val Val Ser Val Leu Thr Val Val
                565                 570                 575

His Gln Asp Trp Leu Asn Gly Lys Glu Tyr Lys Cys Lys Val Ser Asn
                580                 585                 590

Lys Gly Leu Pro Ala Pro Ile Glu Lys Thr Ile Ser Lys Thr Lys Gly
                595                 600                 605

Gln Pro Arg Glu Pro Gln Val Tyr Thr Leu Pro Pro Ser Arg Glu Glu
                610                 615                 620

Met Thr Lys Asn Gln Val Ser Leu Thr Cys Leu Val Lys Gly Phe Tyr
625                 630                 635                 640

Pro Ser Asp Ile Ala Val Glu Trp Glu Ser Asn Gly Gln Pro Glu Asn
                645                 650                 655

Asn Tyr Lys Thr Thr Pro Pro Met Leu Asp Ser Asp Gly Ser Phe Phe
                660                 665                 670

Leu Tyr Ser Lys Leu Thr Val Asp Lys Ser Arg Trp Gln Gln Gly Asn
                675                 680                 685

Val Phe Ser Cys Ser Val Met His Glu Ala Leu His Asn His Tyr Thr
                690                 695                 700

Gln Lys Ser Leu Ser Leu Ser Pro Gly Lys
705                 710
```